United States Patent [19]

Barth

[11] 4,109,083

[45] Aug. 22, 1978

[54] 4-(TETRAZOL-5-YL)-Δ³-CEPHEM COMPOUNDS

[75] Inventor: Wayne E. Barth, East Lyme, Conn.

[73] Assignee: Pfizer Inc., New York, N.Y.

[21] Appl. No.: 791,214

[22] Filed: Apr. 27, 1977

Related U.S. Application Data

[60] Division of Ser. No. 658,292, Feb. 17, 1976, Pat. No. 4,039,532, which is a division of Ser. No. 508,634, Sep. 23, 1974, Pat. No. 3,966,719, which is a continuation-in-part of Ser. No. 407,097, Oct. 17, 1973, abandoned.

[51] Int. Cl.² .......................................... C07D 501/36
[52] U.S. Cl. ......................................... 544/26; 424/246
[58] Field of Search .............................. 544/30, 27, 26

[56] References Cited

U.S. PATENT DOCUMENTS 4,039,532   8/1977   Barth ...................................... 544/30

*Primary Examiner*—Nicholas S. Rizzo
*Attorney, Agent, or Firm*—Connolly and Hutz

[57] ABSTRACT

Certain novel antibacterial 7-acylamino-3-substituted-4-(tetrazol-5-yl)-Δ³-cephem derivatives, and salts thereof, and intermediates useful in their preparation.

6 Claims, No Drawings

4-(TETRAZOL-5-YL)-Δ³-CEPHEM COMPOUNDS

CROSS-REFERENCE TO RELATED APPLICATIONS

This application is a division of application Ser. No. 658,292 filed Feb. 17, 1976 now U.S. Pat. No. 4,039,532 which, in turn, is a division of application Ser. No. 508,634 filed Sept. 23, 1974 and now U.S. Pat. No. 3,966,719 which, in turn, is a continuation-in-part of application Ser. No. 407,097 filed Oct. 17, 1973 and now abandoned.

BACKGROUND OF THE INVENTION

1. Field of the Invention

This invention relates to novel antibacterial agents which are of value as animal feed supplements, as therapeutic agents for the control of infectious diseases caused by gram-positive and gram-negative bacteria, and for the sterilization of hospital surfaces and the like; and to novel intermediates for their production. More specifically, the antibacterial compounds of the instant invention are acylated derivatives of 7-amino-3-substituted-Δ³-cephem compounds which bear a 5-tetrazolyl group at the 4-position.

2. Description of the Prior Art

In spite of the large number of cephem derivatives which have been proposed for use as antibacterial agents, there still exists a need for new agents.

The antibacterial compounds of this invention, and the intermediates from which they are prepared by acylation, are all novel, and they are completely unanticipated in the prior art. U.S. Pat. No. 3,427,302 and 3,468,874 disclose penam derivatives which incorporate a tetrazolyl group as part of the 6-acylamino substituent, and Japanese Patent Publication 71-38503 discloses cephem derivatives which incorporate a tetrazolyl group as part of the 7-acylamino substituent. Cephem derivatives with a tetrazolylthiomethyl group at the 3-position are also known (U.S. Pat. No. 3,641,021). However, the compounds of the instant invention are unique in having a tetrazolyl group bonded directly to the cephem nucleus.

The biological and non-biological uses of tetrazoles has recently been reviewed by Benson, "Heterocyclic Compounds," Elderfield, Ed., Vol. 8, John Wiley & Sons, Inc., New York, N.Y., 1967, Chapter 1, while a compilation of cephem references is noted in U.S. Pat. No. 3,766,176.

SUMMARY OF THE INVENTION

It has now been found that certain 7-acylamino-3-substituted-4-(tetrazol-5-yl)-Δ³-cephems and their salts are useful as antibacterial agents, while certain 7-substituted amino-3-substituted-4-carbamoyl- and 4-(tetrazol-5-yl)-Δ³- and -Δ²-cephems are valuable intermediates leading to the preparation of these antibiotics.

A preferred group of compounds useful as intermediates are those of the formula

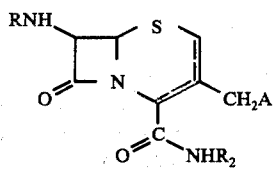

wherein R is hydrogen or an amino protecting moiety selected from the group consisting of 2,2,2-trichloroethoxycarbonyl, 2,2,2-tribromoethoxycarbonyl, benzyloxycarbonyl and

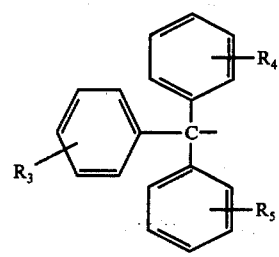

where $R_3$, $R_4$ and $R_5$ are each hydrogen, chloro, bromo, fluoro, methyl, methoxy or phenyl; A is hydrogen, acetoxy, 1-methyltetrazolylthio or 2-methyl-1,3,4-thiadiazolyl-5-thio; and $R_2$ is a potential tetrazole protecting moiety selected from the group consisting of

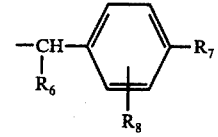

where $R_6$ is hydrogen, alkyl having from one to three carbon atoms or phenyl, $R_7$ is hydroxy, methoxy, alkanoyloxy having two to four carbon atoms or benzyloxy and $R_8$ is hydrogen, hydroxy, fluoro, chloro, bromo, iodo, methyl, methoxy, alkanoyloxy having two to four carbon atoms, phenyl or benzyloxy and

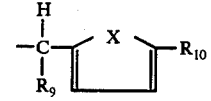

where $R_9$ and $R_{10}$ are each hydrogen or methyl and X is oxygen or sulfur.

A second preferred class of compounds are intermediates of the formulae

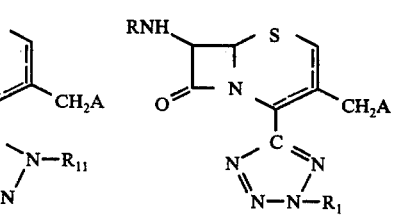

and the salts thereof where R is hydrogen or an amino protecting group selected from the group consisting of 2,2,2-trichloroethoxycarbonyl, 2,2,2-tribromoethoxycarbonyl, benzyloxycarbonyl and

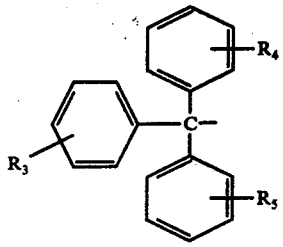

where $R_3$, $R_4$ and $R_5$ are each hydrogen, chloro, bromo, fluoro, methyl, methoxy or phenyl; A is hydrogen, acetoxy, 1-methyl-5-tetrazolylthio or 2-methyl-1,3,4-thiadiazolyl-5-thio; $R_1$ is hydrogen, alkanoyloxymethyl having from three to six carbon atoms, 1-(alkanoyloxy)ethyl having from four to seven carbon atoms, methoxymethyl or phthalidyl; and $R_{11}$ is hydrogen, alkanoyloxymethyl having from three to six carbon atoms, 1-(alkanoyloxy)ethyl having from four to seven carbon atoms, methoxymethyl, phthalidyl or a potential tetrazole protecting moiety selected from the group consisting of

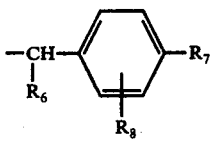

where $R_6$ is hydrogen, alkyl having from one to three carbon atoms or phenyl, $R_7$ is hydroxy, methoxy, alkanoyloxy having from two to four carbon atoms or benzyloxy and $R_8$ is hydrogen, hydroxy, fluoro, chloro, bromo, iodo, methyl, methoxy, alkanoyloxy having from two to four carbon atoms, phenyl or benzyloxy and

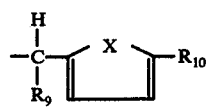

where $R_9$ and $R_{10}$ are each hydrogen or methyl and X is sulfur or oxygen.

A third class of preferred cephem derivatives and their salts are those of the formula

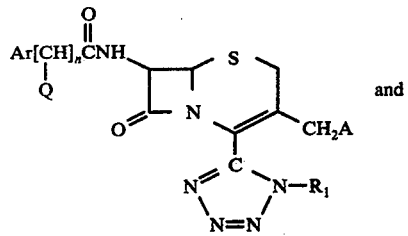

and

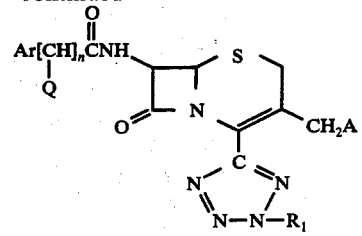

where Ar is cyano, bromo, phenyl mono- or disubstituted phenyl where each substituent is hydroxy, fluoro, chloro, bromo, amino, methoxy or methyl, phenoxy, phenylthio, pyridylthio, thienyl, 2-methyl-1,3,4-thiadiazol-5-ylthio or 1-tetrazolyl; Q is hydrogen, hydroxy, azide, amino or carboxy; n is an integer of 0 or 1; A is hydrogen, acetoxy, 1-methyltetrazol-5-ylthio or 2-methyl 1,3,4-thiadiazol-5-ylthio; and $R_1$ is hydrogen, alkanoyloxymethyl having from three to six carbon atoms, 1-(alkanoyloxy)ethyl having from four to seven carbon atoms, methoxymethyl or phthalidyl, provided that when Ar is pyridylthio, phenoxy, phenylthio, 2-methyl-1,3,4-thiadiazol-5-ylthiomethyl, cyano or bromo, and n is 1, Q is hydrogen or carboxy.

Also considered within the scope of the present invention are compounds of the third preferred class wherein A, Q, n, and $R_1$ are as defined and Ar is selected from the group consisting of hydrogen, alkyl having from one to twelve carbon atoms, alkenyl having from two to twelve carbon atoms, cycloalkyl having from three to seven carbon atoms, cycloalkenyl having from five to eight carbon atoms, cycloheptatrienyl, 1,4-cyclohexadienyl, 1-aminocycloalkyl having from four to seven carbon atoms, 5-methyl-3-phenyl-4-isoxazolyl, 5-methyl-3-(o-chlorophenyl)-4-isoxazolyl, 5-methyl-3-(2,6-dichlorophenyl)-4-isoxazolyl, 5-methyl-3-(2-chloro-6-fluorophenyl)-4-isoxazolyl, 2-alkoxy-1-naphthyl having from one to four carbon atoms in said alkoxy, sydnonyl, furyl, pyridyl, thiazolyl, isothiazolyl, pyrimidinyl, triazolyl, imidazolyl, pyrazolyl, substituted phenoxy, substituted phenylthio, substituted pyridylthio, substituted thienyl, substituted furyl, substituted pyridyl, substituted tetrazolyl, substituted thiazolyl, substituted isothiazolyl, substituted pyrimidinyl, substituted triazolyl, substituted imidazolyl and substituted pyrazolyl, each substituted moiety being substituted by up to two members selected from the group consisting of fluoro, chloro, bromo, hydroxy, hydroxymethyl, amino, N,N-dialkylamino having from one to four carbon atoms in each of said alkyl groups, alkyl having from one to four carbon atoms, aminomethyl, aminoethyl, alkoxy having from one to four carbon atoms, alkylthio having from one to four carbon atoms, 2-aminoethoxy and N-alkylamino having from one to four carbon atoms.

As one skilled in the art can readily appreciate, the α-carbon atom of the antibacterial cephem side chain to which the amino or hydroxy, (Q) moiety is attached is an asymmetric carbon atom allowing for the existence of two optically active isomers, the D- and L-diastereoisomers, as well as the racemate, DL, form. In accord with previous findings concerning the activity of such cephems possessing asymmetric α-carbon atoms, the compounds of the present invention possessing the D-configuration are more active than those of the L-configuration and are the preferred compounds, although the L and DL forms of the instant compounds are also considered within the purview of the present invention.

Further, it is noteworthy to mention while considering asymmetric centers, that there are several in the $\Delta^3$-cephem nucleus, the basic building block from which the compounds of the present invention are derived. These potential additional isomers are not significant in this instance since the 7-amino-$\Delta^3$-cephem-4-carboxylic acid employed leading to the products of this invention is that which is produced by fermentation and is consistently of one configuration.

In like manner, the term "tetrazole protecting group" or "tetrazolyl cephem nitrogen protecting group" is intended to connote all groups known, or obvious, to one skilled in the art, which can be used (a) to permit the synthesis of the compounds wherein R is an amino protecting group and $R^2$ is the said tetrazolylcephem nitrogen protecting group, by the process starting with 7-(protected amino)cephem-4-carboxylic acid described hereinafter; and (b) can be removed from said compound wherein $R^2$ is the said tetrazolylcephem nitrogen protecting group, wherein R is selected from the group consisting of hydrogen and an amino protecting group, and $R^2$ is the said tetrazolylcephem nitrogen protecting group, using a method wherein the cephem ring system remains substantially intact. It is likewise the ability of the tetrazolylcephem nitrogen protecting group to perform a specific function, to be discussed in more detail hereinafter, rather than its precise chemical structure, which is important; and the novelty of the antibacterial agents of the invention does not depend upon the structure of the protecting group. Selection and identification of appropriate protecting groups can be made readily and easily by one skilled in the art, and examples of several applicable groups are given hereinafter.

DETAILED DESCRIPTION OF THE INVENTION

This invention relates to certain new and novel compositions of matter which are valuable as antibacterial agents, and as intermediates for preparing said agents. For the sake of convenience, these compounds are identified as derivatives of $\Delta^3$-cephem. The term "$\Delta^3$-cephem" has been defined by Morin et al. in the *Journal of the American Chemical Society*, 84, 3400 (1962) as meaning the structure

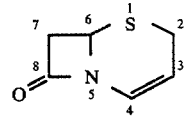

Using this terminology, the well-known antibiotic cephalosporin C, is designated as 7-(5-amino-5-carboxyvaleramido)-3-acetoxymethyl-$\Delta^3$-cephem-4-carboxylic acid.

Many of the compounds of this invention are also 5-substituted tetrazoles which can exist in two isomeric forms, viz:

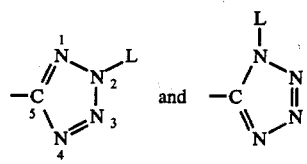

As will be appreciated by one skilled in the art, when the substituent represented by L is hydrogen, the two forms co-exist in a dynamic tautomeric, equilibrium mixture. However, in the case where L represents a substitutent other than hydrogen, the two forms represent different chemical structures which do not spontaneously interconvert.

In accordance with the process employed for synthesizing the cephem intermediates and antibacterial agents of the present invention, two preparative routes are amenable. The first is illustrated as follows:

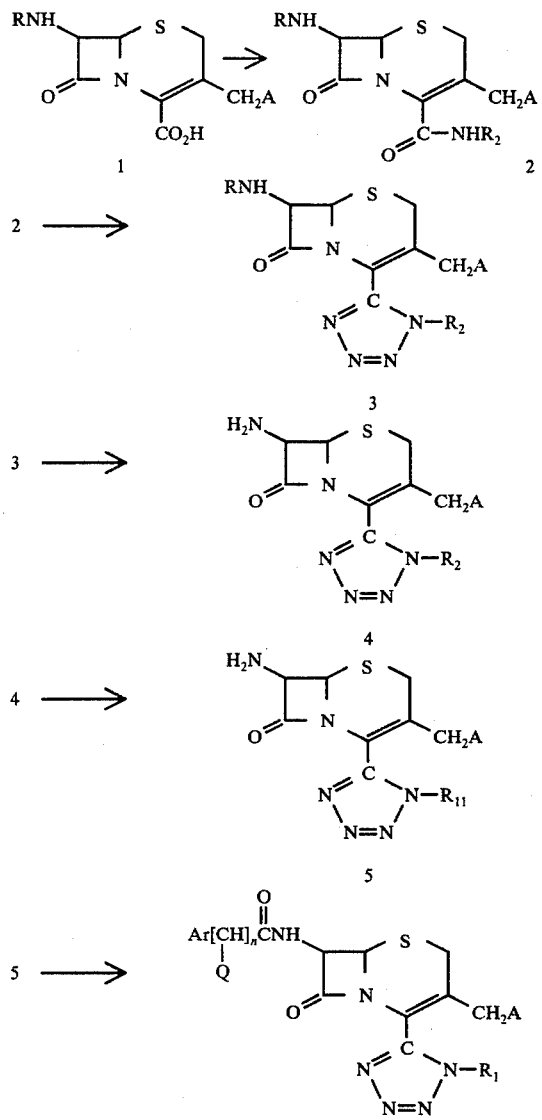

wherein R, A, $R_2$, Ar, *n* and Q are as previously defined and $R_1$ and $R_{11}$ are each hydrogen.

Experimentally, 7-carboxamido-3-substituted-Δ³-cephem-4-carboxylic acids (1), prepared by acylation of the corresponding 7-amino-cephem, are converted to the 4-carbamoyl compounds (2) by reacting the 4-carboxy moiety, activated as the 2,4-dinitrophenol ester, with an appropriate amine, $R_2NH_2$.

Preparation of compounds 2, wherein R is derived from triphenylmethyl, is achieved either by alkylation of the 7-amino compound; followed by formation of the 4-carbamoyl group as mentioned above, or by selectively removing the R acyl group of compounds of structure 2, such as removing the 2,2,2-trihaloethoxycarbonyl group using acetic acid and zinc dust, and subsequently alkylating the 7-amino-4-carboamoyl-cephem compound with the requisite triphenylmethyl chloride.

The reaction of 2 to 3 requires conversion of the 4-carbamoyl moiety of 2 to the appropriate imino chloride followed by reaction of this substrate with azide. Formation of the imino chloride is most conveniently carried out using phosgene, or phosphorous pentachloride in a reaction inert solvent such as chloroform, while reaction of the imino chloride with the salt of hydrazoic acid and tetramethylguanidine leads to the formation of the tetrazole ring. As one skilled in the art can readily appreciate, there are many sources of azide which could also be employed in this reaction including salts of hydrazoic acid with inorganic bases, such as sodium azide, lithium azide, potassium azide and ammonium azide. Because of the explosive nature of many metal azides it is advantageous, and in this case preferred, that azides formed from organic bases be employed; tetramethylguanidine hydrogen azide is particularly suited for this purpose.

The sequential step for conversion of 3 to 4 requires the removal of the "amino protecting group," R. The reaction conditions employed to affect this removal are dictated by the nature of the group to be removed. As previously mentioned, the 2,2,2-trihaloethoxycarbonyl moiety is conveniently removed using zinc dust and acetic acid; the triphenylmethyl group is removed using formic acid; and the benzoxycarbonyl moiety is removed by treating 3 with a mixture of trifluoroacetic acid/anisole (4:1; v/v) and trifluoromethylsulfonic acid. It is preferred, in this last mentioned procedure that the reaction be conducted at ice-bath temperatures (0° C.) and for a limited period of time, usually for 4-6 minutes. If higher temperatures are employed, such as 25-40° C. temperature, or longer reaction times, such as 1-3 hrs. it is possible to remove the "tetrazole blocking" group simultaneously.

Following removal of the "amino protecting" moiety, the $R_2$ variable is removed by treatment of 4 or the p-toluene sulfonic acid salt thereof with the aforementioned mixture of trifluoroacetic acid/anisole.

Acylation of 5 with the appropriate carboxylic acid activated either as an acid halide, activated ester, mixed anhydride or the acid with a carbodiimide provides for the preparation of the antibacterial compounds of the present invention.

As one skilled in the art can readily appreciate, the presence of other functional groups in the acylating acid may require that said groups be masked to prevent them from undergoing competing reactions. When the acylation is complete the groups can be unmasked.

For example, in preparing compounds of structure 6 wherein Q is amino, it is required that said amino group be blocked, preferably with a t-butoxy carbonyl group, the blocking group being removed by acid treatment after the acylation is complete. A similar practice is required wherein Q is hydroxy, in which case a formyl group is employed to mask the hydroxy group.

Compounds of structure 6 wherein Ar is bromo, n is 1 and Q is hydrogen, in addition to having antibacterial activity can be reacted with mercaptans leading to still additional antibacterial compounds.

The starting materials for the sequence of reactions are either readily available as commercial reagents or can be prepared by literature procedures. For example, the 7-amino-3-substituted-Δ³-cephem-4-carboxylic acids are reported in U.S. Pat. No. 3,641,021; the amines $R_2NH_2$ are conveniently prepared by one or more procedures as taught by Wagner and Zook, "Synthetic Organic Chemistry," John Wiley and Sons, Inc., New York, NY 1956, Chapter 24, p. 653-727; while the triphenylmethyl chlorides employed are prepared by the procedure as taught by Bachmann, *Org. Synthesis*, 23, 100 (1943).

The second procedure suitable for the synthesis of the antibacterial compounds of the present invention and the intermediates in the preparation thereof is illustrated as follows:

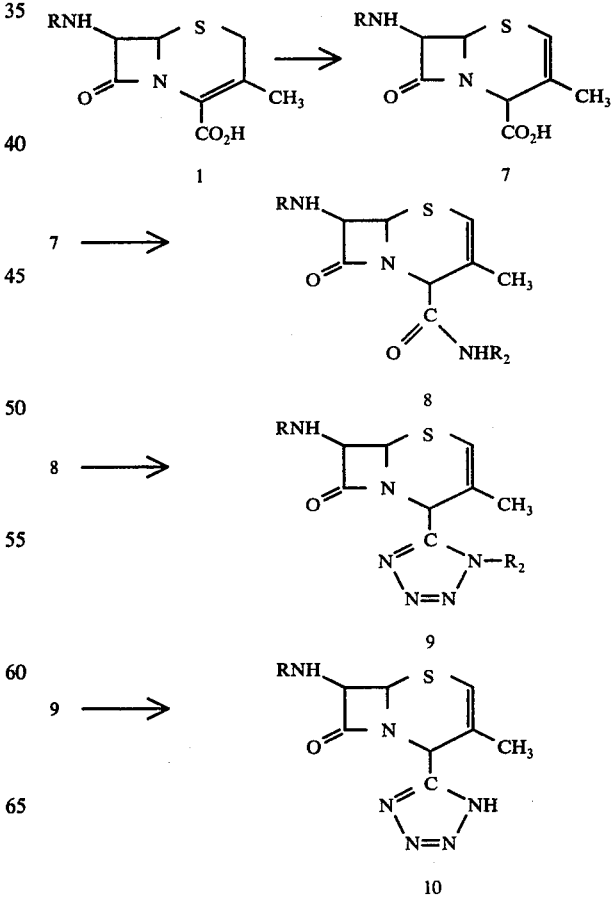

10 → 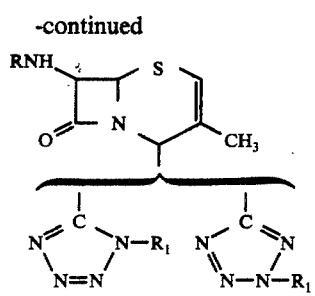

11

11 → 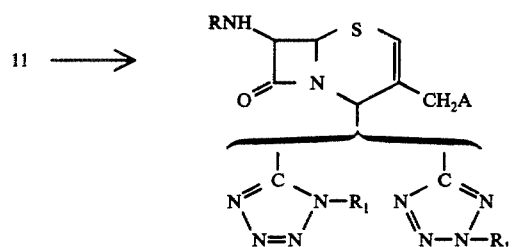

12

12 → 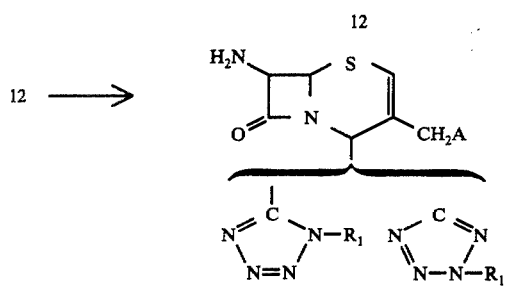

13

13 → 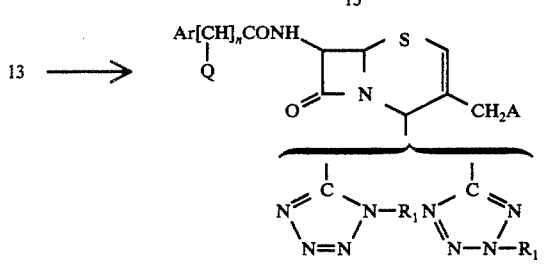

14

14 → 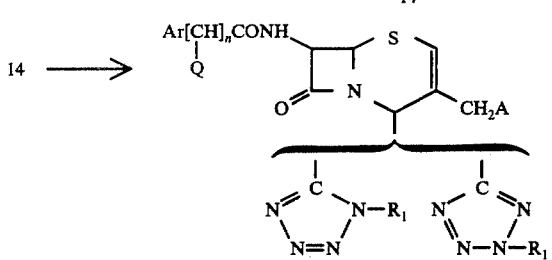

15

15 → 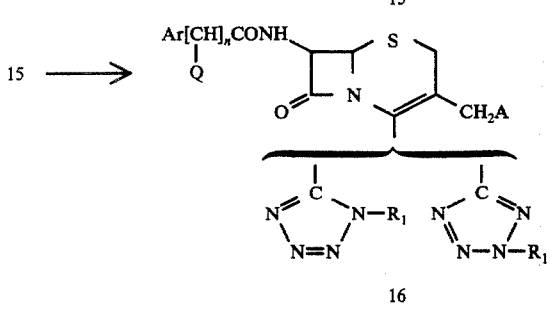

16

16 → 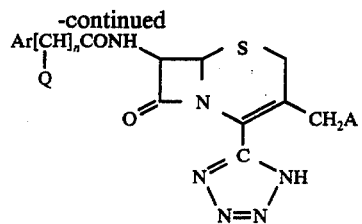

6 wherein R, A, $R_2$, Ar, n and Q are as previously indicated and $R_1$ is methoxymethyl.

In practice, the 7-acylamino-3-methyl-$\Delta^3$-cephem-4-carboxylic acid 1 is isomerized to the corresponding 7-acylamino-3-methyl-$\Delta^2$-cephem-4-carboxylic acid 7, allowing for the activation of the 3-methyl in subsequent reactions.

Preparation of the 4-carbamoyl group in compounds of structure 8 is carried out by procedures similar to those in the first synthetic sequence previously discussed.

Further, in a manner analogous to the first sequence, compounds 8 are transformed into tetrazoles of structure 9 by the same procedures involving formation of the imino chloride and its' subsequent interaction with azide.

Removal of the "tetrazole protecting" group of compounds 9 leading to 10 is affected in the manner previously discussed in the first synthetic route and comprises contacting 9 with trifluoroacetic acid/anisole at 30–50° C. for several hours.

Prior to bromination of the activated 3-methyl substituent the tetrazole of 10 is blocked by alkylation with chloromethyl methyl ether. As one skilled in the art will appreciate, alkylation can, and does, take place at both the $N_1$ and $N_2$ position, with alkylation predominating at $N_2$. Since the blocking group is removed in a later step of the sequence it is practical that the two isomers not be separated subsequent to the alkylation. Further, both isomers serve the same purpose and are equally useful in this regard.

The 3-methyl substituent of 11 is brominated with N-bromosuccinimide in the presence of a peroxide, a well known type of bromination procedure. Following the completion of the bromination, the 3-bromomethyl compound is not isolated but allowed to react with a particular nucleophilic reagent such as a mercaptan or an acetate salt giving 12.

Removal of the "amino protecting" group of 12 is carried out by methods previously discussed in the first synthetic sequence.

Similarly, acylation of 13 is affected using the aforementioned procedures, with the same consideration being given to the protection or "masking" of any functional group on the acylating acid which may compete in the acylation reaction with the 7-amino group of the $\Delta^2$-cephem (13).

Reisomerization of the $\Delta^2$ bond of 14 to the $\Delta^3$ position is achieved by oxidation of the sulfur atom of the cephem molecule with a per acid such as m-chloroperbenzoic acid giving 15. Treatment of 15 with stannous chloride and acetyl chloride results in the formation of the desired $\Delta^3$-Cephem of structure 16.

The $N_1$ and $N_2$ blocking groups are removed from 16 using trifluoroacetic acid/anisole as previously discussed and "masking" groups are removed from the acyl moiety of the 7-acylamino group if they are present.

A modification of the second reaction sequence allows for the preparation of compounds wherein $R_1$ is derived from phthalidyl, or an alkanoyloxymethyl or 1-(alkanoyloxy)ethyl moiety. The procedure leading to the preparation of these compounds utilizes the alkylation of the tetrazole moiety of 10 with an appropriate alkanoyloxymethyl halide or 1-(alkanoyloxy)ethyl halide (Ulich, et al, *J. Am. chem Soc.*, 43, 660(1921) and Euranto, et al. *Acta. Chem. Scand.*, 20, 1273 (1966) or phthalidyl halide in place of chloromethyl methyl ether. The phthalidyl, alkanoyloxymethyl and 1-(alkanoyloxy)ethyl substituted tetrazoles of the final products are pro-drug forms of the final products, and although inactive or of relatively low activity against micro organisms per se are metabolized to the free tetrazole ($R_1$=H) when injected parenterally into the animal, including man. The rate of metabolic conversion of these compounds to the free tetrazole occurs at such a rate as to provide an effective and prolonged concentration of the free tetrazole in the animal body. In effect, such compounds act as depot sources for the free tetrazole antibacterial agent. Regarding the antibacterial activity of these pro-drug forms, both the $N_1$ and the $N_2$ substituted isomers possess activity and usefulness.

If phthalidyl, alkanoyloxymethyl or 1-(alkanoyloxy)ethyl, $N_1/N_2$ substituted tetrazoles are to be synthesized by the second synthetic route, the reaction step (16!6) is omitted, and only the masking groups are removed from the acyl portion of the side chain.

Alternate methods exists for the synthesis of those antibacterial products bearing a phthalidyl, alkanoyloxymethyl of 1-(alkanoyloxy)ethyl group at the $N_1/N_2$ position of the tetrazole moiety. One method embraces alkylation of the base salt of an appropriate 7-amino-3-substituted-4-(tetrazol-5-yl)-$\Delta^3$-cephem followed by acylation of the 7-amino group as previously discussed. The second method utilizes alkylation of the base salt of an appropriate 7-acylamino-3-substituted-4-(tetrazol-5-yl)-$\Delta^3$-cephem; both methods including the removal of "masking" groups from the side chain, if necessary.

Regarding this second series of reactions leading to the intermediates and final product of the present invention, the preferred "aminoblocking" groups are the 2,2,2-trihaloethoxycarbonyl moieties.

As has been previously noted, a characteristic feature of the acidic compounds of the instant invention, those wherein $R_1$ or $R_{11}$ are H or Q is carboxy, is their ability to form basic salts. Acid congeners of the present invention are converted to basic salts by the interaction of said acid with an appropriate base in an aqueous or nonaqueous medium. Such basic reagents suitably employed in the preparation of said salts can vary in nature, and are meant to contemplate such bases as organic amines, ammonia, alkali metal hydroxides, carbonates, bicarbonates, hydrides and alkoxides, as well as alkali earth metal hydroxides, hydrides, alkoxides and carbonates. Representative of such bases are ammonia, primary amines such as n-propylamine, n-butylamine, aniline, cyclohexylamine, benzylamine, p-toluidine, ethylamine, octylamine, secondary amines such as dicyclohexylamine and tertiary amines such as diethylaniline, N-methylpyrrolidine, N-methylmorpholine and 1,5-diazabicyclo-[4,3,0]-5-nonene; sodium hydroxide, potassium hydroxide, ammonium hydroxide, sodium ethoxide, potassium methoxide, magnesium hydroxide, calcium hydride and barium hydroxide.

As one skilled in the art can readily appreciate, some compounds of the instant invention are sufficiently basic, by virtue of those final products wherein Q is amino, to form acid addition salts; said salts, especially the pharmaceutically acceptable acid addition salts, are also considered within the scope of this invention.

In addition, those useful intermediates of the present invention which contain a free 7-amino moiety or a free tetrazole ($R_1$, $R_{11}$=H) are also capable of forming acid addition salts and base salts, respectively. These salts are useful either in the characterization of these intermediates, such as the acid addition salts, or are utilized in reactions, such as alkylation of the base salt of the tetrazoles.

In utilization of the chemotherapeutic activity of those compounds of the present invention which form basic salts, it is preferred, of course, to use pharmaceutically acceptable salts. Although water insolubility, high toxicity, or lack of crystalline nature may make some salt species unsuitable or less desirable for use as such in a given pharmaceutical application, the water insoluble or toxic salts can be converted to the corresponding acids by decomposition of the salts, or alternately they can be converted to any desired pharmaceutically acceptable basic salt. The said pharmaceutically acceptable salts preferred include the sodium, aluminum, potassium, calcium, magnesium, ammonium, and substituted ammonium salts, e.g., procaine, dibenzylamine, N,N-bis(dehydroabietyl)ethylenediamine, 1-ephenamine, N-ethylpiperidine, N-benzyl$\beta$-phenthylamine, N,N'-dibenzylethylenediamine, triethylamine, as well as salts with other amines which have been used to form salts with cephems.

The novel cephems described herein exhibit in vitro activity against a variety of micro-organisms, including both gram-positive and gram-negative bacteria. Their useful activity can readily be demonstrated by in vitro tests against various organisms in a brain-heart infusion medium by the usual twofold serial dilution technique. The in vitro activity of the herein described compounds renders them useful for topical application in the form of ointments, creams, and the like, or for sterilization purposes, e.g., sick-room utensils.

These novel cephems are also effective antibacterial agents in vivo in animals, including man, not only via the parenteral route of administration but also by the oral route of administration.

Obviously, the physician will ultimately determine the dosage which will be most suitable for a particular individual person, and it will vary with the age, weight, and response of the particular patient as well as with the nature and extent of the symptoms, the nature of the bacterial infection being treated nd the pharmacodynamic characteristics of the particular agent to be administered. It will often be found that when the composition is administered orally, larger quantities of the active ingredient will be required to produce the same level as produced by a smaller quantity administered parenterally.

Having full regard for the foregoing factors it is considered that an effective daily oral dose of the compounds of the present invention in humans of approximately 50–1000 mg./kg. per day, with a preferred range of about 250–750 mg./kg. per day in single or divided doses, and a parenteral does of 25–500 mg./kg. per day, with a preferred range of about 125–400 mg./kg. per day will effectively alleviate the symptoms of the infection. These values are illustrative, and there may, of course, be individual cases where higher or lower dose ranges are merited.

The preferred compounds of the present invention which are useful as intermediates are 7-(2',2',2'-trichloroethoxycarboxamido)-3-methyl-4-[N-(p-methoxybenzyl)carbamoyl]-Δ³-cephem, 7-(benzyloxycarboxamido)-3-methyl- -[N-(p-methoxybenzyl)carbamoyl]-Δ³-cephem, 7-(n-triphenylmethylamino)-3-methyl-4-[N-(p-methoxybenzyl)carbamoyl]-Δ³-cephem, 7-(2',2',2'-trichloroethoxycarboxamido)-3-acetoxymethyl-4-[N-(p-methyoxybenzyl)carbamoyl]-Δ³-cephem, 7-(benzyloxycarboxamido)-3-acetoxymethyl-4-[N-(p-methoxybenzyl)carbamoyl]-Δ³-cephem, 7-(N-triphenylmethylamino)-3-acetoxymethyl-4-[N-(p-methoxybenzyl)-carbamoyl]-Δ³-cephem, 7-(2',2',2'-trichloroethyoxycarboxamido)-3-methyl-4-[N(p-methoxybenzyl)carbamoyl]-Δ²-cephem, 7-(2',2',2'-trichloroethoxycarboxamido)-3-methyl-4-[1-(p-methoxybenzyl)tetrazol-5-yl]-Δ³-cephem, 7-(N-triphenylamino)-3-methyl-4-[1-(p-methoxybenzyl)tetrazol-5-yl]-Δ³-cephem, 7-amino-3-methyl-4-[1-(p-methoxybenzyl)tetrazol-5-yl]-Δ³-cephem, 7-(benzyloxycarboxamido)-3-acetoxymethyl-4-[1-(p-methoxybenzyl)tetrazol-5-yl]-Δhu 3-cephem, 7-(2',2',2'-trichloroethoxycarboxamido)-3-acetoxymethyl-4-[1-(p-methoxybenzyl)tetrazol-5-yl]-Δ³-cephem, 7-amino-3-acetoxymethyl-4-[1-(p-methoxybenzyl)tetrazol-5-yl]-Δ³-cephem, 7-(benzyloxycarboxamido)-3-(1-methyltetrazol-5-ylthiomethyl)-4-[1-(p-methoxybenzyl)tetrazol-5-yl]-Δ³-cephem, 7-(2',2',2'-trichloroethoxycarboxamido)-3-(2-methyl-1,3,4-thiadiazol-5-ylthiomethyl)-4-[1-(p-methoxybenzyl)tetrazol-5-yl]-Δ³-cephem, 7-amino-3-(2-methyl-1,3,4-thiadiazol-5-ylthiomethyl)-4-[1-(p-methoxybenzyl)tetrazol-5-yl-Δ³-cephem, 7-(2',2',2'-trichloroethoxycarboxamido)-3-methyl-4-[1-(p-methoxybenzyl)tetrazol-5-yl]-Δ²-cephem, 7-(benzyloxycarboxamido)-3-(2-methyl-1,3,4-thiadiazol-5-ylthiomethyl)-4-[1-(p-methoxybenzyl)tetrazol-5-yl]-Δ³-cephem, 7-amino-3-methyl-4-(tetrazol-5-yl)-Δ³-cephem, 7-amino-3-acetoxymethyl-4-(tetrazol-5-yl)-Δ³-cephem, 7-amino-3-(2-methyl-1,3,4-thiadiazol-5-ylthiomethyl)-4-(tetrazol-5-yl)-Δ³-cephem, 7-amino-3-(1-methyltetrazol-5-ylthiomethyl)-4-(tetrazol-5-yl)-Δ³-cephem, 7-(2',2',2'-trichloroethoxycarboxamido)-3-methyl-4-(tetrazol-5-yl)-Δ²-cephem, 7-(2',2',2'-trichloroethoxycarboxamido)-3-methyl-4-[1-(methoxymethyl)tetrazol-5-yl]-Δ²-cephem, b 7-(2',2',2'-trichloroethoxycarboxamido)-3-methyl-4-[2-(methoxymethyl)tetrazol-5-yl]-Δ²-cephem, 7-amino-3-methyl-4-[1-(methoxymethyl)tetrazol-5-yl]-Δ²-cephem, 7-amino-3-methyl-4-[2-(methoxymethyl)tetrazol-5-yl]-Δ²-cephem, 7-amino-3-acetoxymethyl-4-[1-(methoxymethyl)tetrazol-5-yl]-Δ²-cephem, 7-amino-3-acetoxymethyl-4-[1-(methoxymethyl)tetrazol-5-yl]-Δ²-cephem, 7-amino-3-(1-methyltetrazol-5-ylthiomethyl)-4-[1-(methoxymethyl)tetrazol-5-yl]-Δ²-cephem, 7-amino-3-(1-methyltetrazol-5-ylthiomethyl)-4-[2-(methoxymethyl)tetrazol-5-yl]-Δ²-cephem, 7-amino-3-(2-methyl-1,3,4-thiadiazol-5-ylthiomethyl)-4-[1-methoxymethyl)tetrazol-5-yl]-Δ²-cephem, 7-amino-3-(2-methyl-1,3,4-thiadiazol-5-ylthiomethyl)-4-[2-(methoxymethyl)tetrazol-5-yl]-Δ²-cephem, 7-(2',2',2'-trichloroethoxycarboxamido)-3-bromomethyl-4-[1-methoxymethyl)tetrazol-5-yl]-Δ²-cephem and 7-(2',2',2'-trichloroethoxycarboxamido)-3-bromomethyl-4-[2-(methoxymethyl)tetrazol-5-yl]-Δ²-cephem.

The preferred antibacterial agents of the present invention are 7-phenylacetamido-3-methyl-4-(tetrazol-5-yl)-Δ³-cephem, 7-phenoxyacetamido-3-methyl-4-(tetrazol-5-yl)-Δ³-cephem, 7-(2-thienylacetamido)-3-methyl-4l -(tetrazol-5-yl)-Δ³-cephem, 7-phenylacetamido-3-methyl-4-[2-pivaloyloxymethyl)tetrazol-5-yl]-Δ³-cephem, 7-phenoxyacetamido-3-methyl-4-[2-(pivaloyloxymethyl)tetrazol-5-yl]-Δ³-cephem and 7-(2-thienylacetamido)-3-methyl-4-[2-(pivaloyoxymethyl)-tetrazol-5-yl]-Δ³-cephem.

The antimicrobial data of a number of compounds of the instant invention against *Streptomyces pyogenes* are provided in the following table. The tests were run under standardized conditions in which nutrient broth containing various concentrations of the test material was seeded with the particular organism specified, and the minimum concentration (MIC) at which growth of each organism failed to occur was observed and recorded.

TABLE I

| $R^1$ | A | In vitro MIC (mcg./ml.) |
|---|---|---|
| $C_6H_5CH_2-$ | H | 0.78 |
| $C_6H_5OCH_2-$ | H | 3.1 |
| [thiophene]-$CH_2-$ | H | 0.4 |
| $HC{=}N-CH_2-$ (triazole) | H | 6.2 |
| D-$C_6H_5CH(OH)-$ | H | 1.5 |
| D-4-$HOC_6H_4CH(NH_2)-$ | H | 1.5 |
| $C_6H_5CH(N_3)-$ | H | 1.5 |
| [thiadiazole-$CH_3$]-$SCH_2-$ | H | 0.78 |
| D-$C_6H_5CH(OH)-$ | $-S-$[tetrazole-$CH_3$] | 3.12 |
| [thiophene]-$CH_2$ | $OCOCH_3$ | 1.6 |
| [thiophene]-$CH_2$ | $-S-$[tetrazole-$CH_3$] | 0.1 |

The novel antibacterial agents of the present invention remarkably effective in treating a number of infections caused by susceptible gram-negative and gram-positive bacteria in poultry and animals including man. For such purposes, the pure materials or mixtures thereof with other antibiotics can be employed. They may be administered alone or in combination with a pharmaceutical carrier on the basis of the chosen route of administration and standard pharmaceuticl practice. For example, they may be administered orally in the form of tablets containing such excipients as starch, milk sugar, certain types of clay, etc., or in capsules alone or in admixture with the same or equivalent excepients. They may also be administered orally in the form of elixirs or orall suspensions which may contain flavoring or coloring agents, or be injected parenterally, that is, intramuscularly or subcutaneously. For parental administration, they are best used in the form of a sterile aqueous solution which may be either aqueous such as water, isotonic slaine, isotonic dextrose, Ringer's solution, or non-aqueous such as fatty oils of vegetable origin (cotton seed, peanut oil, corn, sesame) and other non-aqueous vehicles which will not interfere with the therapeutic effieiency of the preparation and are nontoxic in the volume or proportion used (glycerol, propylene glycol, sorbitol). Additionally, compositions suitable for extemporaneous preparation of solutions prior to administration may advantageously be made. Such compositions may include liquid diluents, for example, propylene glycol, diethyl carbonate, glycerol, sorbitol, etc.; buffering agents, as well as local anestetics and inorganic salts to afford desirable pharmacological properties.

The following examples are provided solely for the purpose of further illustration. Infrared (IR) spectra are measured as potassium bromide discs (KBr discs) or as Nujol mulls, and diagnostic absorption bands are reported in wave numbers (cm$^{-1}$). Nuclear magnetic resonance spectra (NMR) are measured at 60 MHz for solutions in deuterochloroform (CDCl$_3$), perdeutero dimethyl sulfoxide (DMSO-d$_6$) or deuterium oxide (D$_2$O), and peak positions are expressed in parts per million (ppm) downfield from tetramethylsilane or sodium 2,2-dimethyl-2-silapentane-5-sulfonate. The following abbreviations for peak shapes are used: s, singlet; d, doublet, t, triplet; q, quartet; m, multiplet.

EXAMPLE 1

7-(2',2',2'-Trichloroethoxycarboxamido)-3-methyl-4-[N-(p-methoxybenzyl)carbamoyl]-Δ$^3$-cephem A.
7-(2',2',2'-Trichloroethoxycarboxamido)-3-methyl-Δ$^3$-cephem-4-carboxylic acid To a suspension of 555 g. of 7-amino-3-methyl-Δ$^3$-cephem-4-carboxylic acid in 16.65 l. of 1:2 acetone/water solution is added 600 g. of sodium bicarbonate and the mixture allowed to stir at room temperature for 30 min. To the resulting solution is added, over a 45 min. period, 600 g. of 2,2,2-trichloroethoxycarbonyl chloride, and the reactionmixture allowed to stir for an additional 18 hrs. The mixture is extracted with methylene chloride and the aqueous layer separated and acidified to pH 2 with 5N hydrochloric acid. The acidified aqueous is extracted with fressh methylene chloride (3 × 1.5 l. and 2 × 500 ml.) and the combined organic layers washed successivly with 5N hydrochloric acid (2 × 500 ml.) and water (3 × 500 ml.), and dried over magnesium sulfate. The thick oil, which remains after the solvent is removed in vacuo, is dissolved in 2 l. of diethyl ether and added dropwise to 1.5 l. of petroleum ether. The intermediate poduct slowly crystallizes from solution (70% yield).

NMR (DMSOd$_6$): δ = 5.4 (q) 1H; 5.1 (d) 1H; 4.85 (s) 1H; 3.42 (s) 2H; 2.0 (s) 3H.

IR (KBr disc) γ max: 1770 cm$^{-1}$ (β-lactam carbonyl).

The product is stored in a dioxane solution for use in subsequent reactions without further purification. B. 7-(2',2',2'-Trichloroethoxycarboxamido)-3-methyl-4-[N-(p-methoxybenzyl)-carbamoyl]-Δ$^3$-cephem.

A solution containing 1.84 g. of 2,4-dinitrophenol in 35 ml. of methylene chloride is treated with 4 g. of 7-(2',2',2'-trichloroethoxycarboxamido)-3-methyl-Δ$^3$-cephem-4-carbaoxylic acid in a minimum amount of dioxane followed by a solution of 2.1 g. of dicyclohexyl carbodiimide in 20 ml. of methylene chloride. After allowing the reaction mixture to stir for 30 min. at room temperature, the dicyclohexyl urea is filtered, washed with methylene chloride,and the filtrate and washings combined and treated with 1.4 g. of p-methoxybenzylamine in 14 ml. of methylene chloride.

After 30 min. at room temperature, the reaction mixture is washed with a saturated sodium carbonate solution and the organic phase dried over magnesium sulfate. The thick oil, which remains after the solvent is removed under reduced pressure, is triturated with petroleum ether. The cyrstallized product is filtered and dried to give 4.0 g. of a pale yellow solid.

NMR (DMSOd$_6$): δ = 8.5 (t) 1H; 7.0 (q) 4H; 5.3 (q) and 4.95 (d) 2H; 4.8 (s) 2H; 4.3 (d) 2H; 3.7 (s) 3H; 3.45 (broad) 2H and 2 (s) 3H. IR (KBr disc) γ: 1770 cm$^{-1}$ (β-lactam carbonyl).

EXAMPLE 2

Starting with the appropriate amine and requisite 7-amino-b 3-methyl-Δ$^3$-cephem-4-carboxylic acid, and utilizing the procedure of Exmple 1, the following 7-acylamino-3-methyl-4-(N-substitutedcarbamoyl)-Δ$^3$-cephems are synthesized:

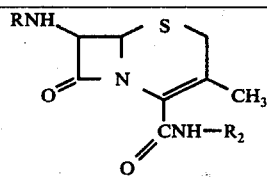

| R | R$_2$ |
|---|---|
| Cl$_3$CCH$_2$OCO— | 4-C$_6$H$_5$CH$_2$OC$_6$H$_4$CH$_2$— |
| Cl$_3$CCH$_2$OCO— | 4-C$_6$H$_5$CH$_2$O-3-FC$_6$H$_3$CH$_2$— |
| Cl$_3$CCH$_2$OCO— | 2-Cl-4-CH$_3$OC$_6$H$_3$CH$_2$— |
| Cl$_3$CCH$_2$OCO— | 3-Cl-4-HOC$_6$H$_3$CH$_2$— |
| Cl$_3$CCH$_2$OCO— | 3,4-(CH$_3$O)$_2$C$_6$H$_3$CH$_2$— |
| Cl$_3$CCH$_2$OCO— | 4-HOC$_6$H$_4$CH(CH$_3$)— |
| Cl$_3$CCH$_2$OCO— | 2-Br-4-CH$_3$OC$_6$H$_3$CH$_2$— |
| Cl$_3$CCH$_2$OCO— | 4-CH$_3$OC$_6$H$_4$CH(φ)— |
| Cl$_3$CCH$_2$OCO— | 2,4-(CH$_3$O)$_2$C$_6$H$_3$CH(CH$_3$)— |
| Cl$_3$CCH$_2$OCO— | 4-CH$_3$OC$_6$H$_4$CH(n-C$_3$H$_7$)— |
| Cl$_3$CCH$_2$OCO— | 3-CH$_3$-4-CH$_3$OC$_6$H$_3$CH$_2$— |
| Cl$_3$CCH$_2$OCO— | 4-C$_2$H$_5$CO$_2$C$_6$H$_4$CH$_2$— |
| Cl$_3$CCH$_2$OCo— | 3-F-4-CH$_3$CO$_2$C$_6$H$_3$CH$_2$— |
| Cl$_3$CCH$_2$OCO— | 4-HOC$_6$H$_4$CH(φ)— |
| Cl$_3$CCH$_2$OCO— | 3-I-4-CH$_3$OC$_6$H$_3$CH$_2$— |
| Cl$_3$CCH$_2$OCO— | 4-(i-C$_3$H$_7$CO$_2$)$_6$H$_4$CH$_2$— |
| Cl$_3$CCH$_2$OCO— | 3,4-(C$_6$H$_5$CH$_2$O)$_2$C$_6$H$_3$CH$_2$— |
| Cl$_3$CCH$_2$OCO— | 4-CH$_3$OC$_6$H$_4$CH(CH$_3$)— |
| Cl$_3$CCH$_2$OCO— | 4-CH$_3$OC$_6$H$_4$CH(C$_2$H$_5$)— |
| Cl$_2$CCH$_2$OCO— | 3-F-4-CH$_3$OC$_6$H$_3$CH$_2$— |
| Cl$_3$CCH$_2$OCO— | 3-Cl-4-CH$_3$OC$_6$H$_3$CH(CH$_3$)— |
| Cl$_3$CCH$_2$OCO— | 4-HOC$_6$H$_4$CH$_2$— |
| Cl$_3$CCH$_2$OCO— | 4-CH$_3$CO$_2$C$_6$H$_4$CH$_2$— |
| Cl$_3$CCH$_2$OCO— | 3-F-4-HOC$_6$H$_3$CH$_2$— |
| Cl$_3$CCH$_2$OCO— | 3-CH$_3$O-4-CH$_3$CO$_2$C$_6$H$_4$CH$_2$— |
| Cl$_3$CCH$_2$OCO— | 4-C$_6$H$_5$CH$_2$OC$_6$H$_3$CH(CH$_3$)— |
| Cl$_3$CCH$_2$OCO— | 3-Cl-4-C$_6$H$_5$CH$_2$OC$_6$H$_3$CH$_2$— |
| Cl$_3$CCH$_2$OCO— | 3,4-(C$_2$H$_5$CO$_2$)$_2$C$_6$H$_3$CH$_2$— |
| Cl$_3$CCH$_2$OCO— | 4-(n-C$_3$H$_7$CO$_2$)C$_6$H$_4$CH$_2$— |
| Cl$_3$CCH$_2$OCO— | 4-(i-C$_3$H$_7$CO$_2$)C$_6$H$_4$CH(C$_2$H$_5$)— |
| Cl$_3$CCH$_2$OCO— | 2-furylmethyl- |
| Cl$_3$CCH$_2$OCO— | 5-methyl-2-furylmethyl- |
| Cl$_3$CCH$_2$OCO— | 2-thienylmethyl- |
| Cl$_3$CCH$_2$OCO— | 5-methyl-2-thienylmethyl- |

-continued

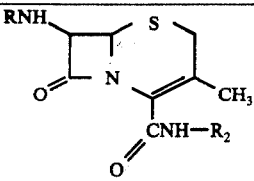

| R | R₂ |
|---|---|
| Cl₃CCH₂OCO— | 1-(2-furyl)ethyl- |
| Cl₃CCH₂OCO— | 1-(5-methyl-2-furyl)ethyl- |
| Br₃CCH₂OCO— | 4-C₆H₅CH₂OC₆H₄CH₂— |
| Br₃CCH₂OCO— | 4-C₆H₅CH₂O-3-FC₆H₃CH₂— |
| Br₃CCH₂OCO— | 2-Cl-4-CH₃OC₆H₃CH₂— |
| Br₃CCH₂OCO— | 3-Cl-4-HOC₆H₃CH₂— |
| Br₃CCH₂OCO— | 2-Br-4-CH₃OC₆H₃CH₂— |
| Br₃CCH₂OCO— | 2,4-(CH₃O)₂C₆H₃CH(CH₃)— |
| Br₃CCH₂OCO— | 4-C₂H₅CO₂C₆H₄CH₂— |
| Br₃CCH₂OCO— | 3-CH₃-4-CH₃OC₆H₃CH₂— |
| Br₃CCH₂OCO— | 3-F-4-CH₃CO₂C₆H₃CH₂— |
| Br₃CCH₂OCO— | 3-I-4-CH₃OC₆H₃CH₂— |
| Br₃CCH₂OCO— | 4-(i-C₃H₇CO₂)C₆H₄CH₂— |
| Br₃CCH₂OCO— | 3,4-(C₆H₅CH₂O)₂C₆H₃CH₂— |
| Br₃CCH₂OCO— | 4-CH₃OC₆H₄CH(CH₃)— |
| Br₃CCH₂OCO— | 4-CH₃OC₆H₄CH(C₂H₅)— |
| Br₃CCH₂OCO— | 3,4-(CH₃O)₂C₆H₃CH₂— |
| Br₃CCH₂OCO— | 3-F-4-CH₃OC₆H₃CH₂— |
| Br₃CCH₂OCO— | 3-Cl-4-CH₃OC₆H₃CH(CH₃)— |
| Br₃CCH₂OCO— | 4-HOC₆H₄CH₂— |
| Br₃CCH₂OCO— | 4-HOC₆H₄CH(CH₃)— |
| Br₃CCH₂OCO— | 4-CH₃CO₂C₆H₄CH₂— |
| Br₃CCH₂OCO— | 3-Cl-4-HOC₆H₃CH₂— |
| Br₃CCH₂OCO— | 3-Cl-4-CH₃CO₂C₆H₃CH₂— |
| Br₃CCH₂OCO— | 4-C₆H₅CH₂OC₆H₃CH(CH₃)— |
| Br₃CCH₂OCO— | 3-Cl-4-C₆H₅CH₂OC₆H₃CH₂— |
| Br₃CCH₂OCO— | 2-F-4-HOC₆H₃CH₂— |
| Br₃CCH₂OCO— | 3,4-(C₂H₅CO₂)₂C₆H₃CH₂— |
| Br₃CCH₂OCO— | 4-(n-C₃H₇CO₂)C₆H₄CH₂— |
| Br₃CCH₂OCO— | 2-furylmethyl- |
| Br₃CCH₂OCO— | 5-methyl-2-furylmethyl- |
| Br₃CCH₂OCO— | 2-thienylmethyl- |
| Br₃CCH₂OCO— | 1-(2-furyl)ethyl- |
| Br₃CCH₂OCO— | 1-(5-methyl-2-furyl)ethyl- |

EXAMPLE 3

7-(2',2',2'-Trichloroethoxycarboxamido)-3-methyl-4-[1-p-methoxybenzyltetrazol]-5-yl-Δ³-cephem To a suspension of 100 g. of 7-(2',2',2'-trichloroethoxycarboxamido)-3-methyl-4-[N-(p-methoxybenzyl)carbamoyl]-Δ³-cephem in 2 L. of chloroform is added dropwise 250 ml. of toluene containing 30 g. of phosgene over a 15 min. period. After a further 15 min. a solution of 24 g. of dry pyridine in 100 ml. of chloroforme is added dropwise over 45 min., during which a solution is effected and carbon dioxide is slowly evolved. The solution is stirred for 90 min., and is subsequently concentrated to half volume in vacuo to remove the excess phosgene. Chloroform (2.1) is added, and to the stirred solutin is then added 45 g. of tetramethyl guanidinium azide in 250 ml. of chloroform. After 2 hrs., the chloroform solutin is washed successively with water (2 × 500 ml.), saturated sodium carbonate solution (2 × 300 ml.), 2.5N hydrochloric acid and water (1 × 250 ml.). The organic phase is dried over magnesium sulfate and concentrated in vacuo to a gummy solid, 102 g. The product is further purified by chromatographing on a column of alumina (306 g.) using chloroform as the solvent (408ml.) and eluate (1.5 l.). The eluate is added with stirring to 6 l. of petroleum ether, resulting in the precipitation of the product as a light brown solid, 79 g.

NMR (CDCl₃): δ = 6.9 (q) 4H; 5.4 (m) 3H; 4.9 (d) 1H; 4.7 (s) 2H; 3.7 (s) 3H; 3.3 (q) 3H; and 1.4 (s) 3H.

IR KBr disc) γ: 1770 cm⁻¹ (β-lactam carabonyl).

In a similar manner, 250 mg. of 7-(2',2',2'-trichloreothoxycarboxamido)-3-methyl-[N-(p-methoxybenzyl)-carbamoyl]-Δ³-cephem, 0.007 ml. of pyridine and 2.6 mg. of phosphorous pentachloride in 6 ml. of chloroform yield the corresponding imino chloride, which on treatment with tetramethyl guanidinium azide (1 g.) in 2 ml. of chloroform gave 220 mg. of the desired tetrazole, identical in all respects with that obtained above.

EXAMPLE 4

Utilizing the intermediate amides of Example 2, and employing the procedure of Example 3, the following tetrazole derivatives are synthesized:

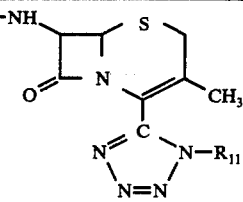

| R | R₁₁ |
|---|---|
| Cl₃CCH₂OCO— | 4-C₆H₅CH₂OC₆H₄CH₂— |
| Cl₃CCH₂OCO— | 4-C₆H₅CH₂O-3-FC₆H₃CH₂— |
| Cl₃CCH₂OCO— | 2-Cl-4-CH₃OC₆H₃CH₂— |
| Cl₃CCH₂OCO— | 3-Cl-4-HOC₆H₃CH₂— |
| Cl₃CCH₂OCO— | 3,4-(CH₃O)₂C₆H₃CH₂— |
| Cl₃CCH₂OCO— | 4-HOC₆H₄CH(CH₃)— |
| Cl₃CCH₂OCO— | 2-Br-4-CH₃OC₆H₃CH₂— |
| Cl₃CCH₂OCO— | 4-CH₃OC₆H₄CH(φ)— |
| Cl₃CCH₂OCO— | 2,4-(CH₃O)₂C₆H₃CH(CH₃)— |
| Cl₃CCH₂OCO— | 4-CH₃OC₆H₄CH(n-C₃H₇)— |
| Cl₃CCH₂OCO— | 3-CH₃-4-CH₃OC₆H₃CH₂— |
| Cl₃CCH₂OCO— | 4-C₂H₅CO₂C₆H₄CH₂— |
| Cl₃CCH₂OCO— | 3-F-4-CH₃CO₂C₆H₃CH₂— |
| Cl₃CCH₂OCO— | 4-HOC₆H₄CH(φ)— |
| Cl₃CCH₂OCO— | 3-I-4-CH₃OC₆H₃CH₂— |
| Cl₃CCH₂OCO— | 4-(i-C₃H₇CO₂)C₆H₄CH₂— |
| Cl₃CCH₂OCO— | 3,4-(C₆H₅CH₂O)₂C₆H₃CH₂— |
| Cl₃CCH₂OCO— | 4-CH₃OC₆H₄CH(CH₃)— |
| Cl₃CCH₂OCO— | 4-CH₃OC₆H₄CH(C₂H₅)— |
| Cl₃CCH₂OCO— | 3-F-4-CH₃OC₆H₃CH₂— |
| Cl₃CCH₂OCO— | 3-Cl-4-CH₃OC₆H₃CH(CH₃)— |
| Cl₃CCH₂OCO— | 4-HOC₆H₄CH₂— |
| Cl₃CCH₂OCO— | 4-CH₃CO₂C₆H₄CH₂— |
| Cl₃CCH₂OCO— | 3-F-4-HOC₆H₃CH₂— |
| Cl₃CCH₂OCO— | 3-CH₃O-4-CH₃CO₂C₆H₄CH₂— |
| Cl₃CCH₂OCO— | 4-C₆H₅CH₂OC₆H₃CH(CH₃)— |
| Cl₃CCH₂OCO— | 3-Cl-4-C₆H₅CH₂OC₆H₃CH₂— |
| Cl₃CCH₂OCO— | 3,4-(C₂H₅CO₂)₂C₆H₃CH₂— |
| Cl₃CCH₂OCO— | 4-(n-C₃H₇CO₂)C₆H₄CH₂— |
| Cl₃CCH₂OCO— | 4-(i-C₃H₇CO₂)C₆H₄CH(C₂H₅)— |
| Cl₃CCH₂OCO— | 2-furylmethyl- |
| Cl₃CCH₂OCO— | 5-methyl-2-furylmethyl- |
| Cl₃CCH₂OCO— | 2-thienylmethyl- |
| Cl₃CCH₂OCO— | 5-methyl-2-thienylmethyl- |
| Cl₃CCH₂OCO— | 1-(2-furyl)ethyl- |
| Cl₃CCH₂OCO— | 1-(5-methyl-2-furyl)ethyl- |
| Br₃CCH₂OCO— | 4-C₆H₅CH₂OC₆H₄CH₂— |
| Br₃CCH₂OCO— | 4-C₆H₅CH₂O-3-FC₆H₃CH₂— |
| Br₃CCH₂OCO— | 2-Cl-4-CH₃OC₆H₃CH₂— |
| Br₃CCH₂OCO— | 4-Cl-4-HOC₆H₃CH₂— |
| Br₃CCH₂OCO— | 2-Br-4-CH₃OC₆H₃CH₂— |
| Br₃CCH₂OCO— | 2,4-(CH₃O)₂C₆H₃CH(CH₃)— |
| Br₃CCH₂OCO— | 4-C₂H₅CO₂C₆H₄CH₂— |
| Br₃CCH₂OCO— | 3-CH₃-4-CH₃OC₆H₃CH₂— |
| Br₃CCH₂OCO— | 3-F-4-CH₃CO₂C₆H₃CH₂— |
| Br₃CCH₂OCO— | 3-I-4-CH₃OC₆H₃CH₂— |
| Br₃CCH₂OCO— | 4-(i-C₃H₇CO₂)C₆H₄CH₂— |
| Br₃CCH₂OCO— | 3,4-(C₆H₅CH₂O)₂C₆H₃CH₂— |
| Br₃CCH₂OCO— | 4-CH₃OC₆H₄CH(CH₃)— |
| Br₃CCH₂OCO— | 4-CH₃OC₆H₄CH(C₂H₅)— |
| Br₃CCH₂OCO— | 3,4-(CH₃O)₂C₆H₃CH₂— |
| Br₃CCH₂OCO— | 3-F-4-CH₃OC₆H₃CH₂— |
| Br₃CCH₂OCO— | 3-Cl-4-CH₃OC₆H₃CH(CH₃)— |
| Br₃CCH₂OCO— | 3-Cl-4-CH₃OC₆H₃CH(CH₃)— |
| Br₃CCH₂OCO— | 4-HOC₆H₄CH₂— |
| Br₃CCH₂OCO— | 4-HOC₆H₄CH(CH₃)— |
| Br₃CCH₂OCO— | 4-CH₃CO₂C₆H₄CH₂— |
| Br₃CCH₂OCO— | 3-Cl-4-HOC₆H₃CH₂— |
| Br₃CCH₂OCO— | 3-Cl-4-CH₃CO₂C₆H₃CH₂— |
| Br₃CCH₂OCO— | 4-C₆H₅CH₂OC₆H₃CH(CH₃)— |
| Br₃CCH₂OCO— | 3-Cl-4-C₆H₅CH₂OC₆H₃CH₂— |
| Br₃CCH₂OCO— | 2-F-4-C₆H₅CH₂OC₆H₃CH₂ |
| Br₃CCH₂OCO— | 3,4-(C₂H₅CO₂)₂C₆H₃CH₂— |
| Br₃CCH₂OCO— | 4-(n-C₃H₇CO₂)C₆H₄CH₂— |
| Br₃CCH₂OCO— | 2-furylmethyl- |

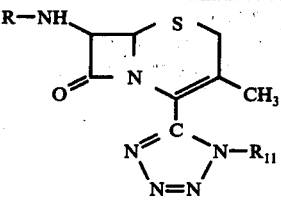

| R | R₁₁ |
|---|---|
| Br₃CCH₂OCO— | 5-methyl-2-furylmethyl- |
| Br₃CCH₂OCO— | 2-thienylmethyl- |
| Br₃CCH₂OCO— | 1-(2-furyl)ethyl- |
| Br₃CCH₂OCO— | 1-(5-methyl-2-furyl)ethyl- |

EXAMPLE 5

7-Amino-3-methyl-4-[1-(p-methoxybenzyl)tetrazol-5-yl]-Δ³-cephem

To 73 g. of 7-(2′,2′,2′-trichloroethoxycarboxamido)-3-methyl-4-[1-(p-methoxybenzyl)tetrazol-5-yl]-Δ³-cephem in 500 ml. of 95% acetic acid is added 25 g. of zinc dust, and the mixture stirred vigorously for 3 hrs. at room temperature. The mixture is filtered, and the filtrate added to a large volume of water and extracted with chloroform. The organic layer is washed with water and the product extracted from the organic phase with 1N hydrochloric acid. The aqueous is washed with chloroform, basified with 2N sodium hydroxide solution to pH 7 and extracted with chloroform. The chloroform layer is dried over magnesium sulfate and concentrated under reduced pressure to a small volume. On addition of the concentrate to petroleum ether, the product is precipitated. The solids are filtered and dried, 30 g.

NMR (DMSOd₆): δ = 7(2 q) 8H; 5.5(s) 2H; 5.4(d) 1H; 5.05(d) 1H; 3.7(s) 3H; 3.6(s) 2H; 2.2(s) 3H and 1.4(s) 3H.

EXAMPLE 6

Starting with the intermediate tetrazoles of Example 4, and repeating the procedure of Example 5, the following congeners are synthesized:

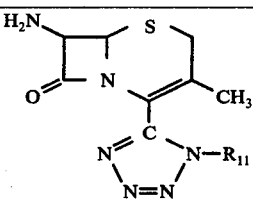

| R₁₁ |
|---|
| 4-C₆H₅CH₂OC₆H₄CH₂— |
| 4-C₆H₅CH₂O-3-FC₆H₃CH₂— |
| 2-Cl-4-CH₃OC₆H₃CH₂— |
| 3-Cl-4-HOC₆H₃CH₂— |
| 3,4-(CH₃O)₂C₆H₃CH₂— |
| 4-HOC₆H₄CH(CH₃)— |
| 2-Br-4-CH₃OC₆H₃CH₂— |
| 4-CH₃OC₆H₄CH(φ)— |
| 2,4-(CH₃O)₂C₆H₃CH(CH₃)— |
| 4-CH₃OC₆H₄CH(n-C₃H₇)— |
| 3-CH₃-4-CH₃OC₆H₃CH₂— |
| 4-C₂H₅CO₂C₆H₄CH₂— |
| 3-F-4-CH₃CO₂C₆H₃CH₂— |
| 4-HOC₆H₄CH(φ)— |
| 3-I-4-CH₃OC₆H₃CH₂— |
| 4-(i-C₃H₇CO₂)C₆H₄CH₂— |
| 3,4-(C₆H₅CH₂O)₂C₆H₃CH₂— |
| 4-CH₃OC₆H₄CH(CH₃)— |
| 4-CH₃OC₆H₄CH(C₂H₅)— |

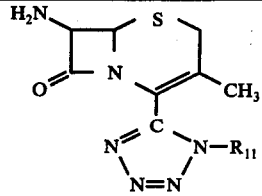

| R₁₁ |
|---|
| 3-F-4-CH₃OC₆H₃CH₂— |
| 3-Cl-4-CH₃OC₆H₃CH(CH₃)— |
| 4-HOC₆H₄CH₂— |
| 4-CH₃CO₂C₆H₄CH₂— |
| 3-F-4-HOC₆H₃CH₂— |
| 3-CH₃O-4-CH₃CO₂C₆H₄CH₂— |
| 4-C₆H₅CH₂OC₆H₃CH(CH₃)— |
| 3-Cl-4-C₆H₄CH₂OC₆H₃CH₂— |
| 3,4-(C₂H₅CO₂)₂C₆H₃CH₂— |
| 4-(n-C₃H₇CO₂)C₆H₄CH₂— |
| 4-(i-C₃H₇CO₂)C₆H₄CH(C₂H₅)— |
| 2-furylmethyl- |
| 5-methyl-2-furylmethyl- |
| 2-thienylmethyl- |
| 5-methyl-2-thienylmethyl- |
| 1-(2-furyl)ethyl- |
| 1-(5-methyl-2-furyl)ethyl- |

EXAMPLE 7

7-Amino-3-methyl-4-(tetrazol-5-yl)-Δ³-cephem

A mixture of 7.0 g. of 7-amino-3-methyl-4-(1-[p-methoxybenzyl]-tetrazol-5-yl)-Δ³-cephem in 50 ml. of trifluoroacetic acid/anisole (4:1) is allowed to stand at 50° C. for 5 hrs. The solution is subsequently poured into a large volume of stirred diethyl ether, and the precipitate which forms is filtered. The solids are dissolved in water, which is extracted several times with ethyl acetate, adjusted to pH 7.0 with 2N aqueous sodium hydroxide and extracted again. The aqueous solution containing the product is freeze dried to give 3.2 g. of the desired compound (containing some sodium trifluoroacetate).

NMR (DMSOd₆): δ = 5.0(d) 1H; 4.6(d) 1H; 3.4(q) 2H; 1.9(s) 3H and 1.3(s) 3H.

EXAMPLE 8

In an analogous manner, when the procedure of Example 7 is repeated, starting with the compounds of Example 6, 7-amino-3-methyl-4-(tetrazol-5-yl)-Δ³-cephem is produced.

EXAMPLE 9

7-(Benzyloxycarboxamido)-3-methyl-Δ³-cephem-4-carboxylic Acid

Sodium bicarbonate (500 g.) is added portionwise over 45 min. to a stirred slurry of 7-amino-3-methyl-Δ³-cephem-4-carboxylic acid (560 g.) in cold water (5.6 liters) and acetone (5.6 liters). When effervescence has ceased, benzyl chloroformate (490 g.) is added and the solution stirred at room temperature overnight. The reaction mixture is then extracted with ethyl acetate (2 × 1 liter), and the pH of the separated aqueous layer adjusted to 2 by the addition of 2N hydrochloric acid. This mixture is then extracted with ethyl acetate (2 × 1 liter), and the solvent from the separated organic layer removed in vacuo. The resultant solid is dissolved in hot ethanol (2 liters), and diluted with warm water (5 liters), to furnish 7-(benzyloxycarboxamido)-3-methyl-Δ³-cephem-4-carboxylic acid as a white solid (750 g.), which is dried in vacuo at 60° C.

NMR (DMSOd$_6$): δ = 8.3(d) 1H; 7.3(m) 5H; 5.4(q) 1H; 5.1(d) 1H; 5(s) 2H; 3.4(q) 2H and 2.1(s) 3H.

EXAMPLE 10

Utilizing the procedure of Example 9, but starting with a suitably ring substituted benzyl chloroformate wherein the substituent is selected from the group consisting of halo, methyl and methoxy, the corresponding 7-(substituted benzyloxycarboxamido)-3-methyl-Δ$^3$-cephem-4-carboxylic acids are prepared.

EXAMPLE 11

7-(Benzyloxycarboxamido)-3-methyl-4-[N-(p-methoxybenzyl)-carbamoyl]-Δ$^3$-cephem A mixture of 7-(benzyloxycarboxamido)-3-methyl-Δ$^3$-cephem-4-carboxylic acid (34.8 g.) and 2,4-dinitrophenol (18.4 g.) are dissolved in dry dioxane (700 ml.). Dicyclohexylcarbodiimide (20.6 g.) is then added and the solution stirred for 20 min. at room temperature. After this time, the precipitated dicyclohexylurea is filtered off, and the filtrate treated with p-methoxybenzylamine (13.7 g.) which is added over 10 min. After a further 15 min., the reaction mixture is diluted wth dry ether (1.4 liters). The precipitate is filtered off, washed with dry ether (500 ml.), and dried in vacuo at 50° C. to yield 40 g. of the desired product as a white solid.

NMR (DMSOd$_6$): δ = 8.4(m) 2H; 7(q) 4H; 5.3(q) 1H; 5.1(s) 2H; 5(d) 1H; 4.3(d) 2H; 3.7(s) 3H; 3.3(s) 2H and 2(s) 3H.

EXAMPLE 12

Starting with the appropriate amine and requisite 7-(benzyloxycarboxamido)3-methyl-Δ$^3$-cephem-4-carboxylic acid and employing the procedure of Example 11, the following Δ$^3$-cephems are prepared:

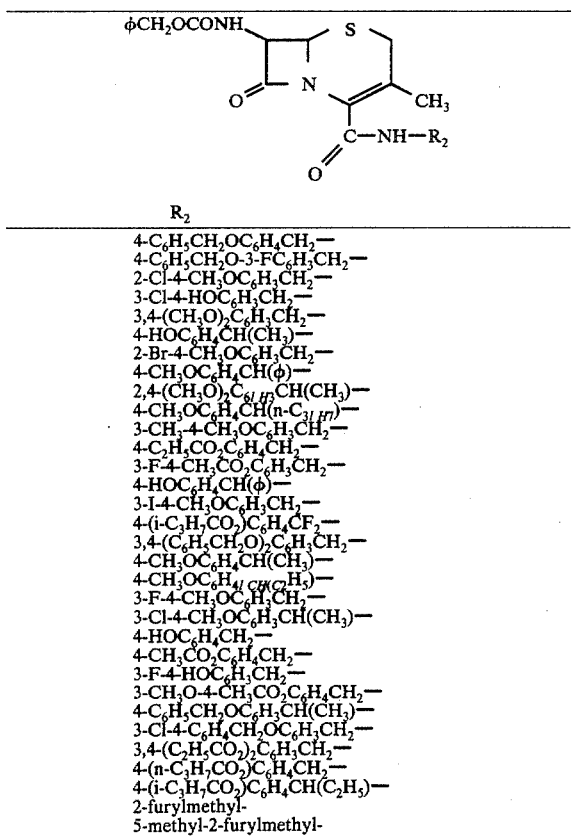

| R$_2$ |
|---|
| 4-C$_6$H$_5$CH$_2$OC$_6$H$_4$CH$_2$— |
| 4-C$_6$H$_5$CH$_2$O-3-FC$_6$H$_3$CH$_2$— |
| 2-Cl-4-CH$_3$OC$_6$H$_3$CH$_2$— |
| 3-Cl-4-HOC$_6$H$_3$CH$_2$— |
| 3,4-(CH$_3$O)$_2$C$_6$H$_3$CH$_2$— |
| 4-HOC$_6$H$_4$CH(CH$_3$)— |
| 2-Br-4-CH$_3$OC$_6$H$_3$CH$_2$— |
| 4-CH$_3$OC$_6$H$_4$CH(φ)— |
| 2,4-(CH$_3$O)$_2$C$_6$H$_3$CH(CH$_3$)— |
| 4-CH$_3$OC$_6$H$_4$CH(n-C$_3$H$_7$)— |
| 3-CH$_3$-4-CH$_3$OC$_6$H$_3$CH$_2$— |
| 4-C$_2$H$_5$CO$_2$C$_6$H$_4$CH$_2$— |
| 3-F-4-CH$_3$CO$_2$C$_6$H$_3$CH$_2$— |
| 4-HOC$_6$H$_4$CH(φ)— |
| 3-I-4-CH$_3$OC$_6$H$_3$CH$_2$— |
| 4-(i-C$_3$H$_7$CO$_2$)C$_6$H$_4$CF$_2$— |
| 3,4-(C$_6$H$_5$CH$_2$O)$_2$C$_6$H$_3$CH$_2$— |
| 4-CH$_3$OC$_6$H$_4$CH(CH$_3$)— |
| 4-CH$_3$OC$_6$H$_4$CH(C$_6$H$_5$)— |
| 3-F-4-CH$_3$OC$_6$H$_3$CH$_2$— |
| 3-Cl-4-CH$_3$OC$_6$H$_3$CH(CH$_3$)— |
| 4-HOC$_6$H$_4$CH$_2$— |
| 4-CH$_3$CO$_2$C$_6$H$_4$CH$_2$— |
| 3-F-4-HOC$_6$H$_3$CH$_2$— |
| 3-CH$_3$O-4-CH$_3$CO$_2$C$_6$H$_4$CH$_2$— |
| 4-C$_6$H$_5$CH$_2$OC$_6$H$_3$CH(CH$_3$)— |
| 3-Cl-4-C$_6$H$_4$CH$_2$OC$_6$H$_3$CH$_2$— |
| 3,4-(C$_2$H$_5$CO$_2$)$_2$C$_6$H$_3$CH$_2$— |
| 4-(n-C$_3$H$_7$CO$_2$)C$_6$H$_4$CH$_2$— |
| 4-(i-C$_3$H$_7$CO$_2$)C$_6$H$_4$CH(C$_2$H$_5$)— |
| 2-furylmethyl- |
| 5-methyl-2-furylmethyl- |

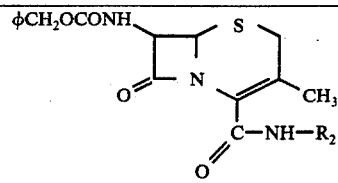

| R$_2$ |
|---|
| 2-thienylmethyl- |
| 5-methyl-2-thienylmethyl- |
| 1-(2-furyl)ethyl- |
| 1-(5-methyl-2-furyl)ethyl- |

EXAMPLE 13

7-Amino-3-methyl-4-[N-(p-methoxybenzyl)carbamoyl]-Δ$^3$-cephem 7-(Benzyloxycarboxamido)-3-methyl-4-[N-(p-methoxybenzyl)carbamoyl]-Δ$^3$-cephem (20 g.) is dissolved in hydrobromic acid/acetic acid (200 ml.) and the solution stirred at room temperature until gas evolution ceases. The mixture is poured into a large volume (ca. 2 liters) of stirred ether and the resulting precipitate collected. The solid is dissolved in water and the aqueous solution washed with ethyl acetate (2x). The aqueous solution is adjusted to pH 7.5 with sodium bicarbonate and the suspension extracted with chloroform. The chloroform extract is dried (MgSO$_4$) and evaporated under reduced pressure to leave the product as a pale yellow solid (7.7 g.).

NMR (DMSOd$_6$): δ = 8.0(t) 1H; 7.0(q) 4H; 4.8(d) 1H; 4.6(d) 1H; 4.4(d) 2H; 3.7(s) 3H; 3.2 (q) 2H; 201(s) 2H and 2.0(s) 3H.

EXAMPLE 14

Starting with the intermediates of Example 12, and following the deacylation procedure of Example 13, the following 7-amino-Δ$^3$-cephem derivatives are synthesized:

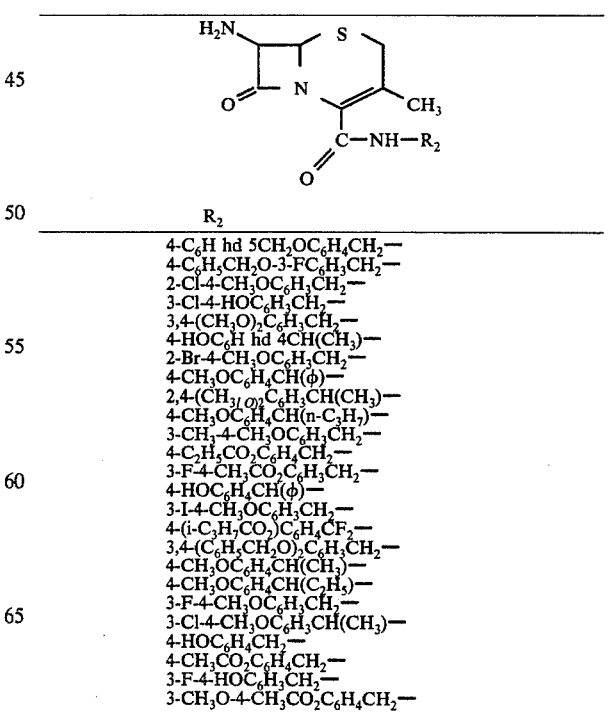

| R$_2$ |
|---|
| 4-C$_6$H hd 5CH$_2$OC$_6$H$_4$CH$_2$— |
| 4-C$_6$H$_5$CH$_2$O-3-FC$_6$H$_3$CH$_2$— |
| 2-Cl-4-CH$_3$OC$_6$H$_3$CH$_2$— |
| 3-Cl-4-HOC$_6$H$_3$CH$_2$— |
| 3,4-(CH$_3$O)$_2$C$_6$H$_3$CH$_2$— |
| 4-HOC$_6$H hd 4CH(CH$_3$)— |
| 2-Br-4-CH$_3$OC$_6$H$_3$CH$_2$— |
| 4-CH$_3$OC$_6$H$_4$CH(φ)— |
| 2,4-(CH$_{3(O)2}$)C$_6$H$_3$CH(CH$_3$)— |
| 4-CH$_3$OC$_6$H$_4$CH(n-C$_3$H$_7$)— |
| 3-CH$_3$-4-CH$_3$OC$_6$H$_3$CH$_2$— |
| 4-C$_2$H$_5$CO$_2$C$_6$H$_4$CH$_2$— |
| 3-F-4-CH$_3$CO$_2$C$_6$H$_3$CH$_2$— |
| 4-HOC$_6$H$_4$CH(φ)— |
| 3-I-4-CH$_3$OC$_6$H$_3$CH$_2$— |
| 4-(i-C$_3$H$_7$CO$_2$)C$_6$H$_4$CF$_2$— |
| 3,4-(C$_6$H$_5$CH$_2$O)$_2$C$_6$H$_3$CH$_2$— |
| 4-CH$_3$OC$_6$H$_4$CH(CH$_3$)— |
| 4-CH$_3$OC$_6$H$_4$CH(C$_6$H$_5$)— |
| 3-F-4-CH$_3$OC$_6$H$_3$CH$_2$— |
| 3-Cl-4-CH$_3$OC$_6$H$_3$CH(CH$_3$)— |
| 4-HOC$_6$H$_4$CH$_2$— |
| 4-CH$_3$CO$_2$C$_6$H$_4$CH$_2$— |
| 3-F-4-HOC$_6$H$_3$CH$_2$— |
| 3-CH$_3$O-4-CH$_3$CO$_2$C$_6$H$_4$CH$_2$— |

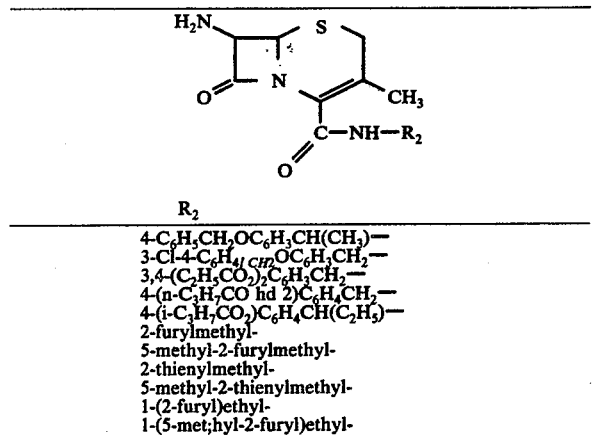

| $R_2$ |
|---|
| 4-C₆H₅CH₂OC₆H₃CH(CH₃)— |
| 3-Cl-4-C₆H₄CH₂OC₆H₃CH₂— |
| 3,4-(C₂H₅CO₂)₂C₆H₃CH₂— |
| 4-(n-C₃H₇CO hd 2)C₆H₄CH₂— |
| 4-(i-C₃H₇CO₂)C₆H₄CH(C₂H₅)— |
| 2-furylmethyl- |
| 5-methyl-2-furylmethyl- |
| 2-thienylmethyl- |
| 5-methyl-2-thienylmethyl- |
| 1-(2-furyl)ethyl- |
| 1-(5-methyl-2-furyl)ethyl- |

EXAMPLE 15

7-(N-Triphenylmethylamino)-3-methyl-4-[N-(p-methoxybenzyl)-carbamoyl]-Δ³-cephem

To 24 g. of 7-amino-3-methyl-4-[N-(p-methoxybenzyl)carbamoyl]-Δ³-cephem in chloroform (ethanol free; 300 ml.) is added triphenylmethyl chloride (21.0 g.) and triethylamine (7.64 g.). The mixture is allowed to stand at room temperature in the absence of light for 15 hrs. The solution is then diluted several-fold with chloroform and washed twice with water. The organic solution is dried (MgSO₄) and evaporated to dryness to leave the required product as a foam. Trituration with light petroleum ether gives a pale yellow solid (40 g.).

NMR (CDCl₃): δ = 7.2, 9H; 4.6(q) 1H; 4.4(d) 2H; 4.1(d) 1H; 3.7(s) 3H; 3.0, 3H and 2.0(s) 3H.

EXAMPLE 16

The procedure of Example 15 is repeated, substituting the 7-amino-Δ³-cephems of Example 14 for 7-amino-3-methyl-4-[N-(p-methoxybenzyl)carbamoyl]-Δ³-cephem, to provide the following compounds:

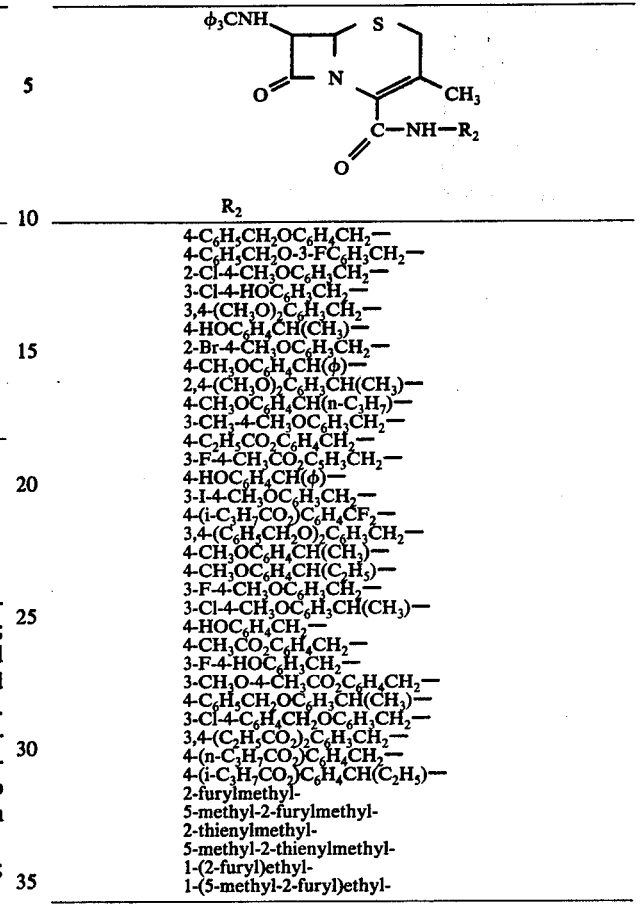

| $R_2$ |
|---|
| 4-C₆H₅CH₂OC₆H₄CH₂— |
| 4-C₆H₅CH₂O-3-FC₆H₃CH₂— |
| 2-Cl-4-CH₃OC₆H₃CH₂— |
| 3-Cl-4-HOC₆H₃CH₂— |
| 3,4-(CH₃O)₂C₆H₃CH₂— |
| 4-HOC₆H₄CH(CH₃)— |
| 2-Br-4-CH₃OC₆H₃CH₂— |
| 4-CH₃OC₆H₄CH(φ)— |
| 2,4-(CH₃O)₂C₆H₃CH(CH₃)— |
| 4-CH₃OC₆H₄CH(n-C₃H₇)— |
| 3-CH₃-4-CH₃OC₆H₃CH₂— |
| 4-C₂H₅CO₂C₆H₄CH₂— |
| 3-F-4-CH₃CO₂C₆H₃CH₂— |
| 4-HOC₆H₄CH(φ)— |
| 3-I-4-CH₃OC₆H₃CH₂— |
| 4-(i-C₃H₇CO₂)C₆H₄CF₂— |
| 3,4-(C₆H₅CH₂O)₂C₆H₃CH₂— |
| 4-CH₃OC₆H₄CH(CH₃)— |
| 4-CH₃OC₆H₄CH(C₂H₅)— |
| 3-F-4-CH₃OC₆H₃CH₂— |
| 3-Cl-4-CH₃OC₆H₃CH(CH₃)— |
| 4-HOC₆H₄CH₂— |
| 4-CH₃CO₂C₆H₄CH₂— |
| 3-F-4-HOC₆H₃CH₂— |
| 3-CH₃O-4-CH₃CO₂C₆H₄CH₂— |
| 4-C₆H₅CH₂OC₆H₃CH(CH₃)— |
| 3-Cl-4-C₆H₄CH₂OC₆H₃CH₂— |
| 3,4-(C₂H₅CO₂)₂C₆H₃CH₂— |
| 4-(n-C₃H₇CO₂)C₆H₄CH₂— |
| 4-(i-C₃H₇CO₂)C₆H₄CH(C₂H₅)— |
| 2-furylmethyl- |
| 5-methyl-2-furylmethyl- |
| 2-thienylmethyl- |
| 5-methyl-2-thienylmethyl- |
| 1-(2-furyl)ethyl- |
| 1-(5-methyl-2-furyl)ethyl- |

EXAMPLE 17

The procedure of Example 15 is again repeated, starting with the appropriate triphenylmethyl chloride and 7-amino-Δ³-cephem from Example 14 to give the following compounds:

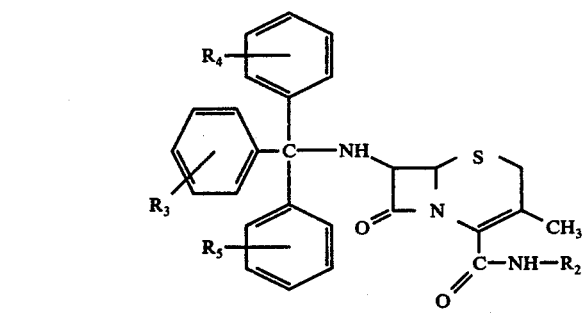

| $R_3$ | $R_4$ | $R_5$ | $R_2$ |
|---|---|---|---|
| H— | H— | 4-CH₃— | 4-C₆H₅CH₂OC₆H₄CH₂— |
| H— | H— | 2-CH₃— | 4-C₆H₅CH₂O-3-FC₆H₃CH₂— |
| H— | H— | 3-CH₃O— | 2-Cl-4-CH₃OC₆H₃CH₂— |
| H— | H— | 4-CH₃O— | 3-Cl-4-HOC₆H₃CH₂— |
| H— | H— | 2-F— | 3,4-(CH₃O)₂C₆H₃CH₂— |
| H— | H— | 4-F— | 4-HOC₆H₄CH(CH₃)— |
| H— | H— | 3-Cl— | 2-Br-4-CH₃OC₆H₃CH₂— |
| H— | H— | 4-Cl— | 4-CH₃OC₆H₄CH(φ)— |
| H— | H— | 4-Br— | 2,4-(CH₃O)₂C₆H₃CH(CH₃)— |
| H— | 4-CH₃— | 4-CH₃— | 4-CH₃OC₆H₄CH(n-C₃H₇)— |
| H— | 4-CH₃— | 4-CH₃— | 3-CH₃-4-CH₃OC₆H₃CH₂— |
| H— | 4-CH₃— | 4-CH₃O— | 4-C₂H₅CO₂C₆H₄CH₂— |
| H— | 4-CH₃O— | 4-CH₃O— | 3-F-4-CH₃CO₂C₆H₃CH₂— |
| H— | 3-CH₃O— | 3-F— | 4-HOC₆H₄CH(φ)— |
| H— | 3-CH₃O— | 4-F— | 3-I-4-CH₃OC₆H₃CH₂— |

-continued

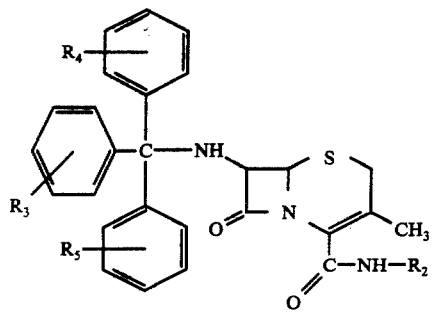

| $R_3$ | $R_4$ | $R_5$ | $R_2$ |
|---|---|---|---|
| H— | 3-CH$_3$O— | 4-F— | 4-(i-C$_3$H$_7$CO$_2$)C$_6$H$_4$CH$_2$— |
| H— | 4-Cl— | 3-Cl— | 3,4-(C$_6$H$_5$CH$_2$O)$_2$C$_6$H$_3$CH$_2$— |
| H— | 4-Cl— | 4-F— | 4-CH$_3$OC$_6$H$_4$CH(CH$_3$)— |
| H— | 4-Cl— | 4-Br— | 4-CH$_3$OC$_6$H$_4$CH(C$_2$H$_5$)— |
| H— | 4-Br— | 4-Br— | 3-F-4-CH$_3$OC$_6$H$_3$CH$_2$— |
| H— | 3-Br— | 4-CH$_3$O— | 3-Cl-4-CH$_3$OC$_6$H$_3$CH(CH$_3$)— |
| H— | 4-Br— | 4-CH$_3$— | 4-HOC$_6$H$_4$CH$_2$— |
| H— | H— | C$_6$H$_5$— | 4-CH$_3$CO$_2$C$_6$H$_4$CH$_2$— |
| H— | C$_6$H$_5$— | C$_6$H$_5$— | 3-F-4-HOC$_6$H$_3$CH$_2$— |
| 2-CH$_3$— | 2-CH$_3$— | 4-CH$_3$— | 3-CH$_3$O-4-CH$_3$CH$_2$CO$_2$C$_6$H$_4$CH$_2$— |
| 4-CH$_3$O— | 4-CH$_3$— | 4-CH$_3$— | 4-C$_6$H$_5$CH$_2$OC$_6$H$_3$CH(CH$_3$)— |
| 4-CH$_3$— | 2-Cl— | 4-CH$_3$— | 3-Cl-4-C$_6$H$_5$CH$_2$OC$_6$H$_3$CH$_2$— |
| 4-CH$_3$— | 4-Br— | 4-OCH$_3$— | 3,4-(C$_2$H$_5$CO$_2$)$_2$C$_6$H$_3$CH$_2$— |
| 4-CH$_3$— | 4-CH$_3$— | 4-CH$_3$— | 4-(n-C$_3$H$_7$CO$_2$)C$_6$H$_4$CH$_2$— |
| 4-CH$_3$— | 4-CH$_3$— | 4-CH$_3$— | 4-(i-C$_3$H$_7$CO$_2$)C$_6$H$_4$CH(C$_2$H$_5$)— |
| 4-CH$_3$— | 4-C$_6$H$_5$— | 4-Cl— | 2-furylmethyl- |
| 4-Cl— | 2-Cl— | 4-Cl— | 5-methyl-2-furylmethyl- |
| 3-Cl | 4-CH$_3$— | 4-CH$_3$— | 2-thienylmethyl- |
| 4-CH$_3$O— | 4-CH$_3$O— | 4-CH$_3$O— | 5-methyl-2-thienylmethyl- |
| 4-F— | 4-Br— | 4-F— | 1-(2-furyl)ethyl- |
| 2-Cl— | 2-F— | 4-Br— | 1-(5-methyl-2-furyl)ethyl- |

EXAMPLE 18

7-(N-Triphenylmethylamino)-3-methyl-4-[1-(p-methoxybenzyl)-tetrazol-5-yl]-Δ$^3$-cephem 7-(N-Triphenylmethylamino)-3-methyl-4-[N-(p-methoxybenzyl)carbamoyl]-Δ$^3$-cephem (2.8 g.) in ethanol-free chloroform (7.5 ml.) containing pyridine (0.6 g.) is treated with phosgene in chloroform (3.7 ml., 1.7M). The reaction is allowed to stir for 30 min. at room temperature. The excess phosgene is removed under reduced pressure and additional chloroform added until the volume of solution is 10 ml. Tetramethylguanidine hydrogen azide (2.4 g.) in chloroform (5ml.) is added to the above prepared solution and the reaction allowed to stir at room temperature for 20 min. The solution is washed with water, dried (MgSO$_4$) and evaporated under reduced pressure to give an oil. Trituration with light petroleum ether gives 2.2 g. of the desired product.

NMR (CDCl$_3$): δ = 7.2, 19H; 5.3(s) 2H; 4.4(q) 1H; 4.2(d) 1H; 3.6(s) 3H; 3.0, 3H and 1.2(s) 3H.

EXAMPLE 19

The following Δ$^3$-cephems are prepared by repeating the procedure of Example 18, starting with the appropriate intermediates of Examples 16 and 17:

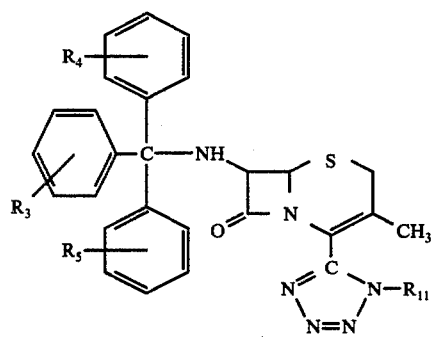

| $R_3$ | $R_4$ | $R_5$ | $R_2$ |
|---|---|---|---|
| H— | H— | H— | 4-C$_6$H$_5$CH$_2$OC$_6$H$_4$CH$_2$— |
| H— | H— | H— | 4-C$_6$H$_5$CH$_2$O-3-FC$_6$H$_3$CH$_2$— |
| H— | H— | H— | 2-Cl-4-CH$_3$OC$_6$H$_3$CH$_2$— |
| H— | H— | H— | 3-Cl-4-HOC$_6$H$_3$CH$_2$— |
| H— | H— | H— | 3,4-(CH$_3$O)$_2$C$_6$H$_3$CH$_2$— |
| H— | H— | H— | 4-HOC$_6$H$_4$CH(CH$_3$)— |
| H— | H— | H— | 2-Br-4-CH$_3$OC$_6$H$_3$CH$_2$— |
| H— | H— | H— | 4-CH$_3$OC$_6$H$_4$CH(φ)— |
| H— | H— | H— | 2,4-(CH$_3$O)$_2$C$_6$H$_3$CH(CH$_3$)— |
| H— | H— | H— | 4-CH$_3$OC$_6$H$_4$CH(n-C$_3$H$_7$)— |
| H— | H— | H— | 3-CH$_3$-4-CH$_3$OC$_6$H$_3$CH$_2$— |

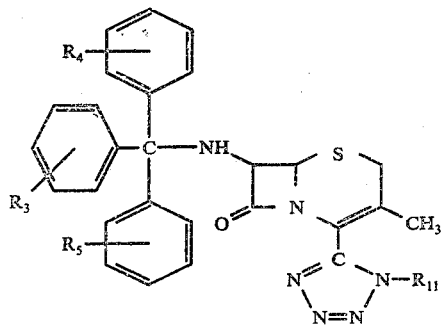

| R₃ | R₄ | R₅ | R₁₁ |
|---|---|---|---|
| H— | H— | H— | 4-C₂H₅CO₂C₆H₄CH₂— |
| H— | H— | H— | 3-F-4-CH₃CO₂C₆H₃CH₂— |
| H— | H— | H— | 4-HOC₆H₄CH(φ)— |
| H— | H— | H— | 3-I-4-CH₃OC₆H₃CH₂— |
| H— | H— | H— | 4-(i-C₃H₇CO₂)C₆H₄CH₂— |
| H— | H— | H— | 3,3-(C₆H₅CH₂O)₂C₆H₃CH₂— |
| H— | H— | H— | 4-CH₃OC₆H₄CH(CH₃)— |
| H— | H— | H— | 4-CH₃OC₆H₄CH(C₂H₅)— |
| H— | H— | H— | 3-F-4-CH₃OC₆H₃CH₂— |
| H— | H— | H— | 3-Cl-4-CH₃OC₆H₃CH(CH₃)— |
| H— | H— | H— | 4-HOC₆H₄CH₂— |
| H— | H— | H— | 4-CH₃CO₂C₆H₄CH₂— |
| H— | H— | H— | 3-F-4-HOC₆H₃CH₂— |
| H— | H— | H— | 3-CH₃O-4-CH₃CO₂C₆H₃CH₂— |
| H— | H— | H— | 4-C₆H₅CH₂OC₆H₃CH(CH₃)— |
| H— | H— | H— | 3-Cl-4-C₆H₅CH₂OC₆H₃CH₂— |
| H— | H— | H— | 3,4-(C₂H₅CO₂)₂C₆H₃CH₂— |
| H— | H— | H— | 4-(n-C₃H₇CO₂)C₆H₄CH₂— |
| H— | H— | H— | 4-(i-C₃H₇CO₂)C₆H₄CH(C₂H₅)— |
| H— | H— | H— | 2-furylmethyl- |
| H— | H— | H— | 5-methyl-2-furylmethyl- |
| H— | H— | H— | 2-thienylmethyl- |
| H— | H— | H— | 5-methyl-2-thienylmethyl- |

| R₃ | R₄ | R₅ | R₁₁ |
|---|---|---|---|
| H— | H— | H— | 1-(2-furyl)ethyl- |
| H— | H— | H— | 1-(5-methyl-2-furyl)ethyl- |
| H— | H— | 4-CH₃— | 4-C₆H₅CH₂OC₆H₄CH₂— |
| H— | H— | 2-CH₃— | 4-C₆H₅CH₂O-3-FC₆H₃CH₂— |
| H— | H— | 3-CH₃O— | 2-Cl-4-CH₃OC₆H₃CH₂— |
| H— | H— | 4-CH₃O— | 4-Cl-4-HOC₆H₃CH₂— |
| H— | H— | 2-F— | 2:Br-4-CH₃OC₆H₃CH₂— |
| H— | H— | 4-F— | 2,4-(CH₃O)₂C₆H₃CH(CH₃)— |
| H— | H— | 3-Cl— | 4-C₂H₅CO₂C₆H₄CH₂— |
| H— | H— | 4-Cl— | 3-CH₃-4-CH₃OC₆H₃CH₂— |
| H— | H— | 4-Br— | 3-F-4-CH₃CO₂C₆H₃CH₂— |
| H— | 4-CH₃— | 4-CH₃— | 3-I-4-CH₃OC₆H₃CH₂— |
| H— | 4-CH₃— | 4-CH₃— | 4-(i-C₃H₇CO₂)C₆H₄CH₂— |
| H— | 4-CH₃— | 4-CH₃O— | 3,4-(C₆H₅CH₂O)₂C₆H₃CH₂— |
| H— | 4-CH₃O— | 4-CH₃O— | 4-CH₃OC₆H₄CH(CH₃)— |
| H— | 3-CH₃O— | 3-F— | 4-CH₃OC₄CH(C₂H₅)— |
| H— | 3-CH₃O— | 4-F— | 3,4-(CH₃O)₂C₆H₃CH₂— |
| H— | 3-CH₃O— | 4-F— | 3-F-4-CH₃OC₆H₃CH₂— |
| H— | 4-Cl— | 3-Cl— | 3-CL-4-CH₃OC₆H₃CH(CH₃)— |
| H— | 4-Cl— | 4-F— | 4-HOC₆H₄CH₂— |
| H— | 4-Cl— | 4-Br— | 4-HOC₆H₄CH(CH₃)— |
| H— | 4-Br— | 4-Br— | 4-CH₃CO₂C₆H₄CH₂— |
| H— | 3-Br— | 4-CH₃O— | 3-Cl-4-HOC₆H₃CH₂— |
| H— | 4-Br— | 4-CH₃— | 3-Cl-4-CH₃CO₂C₆H₃CH₂— |
| H— | H— | C₆H₅— | 4-C₆H₅CH₂OC₆H₃CH(CH₃)— |
| H— | C₆H₅— | C₆H₅— | 3-Cl-4-C₆H₅CH₂OC₆H₃CH₂— |
| 2-CH₃— | 2-CH₃— | 4-CH₃— | 2-F-4-HOC₆H₃CH₂— |
| 4-CH₃O— | 4-CH₃— | 4-CH₃— | 3,4-(C₂H₅CO₂)₂C₆H₃CH₂— |
| 4-Cl— | 2-Cl— | 4-CH₃— | 4-(n-C₃H₇CO₂)C₆H₄CH₂— |
| 4-CH₃— | 4-Br— | 4-OCH₃— | 2:furylmethyl- |
| 4-CH₃— | 4-CH₃— | 4-CH₃— | 5-methyl-2-furylmethyl- |
| 4-CH₃— | 4-CH₃— | 4-CH₃— | 2-thienylmethyl- |
| 4-CH₃— | 4-C₆H₅— | 4-Cl— | 1-(2-furyl)ethyl- |
| 4-Cl— | 2-Cl— | 4-Cl— | 1-(5-methyl-2-furyl)ethyl- |

EXAMPLE 20

7-Amino-3-methyl-4-[1-(p-methoxybenzyl)tetrazol-5-yl]-Δ³-cephem 7-(N-Triphenylmethylamino)-3-methyl-4-[1-(p-methoxybenzyl)tetrazol-5-yl]-Δ³-cephem (1.5 g.) is treated with formic acid (30 ml.) and the solution allowed to stand at room temperature for 30 min. The solution is poured into water (100 ml.) and the aqueous suspension washed with ethyl acetate. The aqueous solution is adjusted to pH 7.5 with 2N aqueous sodium hydroxide and the mixture extracted with chloroform. The organic solution is dried (MgSO₄) and evaporated under reduced pressure to leave a foam. Trituration with light petroleum ether gives 400 mg. of the desired product as a solid.

NMR (CDCl₃): δ = 7.0(q) 4H; 5.4(s) 2H; 4.9(d) 1H; 4.6(d) 1H; 3.7(s) 3H; 3.3(q) 2H; 2.0(s) 2H and 1.4(s) 3H.

In a similar manner, when the compounds of Example 19 are subjected to the above hydrolysis conditions, the following 7-amino-$\Delta^3$-cephems are produced, said products being identical with those of Example 6:

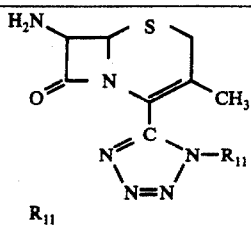

| $R_{11}$ |
|---|
| 4-$C_6H_5CH_2OC_6H_4CH_2$— |
| 4-$C_6H_5CH_2O$-3-$FC_6H_3CH_2$— |
| 2-Cl-4-$CH_3OC_6H_3CH_2$— |
| 3-Cl-4-$HOC_6H_3CH_2$— |
| 3,4-$(CH_3O)_2C_6H_3CH_2$— |
| 4-$HOC_6H_4CH(CH_3)$— |
| 2-Br-4-$CH_3OC_6H_3CH_2$— |
| 4-$CH_3OC_6H_4CH(\phi)$— |
| 2,4-$(CH_3O)_2C_6H_3CH(CH_3)$— |
| 4-$CH_3OC_6H_4CH(n$-$C_3H_7)$— |
| 3-$CH_3$-4-$CH_3OC_6H_3CH_2$— |
| 4-$C_2H_5CO_2C_6H_4CH_2$— |
| 3-F-4-$CH_3CO_2C_6H_3CH_2$— |
| 4-$HOC_6H_4CH(\phi)$— |
| 3-I-4-$CH_3OC_6H_3CH_2$— |
| 4-(i-$C_3H_7CO_2)C_6H_4CH_2$— |
| 3,4-$(C_6H_5CH_2O)_2C_6H_3CH_2$— |
| 4-$CH_3OC_6H_4CH(CH_3)$— |
| 4-$CH_3OC_6H_4CH(C_2H_5)$— |
| 3-F-4-$CH_3OC_6H_3CH_2$— |
| 3-Cl-4-$CH_3OC_6H_3CH(CH_3)$— |
| 4-$HOC_6H_4CH_2$— |
| 4-$CH_3CO_2C_6H_4CH_2$— |
| 3-F-4-$HOC_6H_3CH_2$— |
| 3-$CH_3O$-4-$CH_3CO_2C_6H_4CH_2$— |
| 4-$C_6H_5CH_2OC_6H_3CH(CH_3)$— |
| 3-Cl-4-$C_6H_5CH_2OC_6H_3CH_2$— |
| 3,4-$(C_2H_5CO_2)_2C_6H_3CH_2$— |
| 4-(n-$C_3H_7CO_2)C_6H_4CH_2$— |
| 4-(i-$C_3H_7CO_2)C_6H_4CH(C_2H_5)$— |
| 2-furylmethyl- |
| 5-methyl-2-furylmethyl- |
| 2-thienylmethyl- |
| 5-methyl-2-thienylmethyl- |
| 1-(2-furyl)ethyl- |
| 1-(5-methyl-2-furyl)ethyl- |

EXAMPLE 21

7-[D-($\alpha$-amino-$\alpha$-phenyl)acetamido]-3-methyl-4-(tetrazol-5-yl)-$\Delta^3$-cephem

A.

7-[D-($\alpha$-t-Butoxycarboxamido-$\alpha$-phenyl)acetamido]-3-methyl-4-(tetrazol-5-yl)-$\Delta^3$-cephem D-($\alpha$-t-Butoxycarboxamido-$\alpha$-phenyl)acetic acid (0.251 g.) in tetrahydrofuran (2 ml.) is treated with triethylamine (0.101 g.) and ethyl chloroformate (0.108 g.) at −10° C. After 15 min. at this temperature, the sodium salt of 7-amino-3-methyl-4-(tetrazol-5-yl)-$\Delta^3$-cephem (0.400 g.) in water (3 ml.) is added with stirring in one portion. The mixture is diluted with tetrahydrofuran (2 ml.) and allowed to warm up to room temperature. After one hr. the solution is adjusted to pH 2 with 2N hydrochloric acid and the suspension extracted with ethyl acetate. The ethyl acetate solution is washed with water, dried (MgSO$_4$), concentrated under reduced pressure, and poured into a large volume of light petroleum ether to give a white solid. The compound is recrystallized from chloroform (316 ml.).

NMR (DMSOd$_6$) $\delta$ = 7.6(d) 1H; 7.2, 5H; 6.0(d) 1H; 5.6(q) 1H; 5.2(d) 1H; 4.9(d) 1H; 3.3(q) 2H; 2.0(s) 3H and 1.2(s) 9H.

B.

7-[D-($\alpha$-Amino-$\alpha$-phenyl)acetamido]-3-methyl-4-(tetrazol-5-yl)-$\Delta^3$-cephem trifluoroacetate 7-[D-($\alpha$-t-Butoxycarboxamido-$\alpha$-phenyl)acetamido]-3-methyl-4-(tetrazol-5-yl)-$\Delta^3$-cephem (26 mg.) is dissolved in trifluoroacetic acid (0.5 ml.) and allowed to stand at room temperature for 20 min. To the solution is added ether and the precipitate collected (24 mg.).

NMR (DMSOd$_6$—D$_2$O): $\delta$ = 7.4(s) 5H; 5.6(d) 1H; 5.1(d) 1H; 5.0(s) 1H; 3.4, 2H and 2.0(s) 3H.

EXAMPLE 22

7-[D-$\alpha$-Amino-$\alpha$-(p-hydroxyphenyl)acetamido]-3-methyl-4-(tetrazol-5-yl)-$\Delta^3$-cephem The procedures of Example 21A and B are repeated, starting with the requisite D-[$\alpha$-t-butoxycarboxamido-$\alpha$-(p-hydroxyphenyl)]acetic acid in place of D-($\alpha$-t-butoxycarboxamido-$\alpha$-phenyl)acetic acid, to provide the desired product.

IR (CH$_2$Cl$_2$): $\gamma_{max}$: 1780 cm$^{-1}$ ($\beta$-lactam carbonyl); 1660 cm$^{-1}$ (—CONH—).

EXAMPLE 23

The procedures of Example 21A and B are again repeated, starting with the appropriate $\alpha$-amino acid derivative, said compounds being prepared by known procedures such as those taught by Greenstein and Winitz in "Chemistry of Amino Acids," John Wiley and Sons, Inc., New York/London, 1961, p. 698–700 and the references cited therein; and resolved into their optical isomers by the methods taught by Greenstein and Winitz, loc. cit., p. 715–755, Nishimura et. al., Nippon Kagaku Zasshi, 82, 1688 (1961), Belg. Pat. No. 795,874 and British Pat. No. 1,221,227, to provide the following cephem analogs:

| Ar | *(configuration) |
|---|---|
| 3-HOC$_6$H$_4$— | D |
| 3,4-(HO)$_2$C$_6$H$_3$— | DL |
| 4-(CH$_3$O)C$_6$H$_4$— | D |
| 4-HOC$_6$H$_4$— | L |
| 2-thienyl— | D |
| 3-D-4-HOC$_6$H$_3$— | D |
| 4-ClC$_6$H$_4$— | DL |
| 3-ClC$_6$H$_4$— | DL |
| 4-FC$_6$H$_4$— | D |
| 2-Br-5-HOC$_6$H$_3$— | DL |
| 3-FC$_6$H$_4$— | D |
| 4-FC$_6$H$_4$— | L |
| 2-ClC$_6$H$_4$— | D |
| 2-ClC$_6$H$_4$— | L |
| 3-BrC$_6$H$_4$— | D |
| 3-BrC$_6$H$_4$— | L |
| 3-ClC$_6$H$_4$— | D |
| 4-ClC$_6$H$_4$— | D |
| 2,4-Cl$_2$C$_6$H$_3$— | DL |
| 3,4-Cl$_2$C$_6$H$_3$— | DL |
| 2-FC$_6$H$_4$— | D |
| 3-FC$_6$H$_4$— | D |
| 3-FC$_6$H$_4$— | L |
| 4-BrC$_6$H$_4$— | D |
| 3-HOC$_6$H$_4$— | L |
| 4-HOC$_6$H$_4$— | DL |
| 3-CH$_3$C$_6$H$_4$— | D |
| 3-CH$_3$C$_6$H$_4$— | L |
| 2-CH$_3$OC$_6$H$_4$— | DL |

-continued

Ar—CHCONH—[β-lactam-cephem with tetrazol-5-yl, CH₃]
|
NH₂

| Ar | *(configuration) |
|---|---|
| 3,4-(CH₃O)₂C₆H₃— | DL |
| 3,5-(CH₃O)₂C₆H₃— | D |
| 3-thienyl- | D |
| 3-thienyl- | DL |
| 4-H₂NC₆H₄— | D |
| 3-H₂NC₆H₄— | D |
| 3-Cl-4-H₂NC₆H₃— | D |
| 3-Cl-5-(CH₃O)C₆H₃— | D |
| 2-Cl-4-CH₃C₆H₃— | DL |
| 2-F-3-CH₃C₆H₃— | D |
| 2-CH₃-4-CH₃OC₆H₃— | DL |

EXAMPLE 24

7-(D-α-Hydroxyphenylacetamido)-3-methyl-4-(tetrazol-5-yl)-Δ³-cephem

A.

7-(D-α-Formyloxyphenylacetamido)-3-methyl-4-(tetrazol-5-yl)-Δ³-cephem

D-O-Formylmandelic acid (1.8 g.) in ether (15 ml.) is treated with oxalyl chloride (2.5 ml.) and one drop of dimethylformamide. After the vigorous reaction has subsided (30 min.) the ether is removed under reduced pressure and the residue in THF (10 ml.) is added to a stirred solution of 7-amino-3-methyl-4-(tetrazol-5-yl)-Δ³-cephem (1 g.) in water/THF mixture (1:1; 20 ml.) containing excess sodium bicarbonate. After stirring for a further hour at room temperature the mixture is adjusted to pH 2 with 2N hydrochloric acid and the mixture extracted with ethyl acetate. The organic solution is washed with water, dried (MgSO₄), and evaporated under reduced pressure to leave the required product as a solid (350 mg.).

NMR (DMSOd₆): δ = 8.2(s) 1H; 7.2(s) 5H; 6.0(s) 1H; 5.5(q) 1H; 5.1(d) 1H; 3.5(s) 2H and 2.0, 3H.

B.

7-(D-α-Hydroxyphenylacetamido)-3-methyl-4-(tetrazol-5-yl)-Δ³-cephem 7-(D-α-Formyloxyphenylacetamido)-3-methyl-4-(tetrazol-5-yl)-Δ³-cephem (0.34 g.) is dissolved in excess aqueous sodium bicarbonate and allowed to stand at 30° C. for 3 hours. The solution is adjusted to pH 2 with 2N hydrochloric acid and the suspension extracted with ethyl acetate. The organic solution is dried (MgSO₄) and evaporated under reduced pressure to leave the required product as a solid (0.26 g.).

NMR (DMSOd₆): δ = 9.0, 1H; 7.3(s) 5H; 5.6(q) 1H; 5.2(d) 1H; 5.1(s) 1H; 3.6(s) 2H and 2.0(s) 3H.

EXAMPLE 25

Starting with the requisite mandelic acid derivative, prepared by the method as taught in "Organic Synthesis," John Wiley and Sons, Inc., New York/London, 1956, Coll. Vol. I, p. 336, and employing the procedure of Example 24, the following congeners are synthesized:

Ar—CHCONH—[β-lactam-cephem with tetrazol-5-yl, CH₃]
|
OH

| Ar | *(configuration) |
|---|---|
| 2-ClC₆H₄— | D |
| 3-ClC₆H₄— | D |
| 4-ClC₆H₄— | DL |
| 2-FC₆H₄— | L |
| 4-FC₆H₄— | D |
| 4-FC₆H₄— | L |
| 3-BrC₆H₄— | DL |
| 3-CH₃C₆H₄— | D |
| 4-CH₃C₆H₄— | DL |
| 4-CH₃OC₆H₄— | D |
| 4-CH₃OC₆H₄— | DL |
| 3-CH₃OC₆H₄— | D |
| 2-HOC₆H₄— | D |
| 3-HOC₆H₄— | D |
| 4-HOC₆H₄— | DL |
| 4-HOC₆H₄— | D |
| 3-H₂NC₆H₄— | D |
| 2,4-Cl₂C₆H₃— | D |
| 2,3-Cl₂C₆H₃— | DL |
| 3,5-Cl₂C₆H₃— | D |
| 2-Cl-4-FC₆H₃— | D |
| 3-Cl-4-FC₆H₃— | DL |
| 3-Cl-4-BrC₆H₃— | L |
| 3,4-Br₂C₆H₃— | D |
| 3-F-4-CH₃C₆H₃— | DL |
| 3-CH₃-4-CH₃OC₆H₃— | D |
| 3,4-(HO)₂C₆H₃— | D |
| 3-Cl-4-HOC₆H₃— | L |
| 2-F-4-HOC₆H₃— | DL |
| 2-F-4-CH₃OC₆H₃— | DL |
| 3,5-(CH₃O)₂C₆H₃— | D |
| 3-CH₃O-4-HOC₆H₃— | D |
| 3-Br-5-HOC₆H₃— | L |
| 3-H₂N-4-HOC₆H₃— | D |
| 3-H₂N-4-CH₃OC₆H₃— | DL |
| 3-CH₃-4-H₂NC₆H₃— | D |

EXAMPLE 26

7-(2-Cyanoacetamido)-3-methyl-4-(tetrazol-5-yl)-Δ³-cephem

To a stirred suspension of 7-amino-3-methyl-4-(tetrazol-5-yl)-Δ³-cephem tosylate salt (576 mg.) in methylene chloride (20 ml.) under nitrogen, is added triethylamine (450 mg.). After stirring for 20 min. at room temperature, this solution is then treated with the N-hydroxysuccinimide ester of cyanoacetic acid (470 mg.) all in one portion. After stirring overnight, under nitrogen, the reaction mixture is poured into water (30 ml.) and the pH of the aqueous phase is adjusted to 8.0. The methylene chloride layer is separated off. The aqueous phase is acidified to pH 2, and then extracted with ethyl acetate. The ethyl acetate is washed with water, dried (sodium sulfate) and the solvent removed under vacuum. Trituration of the residue with dry ether gives the product as a pale yellow solid (55 mg.).

NMR (DMSOd₆): δ = 5.7(q) 1H; 5.2(d) 1H; 3.8(s) 2H; 3.6(s) 2H and 2.0 (d) 6H.

EXAMPLE 27

7-(2-Carboxyphenylacetamido)-3-methyl-4-(tetrazol-5-yl)-Δ³-cephem sodium salt

Phenyl malonic acid (0.79 g.) is dissolved in distilled water (25 ml) and the pH of the solution adjusted to 6.0 by adding 2N sodium hydroxide solution. A solution of 7-amino-3-methyl-4-(tetrazol-5yl)-Δ³-cephem (0.65 g.)

in 10 ml. distilled water (pH adjusted to 6 by addition of 2N sodium hydroxide solution) is then added, and the reaction mixture cooled to 0° C. 1-Ethyl-3-(3-dimethylaminoprop-1-yl)carbodiimide (1.6 g.) is added and the solution stirred to 3.5 hrs., during which time the pH is maintained in the range 6.1 to 6.3 by the dropwise addition of dilute hydrochloric acid. At this point, the pH is raised to 7.3 by the addition of saturated sodium bicarbonate solution, and the reaction mixture is extracted with ethyl acetate. The extract is discarded. The aqueous phase is then acidified to pH 3 using 0.4M phosphoric acid, and again extracted with ethyl acetate (two 50 ml. portions). The latter extract is dried, and concentrated to a volume of about 25 ml. To this solution is then added a solution of sodium 2-ethylhexanoate (1 g.) in 20 ml. of ethyl acetate. The precipitate which forms is filtered to give 0.75 g. of the disodium salt of 7-(2-carboxy-2-phenylacetamido)-3methyl-4-(tetrazol-5-yl)-$\Delta^3$-cephem. The infrared spectrum of the product (KBr disc) shows absorptions at 1760 cm$^{-1}$ ($\beta$-lactam carbonyl), 1660 cm$^{-1}$ (amide I band) and 1600 cm$^{-1}$ (carboxylate carbonyl).

NMR (D$_2$O): $\delta$ = 7.4(m) 5H; 5.7(d) 1H; 5.2(d) 1H; 3.4(m) 2H and 1.9 (s) 3H.

EXAMPLE 28

Substituting 2-thienyl malonic acid for phenyl malonic acid in the procedure of Example 27, leads to the synthesis of 7-[$\alpha$-(2-thienyl)-$\alpha$-carboxyacetamido]-3-methyl-4-(tetrazol-5-yl)-$\Delta^3$-cephem.

NMR (DMSOd$_6$): $\delta$ = 2.1(s) 3H; 3.3(m) 2H; 5(s) 1H; 5.6(m) 1H; 6.8–7.5 (m) 3H.

IR (KBr disc) $\gamma_{max}$ 1770 cm$^{-1}$ ($\beta$-lactam carbonyl); 1670 cm$^{-1}$ (—CONH—).

Similarly, by employing the appropriate malonic acid derivative and repeating the procedure of Example 27, the following compounds are prepared:

Ar—CHCONH
     |
    CO$_2$H
(structure of cephem with S, N, CH$_3$, and tetrazole ring NH, N=N)

Ar
2-ClC$_6$H$_4$—
4-ClC$_6$H$_4$—
3-BrC$_6$H$_4$—
2-FC$_6$H$_4$—
4-FC$_6$H$_4$—
4-CH$_3$OC$_6$H$_4$—
2-CH$_3$C$_6$H$_4$—
4-CH$_3$C$_6$H$_4$—
4-HOC$_6$H$_4$—
4-H$_2$NC$_6$H$_4$—
2,4-Cl$_2$C$_6$H$_3$—
3,4-F$_2$C$_6$H$_3$—
3-F-4-BrC$_6$H$_3$—
3-Cl-4-HOC$_6$H$_3$—
3,4-(CH$_3$O)$_2$C$_6$H$_3$—
3-F-4-CH$_3$OC$_6$H$_3$—
3-Cl-4-H$_2$NC$_6$H$_3$—
3-thienyl-

EXAMPLE 29

7-Phenylacetamido-3-methyl-4-(tetrazol-5-yl)-$\Delta^3$-cephem

Phenacetyl chloride (2.3 g.) in acetone (5 ml.) is added dropwise to a stirred solution of 7-amino-3-methyl-4-(tetrazol-5-yl)-$\Delta^3$-cephem sodium salt (1.31 g.) in aqueous acetone (20 ml.) over 20 min. at room temperature. Sodium hydroxide (2N) is added simultaneously to keep pH at 8±0.5. The solution, after the addition, is stirred for a further 15 min. The acetone is removed under reduced pressure and the pH of the aqueous solution adjusted to 2 with 2N hydrochloric acid. The suspension is extracted with ethyl acetate, the organic solution dried (MgSO$_4$) and evaporated under reduced pressure to leave an oil which solidifies after trituration with ether (440 mg.).

NMR (DMSOd$_6$): $\delta$ = 9.0(d) 1H; 7.2(s) 5H; 5.6(q) 1H; 5.2(d) 1H; 3.5(s) 4H and 2.0(s) 3H.

EXAMPLE 30

7-Phenoxyacetamido-3-methyl-4-(tetrazol-5-yl)-$\Delta^3$-cephem

Phenoxyacetyl chloride (2.56 g.) in acetone (5ml.) is added dropwise to a stirred solution of 7-amino-3l-methyl-4-(tetrazol-5-yl)-$\Delta$ $^3$-cephem sodium salt (1.31 g.) in aqueous acetone (30 ml.) over 20 min. at room temperature. Sodium hydroxide (2N) is added simultaneously to keep the pH at 8±0.5. The solution is the allowed to stir for a further 15 min. The acetone is removed under reduced pressure and the pH of the aqueous solution adjusted to 2 with hydrochloric acid (2N). The suspension is extracted with ethyl acetate and the organic solution dried (MgSO$_4$). Evaporation and trituration of the residue gives the desired product as a solid (370 mg.).

NMR (DMSOd$_6$): $\delta$ = 9.0(d) 1H; 7.0(m) 5H; 5.6(q) 1H; 5.2(d) 1H; 4.6(s) 2H; 3.8(s) 2H and 2.0(s) 2H.

EXAMPLE 31

Employing the procedure of Example 29 and 30, and starting with the requisite reagents, the following $\Delta^3$-cephems are synthesized:

7-Bromoacetamido-3-methyl-4-(tetrazol-5-yl)-$\Delta^3$-cephem,

NMR (DMSOd$_6$): $\delta$ = 2.15(s) 3H; 3.7(m) 2H; 4.1(s) 2H; 5.4(d) 1H and 5.2 (m) 1H;

7-($\alpha$-azido-$\alpha$-phenylacetamido)-3-methyl-4-(tetrazol-5-yl)-$\Delta^3$-cephem, NMR (DMSOd$_6$): $\delta$ = 9.2(s) 1H; 7.35(s) 5H; 5.6(s) 1H; 5.15(q) 2H; 3.58 (s) 2H and 1.98(s) 3H;

7-[$\alpha$-(tetrazol-5-yl)acetamido]-3-methyl-4-(tetrazol-5l-yl)-$\Delta^3$-cephem, NMR (DMSOd$_6$): $\delta$ = 2.0(s) 3H; 3.6(s) 2H; 5.05–5.15(d) 1H; 5.15(s) 2H; 5.5–5.8(q) 1H and 9.5(s) 1H;

7-($\alpha$-phenylthioacetamido-3-methyl-4-(tetrazol-5-yl)-$\Delta^3$-cephem,

NMR (DMSOd$_6$): $\delta$ = 9.18(d) 1H; 7.23(m) 5H; 5.63(q) 1H; 5.35(d) 1H; 3.77(s) 2H; 3.6(m) 2H and 2.03(s) 3H;

7-[$\alpha$-(2,6-dimethoxyphenyl)carboxamido]-3-methyl-4-(tetrazol-5-yl)-$\Delta^3$-cephem, NMR (DMSOd$_6$): $\delta$ = 2.0(s) 3H; 3.6(s) 2H; 3.7(s) 6H; 5.05–5.15(d) 1H; 5.5–5.8(q) 1H; 6.5–6.7(d) 2H and 7.0–7.3(m) 1H;

7-(2-thienylglyoxylamido)-3-methyl-4-(tetrazol-5-yl)-$\Delta^3$-cephem,

NMR (DMSOD$_6$): $\delta$ = 2.0(s) 3H; 3.6(s) 2H; 5.1–5.15(d) 1H; 5.4–5.7(q) 1H; 7.05–7.15(m) 1H and 7.8–8.1(m) 2H; and 7-[$\alpha$-(2-thienyl)acetamido]-3-methyl-4-(tetrazol-5-yl)-$\Delta^3$-cephem, NMR (DMSOD₆): δ = 2.0(s) 3H; 3.6(s) 2H; 3.8(s) 2H; 5.1–5.15(d) 1H; 5.5–5.8(q) 1H; 6.95–7.0(d) 2H and 7.1–7.2(m) 1H.

EXAMPLE 32

Starting with the appropriate acid chloride and 7-amino-3-methyl-4-(tetrazol-5-yl)-Δ³-cephem and employing the procedure of Examples 29 and 30, the following congeners are prepared:

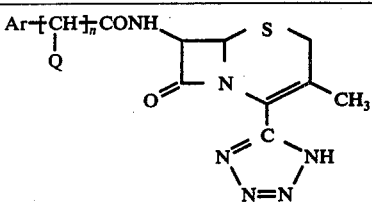

| Ar | Q | n |
|---|---|---|
| C₆H₅— | — | 0 |
| 2-ClC₆H₄— | — | 0 |
| 4-ClC₆H₄— | — | 0 |
| 2,3-Cl₂C₆H₃— | — | 0 |
| 3,4-Cl₂C₆H₃— | — | 0 |
| 3-FC₆H₄— | — | 0 |
| 4-FC₆H₄— | — | 0 |
| 3,5-F₂C₆H₃— | — | 0 |
| 4-BrC₆H₄— | — | 0 |
| 3,4-Br₂C₆H₃— | — | 0 |
| 3-HOC₆H₄— | — | 0 |
| 4-HOC₆H₄— | — | 0 |
| 4-H₂NC₆H₄— | — | 0 |
| 3-Cl-4-HOC₆H₃— | — | 0 |
| 3-F-4-HOC₆H₃— | — | 0 |
| 4-CH₃OC₆H₄— | — | 0 |
| 3-Br-4-CH₃OC₆H₃— | — | 0 |
| 3-CH₃-4-HOC₆H₃— | — | 0 |
| 3-CH₃-4-ClC₆H₃— | — | 0 |
| 2-thienyl- | — | 0 |
| 3-thienyl- | — | 0 |
| 2-ClC₆H₄— | N₃ | 1 |
| 4-ClC₆H₄— | N₃ | 1 |
| 2,4-Cl₂C₆H₃— | N₃ | 1 |
| 4-FC₆H₄— | N₃ | 1 |
| 3,5-F₂C₆H₃— | N₃ | 1 |
| 4-BrC₆H₄— | N₃ | 1 |
| 4-HOC₆H₄— | N₃ | 1 |
| 3-HOC₆H₄— | N₃ | 1 |
| 4-CH₃OC₆H₄— | N₃ | 1 |
| 3-F-4-HOC₆H₃— | N₃ | 1 |
| 3-Cl-4-HOC₆H₃— | N₃ | 1 |
| 3-Br-4-CH₃OC₆H₃— | N₃ | 1 |
| 4-H₂NC₆H₄— | N₃ | 1 |
| 3-Cl-4-H₂NC₆H₃— | N₃ | 1 |
| 4-CH₃C₆H₄— | N₃ | 1 |
| 3-CH-4-CH₃OC₆H₃— | N₃ | 1 |
| 2-thienyl- | N₃ | 1 |
| 3-thienyl- | N₃ | 1 |

EXAMPLE 33

7-[α-Hydroxy-α-(2-thienyl)acetamido]-3-methyl-4-(tetrazol-5-yl)-Δ³-cephem 7-(2-Thienylglyoxylamido)-3-methyl-4-(tetrazol-5-yl)-Δ³-cephem (1.50 g.) in water (30 ml.) is converted to the sodium salt with 2N sodium hydroxide. This solution is cooled in ice and anhydrous sodium acetate (1.53 g.) is added. Sodium borohydride (276 mg.) is then added in small portions over a 45 min. period. The pH is kept at 8, by adding glacial acetic acid alternately with sodium borohydride. After the additions, the pH is kept at 8 for 45 min. with the ice bath removed. The solution is layered with ethyl acetate and the pH adjusted to 2 with 40% phosphoric acid. The organic layer is separated, washed with water, dried (Na₂SO₄), filtered and concentrated in vacuo until solids crystallize. The product is filtered, washed with dry ether and dried under vacuum, 360 mg.

NMR (DMSOd₆): δ = 7.2(m) 1H; 7.0, 2H; 5.4(m) 1H; 5.0(s) 2H; 3.5, 2H and 2.0(s) 3H.

EXAMPLE 34

7-[2-(2-methyl-1,3,4-thiadiazol-5-yl-thio-acetamido)]-3-methyl-4-(tetrazol-5-yl)-Δ³-cephem Triethylamine (0.2 ml.) is added to a cold 0° C. suspension of 7-(2-bromoacetamido)-3-methyl-4-(tetrazol-5-yl)-Δ³-cephem (0.5 g.) in methylene chloride (15 ml.). To the resultant pale yellow solution is added a slurry of 2-methyl-1,3,4-thiadiazole-5-thiol (0.19 g.) and the solution stirred at 0° C. After 2 hrs. the product which has precipitated is collected by filtration (0.3 g.).

NMR (DMSOd₆): δ = 9.3(d) 1H; 5.6(m) 1H; 5.2(d) 1H; 4.15(s) 2H; 3.6 (s) 2H; 2.7(s) 3H and 2.05(s) 3H.

EXAMPLE 35

The procedure of Example 34 is repeated, starting with 7-(2-bromoacetamido)-3-methyl-4-(tetrazol-5-yl)-Δ³-cephem and 1-methyl-5-mercaptotetrazole (Lieber, et al., Can. J. Chem., 37, 101 [1959]) to provide 7-[α-(1-methyltetrazol-5-ylthio)acetamido]-3-methyl-4-(tetrazol-5-yl)-Δ³-cephem.

NMR (DMSOd₆): δ = 9.28(d) 1H; 5.6(q) 1H; 5.24(d) 1H; 4.13(s) 2H; 3.95(s) 3H; 3.59(m) 2H and 2.01(s) 3H.

EXAMPLE 36

Again, the procedure of Example 34 is repeated, employing 4-mercaptopyridine and 7-(2-bromoacetamido)-3-methyl-4-(tetrazol-5-yl)-Δ³-cephem to give 7-[2-(4-pyridylthio)acetamido]-3-methyl-4-(tetrazol-5-yl)-Δ³-cephem.

NMR (DMSOd₆): δ = 9.32(d) 1H; 8.41(m) 2H; 7.33(m) 2H; 5.7–5.6(q) 1H; 5.25(d) 1H; 3.95(d) 2H; 3.6(m) 2H and 2.03(s) 3H.

EXAMPLE 37

7-(2',2',2'-Trichloroethoxycarboxamido)-3-acetoxymethyl-4-[N-(p-methoxybenzyl)carbamoyl]-Δ³-cephem

A.

7-(2',2',2'-Trichloroethoxycarboxamido)-3-acetoxymethyl-Δ³-cephem-4-carboxylic acid Sodium bicarbonate (300 g.) is added portionwise to a stirred slurry of 7-amino-cephalosporanic acid (408 g.) in aqueous acetone (2:1, 5 liters: 2.5 liters). 2',2',2'-Trichloroethyl chloroformate (350 g.) is then added dropwise over 45 min. and the mixture stirred for a further 5 hrs. at room temperature.

The acetone is removed in vacuo, and the aqueous solution is then diluted to 10 liters with distilled water. The pH of the solution is adjusted to 2 with 50% hydrochloric acid, and the mixture extracted with ethyl acetate (5 × 1.5 liters). The combined organic layers are washed with water (2 × 2 liters), dried (MgSO₄) and the solution concentrated to a volume of 1.5 liters.

The concentrate is slowly added to petroleum ether (b.p 60°–80° C., 15 liters) and the precipitated solid washed with petroleum ether (b.p. 30°–40° C 2 × 2 liters). The precipitate is dried in vacuo at 45° C. to furnish 7-(2',2',2'-trichloroethoxycarbonyl)-amino-3-acetoxymethyl-Δ³-cephem-4-carboxylic acid as a white solid (490 g.).

NMR (DMSOd₆): δ = 10(d) 1H; 5.5(q) 1H; 5.1(d) 1H; 4.8(q) 2H; 4.8(s) 2H; 3.5(s) 2H and 2.0(s) 3H.

B.
7-(2',2',2'-Trichloroethoxycarboxamido)-3-acetoxymethyl-4-[N-(p-methoxybenzyl)-carbamoyl]-Δ³-cephem Starting with the acid of Example 37A and following the procedure of Example 1B, the desired product is prepared in moderate yield.

NMR (CDCl₃): δ = 2.0(s) 3H; 3.4(s) 2H; 3.8(s) 3H; 4.45(d) 2H; 4.75 (s) 2H; 4.9(m) 3H; 5.5(q) 1H; 6.2(b) 1H and 7.1(q) 4H.

EXAMPLE 38

7-(2',2',2'-Trichloroethoxycarboxamido)-3-(2-methyl-1,3,4-thiadiazol-5-ylthiomethyl)-4-[N-(p-methoxybenzyl)-carbamoyl]-Δ³-cephem

A.
7-(2',2',2'-Trichloroethoxycarboxamido)-3-(2-methyl-1,3,4-thiadiazol-5-ylthiomethyl)-Δ³-cephem-4-carboxylic acid Following the procedure of Example 37A, but employing as the cephem 7-amino-3-(2-methyl-1,3,4-thiadiazol-5-ylthiomethyl)-Δ³-cephem-4-carboxylic acid (U.S. Pat. No. 3,641,021), the desired product is prepared.

NMR (CDCl₃): δ = 5.4(m) 2H; 5.1(d) 1H; 4.85(s) 2H; 4.4(q) 2H; 3.7(s) 2H and 2.7(s) 3H.

B.
7-(2',2',2'-Trichloroethoxycarboxamido)-3-(2-methyl-1,3,4-thiadiazol-5-ylthiomethyl)-4-[N-(p-methoxybenzyl)carbamoyl]-Δ³-cephem Employing the product of Example 38A and using the procedure of Example 37B and 1B, the desired intermediate product is synthesized.

NMR (CDCl₃): δ = 7.0(q) 2H; 6.1(m) 1H; 5.4(q) 1H; 4.9(d) 1H; 4.7(s) 2H; 4.4(m) 4H; 3.75(s) 3H and 3.6(s) 2H.

EXAMPLE 39

The procedure of Example 37 is repeated, starting with the appropriate 2',2',2'-trihaloethyl chloroformate, Δ³-cephem-4-carboxylic acid and amine, to give the following analogs:

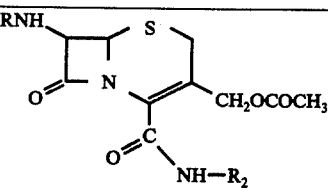

| R | R₂ |
|---|---|
| Cl₃CCH₂OCO— | 4-C₆H₅CH₂OC₆H₄CH₂— |
| Cl₃CCH₂OCO— | 4-C₆H₅CH₂O-3-FC₆H₃CH₂— |
| Cl₃CCH₂OCO— | 2-Cl-4-CH₃OC₆H₃CH₂— |
| Cl₃CCH₂OCO— | 3-Cl-4-HOC₆H₃CH₂— |
| Cl₃CCH₂OCO— | 3,4-(CH₃O)₂C₆H₃CH₂— |
| Cl₃CCH₂OCO— | 4-HOC₆H₄CH(CH₃)— |
| Cl₃CCH₂OCO— | 2-Br-4-CH₃OC₆H₃CH₂— |
| Cl₃CCH₂OCO— | 4-CH₃OC₆H₄CH(φ)— |
| Cl₃CCH₂OCO— | 2,4-(CH₃O)₂C₆H₃CH(CH₃)— |
| Cl₃CCH₂OCO— | 4-CH₃OC₆H₄CH(n-C₃H₇)— |
| Cl₃CCH₂OCO— | 3-CH₃-4-CH₃OC₆H₃CH₂— |
| Cl₃CCH₂OCO— | 4-C₂H₅CO₂C₆H₄CH₂— |
| Cl₃CCH₂OCO— | 3-F-4-CH₃CO₂C₆H₃CH₂— |
| Cl₃CCH₂OCO— | 4-HOC₆H₄CH(φ)— |
| Cl₃CCH₂OCO— | 3-I-4-CH₃OC₆H₃CH₂— |
| Cl₃CCH₂OCO— | 4-(i-C₃H₇CO₂)C₆H₄CH₂— |
| Cl₃CCH₂OCO— | 3,4-(C₆H₅CH₂O)₂C₆H₃CH₂— |
| Cl₃CCH₂OCO— | 4-CH₃OC₆H₄CH(CH₃)— |
| Cl₃CCH₂OCO— | 4-CH₃OC₆H₄CH(C₂H₅)— |

-continued

| R | R₂ |
|---|---|
| Cl₃CCH₂OCO— | 3-F-4-CH₃OC₆H₃CH₂— |
| Cl₃CCH₂OCO— | 3-Cl-4-CH₃OC₆H₃CH(CH₃)— |
| Cl₃CCH₂OCO— | 4-HOC₆H₄CH₂— |
| Cl₃CCH₂OCO— | 4-CH₃CO₂C₆H₄CH₂— |
| Cl₃CCH₂OCO— | 3-F-4-HOC₆H₃CH₂— |
| Cl₃CCH₂OCO— | 3-CH₃O-4-CH₃CO₂C₆H₄CH₂— |
| Cl₃CCH₂OCO— | 4-C₆H₅CH₂OC₆H₃CH(CH₃)— |
| Cl₃CCH₂OCO— | 3-Cl-4-C₆H₅CH₂OC₆H₃CH₂— |
| Cl₃CCH₂OCO— | 3,4-(C₂H₅CO₂)₂C₆H₃CH₂— |
| Cl₃CCH₂OCO— | 4-(n-C₃H₇CO₂)C₆H₄CH₂— |
| Cl₃CCH₂OCO— | 4-(i-C₃H₇CO₂)C₆H₄CH(C₂H₅)— |
| Cl₃CCH₂OCO— | 2-furylmethyl- |
| Cl₃CCH₂OCO— | 5-methyl-2-furylmethyl- |
| Cl₃CCH₂OCO— | 2-thienylmethyl- |
| Cl₃CCH₂OCO— | 5-methyl-2-thienylmethyl- |
| Cl₃CCH₂OCO— | 1-(2-furyl)ethyl- |
| Cl₃CCH₂OCO— | 1-(5-methyl-2-furyl)ethyl- |
| Br₃CCH₂OCO— | 4-C₆H₅CH₂OC₆H₄CH₂— |
| Br₃CCH₂OCO— | 4-C₆H₅CH₂O-3-FC₆H₃CH₂— |
| Br₃CCH₂OCO— | 2-Cl-4-CH₃OC₆H₃CH₂— |
| Br₃CCH₂OCO— | 4-Cl-4-HOC₆H₃CH₂— |
| Br₃CCH₂OCO— | 2-Br-4-CH₃OC₆H₃CH₂— |
| Br₃CCH₂OCO— | 2,4-(CH₃O)₂C₆H₃CH(CH₃)— |
| Br₃CCH₂OCO— | 4-C₂H₅CO₂C₆H₄CH₂— |
| Br₃CCH₂OCO— | 3-CH₃-4-CH₃OC₆H₃CH₂— |
| Br₃CCH₂OCO— | 3-F-4-CH₃CO₂C₆H₃CH₂— |
| Br₃CCH₂OCO— | 3-I-4-CH₃OC₆H₃CH₂— |
| Br₃CCH₂OCO— | 4-(i-C₃H₇CO₂)C₆H₄CH₂— |
| Br₃CCH₂OCO— | 3,4-(C₆H₅CH₂O)₂C₆H₃CH₂— |
| Br₃CCH₂OCO— | 4-CH₃OC₆H₄CH(CH₃)— |
| Br₃CCH₂OCO— | 4-CH₃OC₆H₄CH(C₂H₅)— |
| Br₃CCH₂OCO— | 3,4-(CH₃O)₂C₆H₃CH₂— |
| Br₃CCH₂OCO— | 3-F-4-CH₃OC₆H₃CH₂— |
| Br₃CCH₂OCO— | 3-Cl-4-CH₃OC₆H₃CH(CH₃)— |
| Br₃CCH₂OCO— | 4-HOC₆H₄CH₂— |
| Br₃CCH₂OCO— | 4-HOC₆H₄CH(CH₃)— |
| Br₃CCH₂OCO— | 4-CH₃CO₂C₆H₄CH₂— |
| Br₃CCH₂OCO— | 3-Cl-4-HOC₆H₃CH₂— |
| Br₃CCH₂OCO— | 3-Cl-4-CH₃CO₂C₆H₃CH₂— |
| Br₃CCH₂OCO— | 4-C₆H₅CH₂OC₆H₃CH(CH₃)— |
| Br₃CCH₂OCO— | 3-Cl-4-C₆H₅CH₂OC₆H₃CH₂— |
| Br₃CCH₂OCO— | 2-F-4-HOC₆H₃CH₂— |
| Br₃CCH₂OCO— | 3,4-(C₂H₅CO₂)₂C₆H₃CH₂— |
| Br₃CCH₂OCO— | 4-(n-C₃H₇CO₂)C₆H₄CH₂— |
| Br₃CCH₂OCO— | 2-furylmethyl- |
| Br₃CCH₂OCO— | 5-methyl-2-furylmethyl- |
| Br₃CCH₂OCO— | 2-thienylmethyl- |
| Br₃CCH₂OCO— | 1-(2-furyl)ethyl- |
| Br₃CCH₂OCO— | 1-(5-methyl-2-furyl)ethyl- |

EXAMPLE 40

The procedure of Example 38 is repeated, starting with the requisite reagents, to give the following analogs:

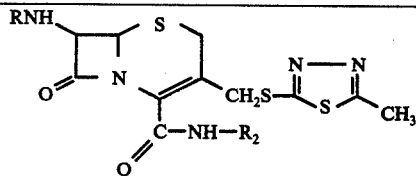

| R | R₂ |
|---|---|
| Cl₃CCH₂OCO— | 4-C₆H₅CH₂OC₆H₄CH₂— |
| Cl₃CCH₂OCO— | 4-C₆H₅CH₂O-3-FC₆H₃CH₂— |
| Cl₃CCH₂OCO— | 2-Cl-4-CH₃OC₆H₃CH₂— |
| Cl₃CCH₂OCO— | 3-Cl-4-HOC₆H₃CH₂— |
| Cl₃CCH₂OCO— | 3,4-(CH₃O)₂C₆H₃CH₂— |
| Cl₃CCH₂OCO— | 4-HOC₆H₄CH(CH₃)— |
| Cl₃CCH₂OCO— | 2-Br-4-CH₃OC₆H₃CH₂— |
| Cl₃CCH₂OCO— | 4-CH₃OC₆H₄CH(φ)— |
| Cl₃CCH₂OCO— | 2,4-(CH₃O)₂C₆H₃CH(CH₃)— |
| Cl₃CCH₂OCO— | 4-CH₃OC₆H₄CH(n-C₃H₇)— |
| Cl₃CCH₂OCO— | 3-CH₃-4-CH₃OC₆H₃CH₂— |
| Cl₃CCH₂OCO— | 4-C₂H₅CO₂C₆H₄CH₂— |

-continued

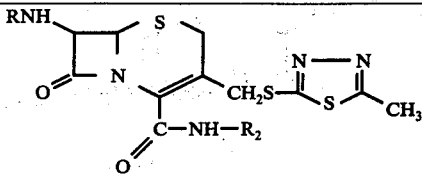

| R | R₂ |
|---|---|
| Cl₃CCH₂OCO— | 3-F-4-CH₃CO₂C₆H₃CH₂— |
| Cl₃CCH₂OCO— | 4-HOC₆H₄CH(φ)- |
| Cl₃CCH₂OCO— | 3-I-4-CH₃OC₆H₃CH₂— |
| Cl₃CCH₂OCO— | 4-(i-C₃H₇CO₂)C₆H₄CH₂— |
| Cl₃CCH₂OCO— | 3,4-(C₆H₅CH₂O)₂C₆H₃CH₂— |
| Cl₃CCH₂OCO— | 4-CH₃OC₆H₄CH(CH₃)— |
| Cl₃CCH₂OCO— | 4-CH₃OC₆H₄CH(C₂H₅)— |
| Cl₃CCH₂OCO— | 3-F-4-CH₃CC₆H₃CH₂— |
| Cl₃CCH₂OCO— | 3-Cl-4-CH₃OC₆H₃CH(CH₃)— |
| Cl₃CCH₂OCO— | 4-HOC₆H₄CH₂— |
| Cl₃CCH₂OCO— | 4-CH₃CO₂C₆H₄CH₂— |
| Cl₃CCH₂OCO— | 3-F-4-HOC₆H₃CH₂— |
| Cl₃CCH₂OCO— | 3-CH₃O-4-CH₃CO₂C₆H₄CH₂— |
| Cl₃CCH₂OCO— | 4-C₆H₅CH₂OC₆H₃CH(CH₃)— |
| Cl₃CCH₂OCO— | 3-Cl-4-C₆H₅CH₂OC₆H₃CH₂— |
| Cl₃CCH₂OCO— | 3,4-(C₂H₅CO₂)₂C₆H₃CH₂— |
| Cl₃CCH₂OCO— | 4-(n-C₃H₇CO₂)C₆H₄CH₂— |
| Cl₃CCH₂OCO— | 4-(i-C₃H₇CO₂)C₆H₄CH(C₂H₅) |
| Cl₃CCH₂OCO— | 2-furylmethyl- |
| Cl₃CCH₂OCO— | 5-methyl-2-furylmethyl- |
| Cl₃CCH₂OCO— | 2-thienylmethyl- |
| Cl₃CCH₂OCO— | 5-methyl-2-thienylmethyl- |
| Cl₃CCH₂OCO— | 1-(2-furyl)ethyl- |
| Cl₃CCH₂OCO— | 1-(5-methyl-2-furyl)ethyl- |
| Br₃CCH₂OCO— | 4-C₆H₅CH₂OC₆H₄CH₂— |
| Br₃CCH₂OCO— | 4-C₆H₅CH₂O-3-FC₆H₃CH₂— |
| Br₃CCH₂OCO— | 2-Cl-4-CH₃OC₆H₃CH₂— |
| Br₃CCH₂OCO— | 4-Cl-4-HOC₆H₃CH₂— |
| Br₃CCH₂OCO— | 2-Br-4-CH₃OC₆H₃CH₂— |
| Br₃CCH₂OCO— | 2,4-(CH₃O)₂C₆H₃CH(CH₃)— |
| Br₃CCH₂OCO— | 4-C₂H₅CO₂C₆H₄CH₂— |
| Br₃CCH₂OCO— | 3-CH₃-4-CH₃OC₆H₃CH₂— |
| Br₃CCH₂OCO— | 3-F-4-CH₃CO₂C₆H₃CH₂— |
| Br₃CCH₂OCO— | 3-I-4-CH₃OC₆H₃CH₂— |
| Br₃CCH₂OCO— | 4-(i-C₃H₇CO₂)C₆H₄CH₂— |
| Br₃CCH₂OCO— | 3,4-(C₆H₅CH₂O)₂C₆H₃CH₂— |
| Br₃CCH₂OCO— | 4-CH₃OC₆H₄CH(CH₃)— |
| Br₃CCH₂OCO— | 4-CH₃OC₆H₄CH(C₂H₅)— |
| Br₃CCH₂OCO— | 3,4-(CH₃O)₂C₆H₃CH₂— |
| Br₃CCH₂OCO— | 3-F-4-CH₃OC₆H₃CH₂— |
| Br₃CCH₂OCO— | 3-Cl-4-CH₃OC₆H₃CH(CH₃)— |
| Br₃CCH₂OCO— | 4-HOC₆H₄CH₂— |
| Br₃CCH₂OCO— | 4-HOC₆H₄CH(CH₃)— |
| Br₃CCH₂OCO— | 4-CH₃CO₂C₆H₄CH₂— |
| Br₃CCH₂OCO— | 3-Cl-4-HOC₆H₃CH₂— |
| Br₃CCH₂OCO— | 3-Cl-4-CH₃CO₂C₆H₃CH₂— |
| Br₃CCH₂OCO— | 4-C₆H₅CH₂OC₆H₃CH(CH₃)— |
| Br₃CCH₂OCO— | 3-Cl-4-C₆H₅CH₂OC₆H₃CH₂— |
| Br₃CCH₂OCO— | 2-F-4-HOC₆H₃CH₂— |
| Br₃CCH₂OCO— | 3,4-(C₂H₅CO₂)₂C₆H₃CH₂— |
| Br₃CCH₂OCO— | 4-(n-C₃H₇CO₂)C₆H₄CH₂— |
| Br₃CCH₂OCO— | 2-furylmethyl- |
| Br₃CCH₂OCO— | 5-methyl-2-furylmethyl- |
| Br₃CCH₂OCO— | 2-thienylmethyl- |
| Br₃CCH₂OCO— | 1-(2-furyl)ethyl- |
| Br₃CCH₂OCO— | 1-(5-methyl-2-furyl)ethyl- |

EXAMPLE 41

7-(2',2',2'-Trichloroethoxycarboxamido)-3-acetoxymethyl-4-[1-(p-methoxybenzyl)tetrazol-5-yl]-Δ³-cephem Phosphorous pentachloride (1.68 g., 8 mmole) is added to a stirred solution of 7-(2',2',2'-trichloroethoxycarboxamido)-3-acetoxymethyl-4-[N-(p-methoxybenzyl) carbamoyl]-Δ³-cephem (2.26 g., 4 mmole) and pyridine (0.64 g., 8 mmole) in dry, ethanol-free chloroform (30 ml.) at 0.5°-5° C. After 30 min., NMR indicated that the amide had completely reacted (disappearance of the 2 proton doublet at δ4.45). A solution of tetramethylguanidinium azide (6.3 g., 40 mmole) in dry ethanol-free chloroform (20 ml.) is added dropwise over a period of 10 min. to the cooled solution. After a further 10 min. the icebath is removed and the reaction mixture is stirred at ambient temperature for 30 min. The reaction mixture is washed with water, aqueous sodium bicarbonate solution (3 x), 6N hydrochloric acid (3 x), water, and dried over magnesium sulphate. Evaporation of the solvent affords the crude product as a pale brown solid (1.5 g.). Column chromatography on silica gel commencing with hexane as eluent and adding gradually increasing proportions of ether, finally eluting with 100% ether affords the pure (by tlc) product.

NMR (DMSOd₆) δ = 1.8(s) 3H; 3.6(q) 2H; 3.9(s) 3H; 4.2(q) 2H; 4.8(s) 2H; 5.1(d) 1H; 5.6(m) 3H; 6.3(d) 1H and 7.4(q) 4H.

EXAMPLE 42

7-(2',2',2'-Trichloroethoxycarboxamido)-3-(2-methyl-1,3,4-thiadiazol-5-ylthiomethyl)-4-[1-(p-methoxybenzyl)tetrazol-5-yl]-Δ³-cephem Starting with the cephem of Example 38B and following the procedure of Example 41, the desired product is synthesized.

NMR (CDCl₃): δ = 7.0(q) 4H; 5.5(s) 2H; 5.4(m) 2H; 4.7(s) 2H; 4.2(m) 2H; 5.75(s) 3H and 5.65(m) 2H.

EXAMPLE 43

Starting with the intermediates of Example 39, and employing the procedure of Example 41, the following Δ³-cephems are synthesized:

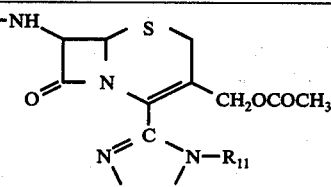

| R | R₁₁ |
|---|---|
| Cl₃CCH₂OCO— | 4-C₆H₅CH₂OC₆H₄CH₂— |
| Cl₃CCH₂OCO— | 4-C₆H₅CH₂O-3-FC₆H₃CH₂— |
| Cl₃CCH₂OCO— | 2-Cl-4-CH₃OC₆H₃CH₂— |
| Cl₃CCH₂OCO— | 3-Cl-4-HOC₆H₃CH₂— |
| Cl₃CCH₂OCO— | 3,4-(CH₃O)₂C₆H₃CH₂— |
| Cl₃CCH₂OCO— | 4-HOC₆H₄CH(CH₃)— |
| Cl₃CCH₂OCO— | 2-Br-4-CH₃OC₆H₃CH₂— |
| Cl₃CCH₂OCO— | 4-CH₃OC₆H₄CH(φ)— |
| Cl₃CCH₂OCO— | 2,4-(CH₃O)₂C₆H₃CH(CH₃)— |
| Cl₃CCH₂OCO— | 4-CH₃OC₆H₄CH(n-C₃H₇)— |
| Cl₃CCH₂OCO— | 3-CH₃-4-CH₃OC₆H₃CH₂— |
| Cl₃CCH₂OCO— | 4-C₂H₅CO₂C₆H₄CH₂— |
| Cl₃CCH₂OCO— | 3-F-4-CH₃CO₂C₆H₃CH₂— |
| Cl₃CCH₂OCO— | 4-HOC₆H₄CH(φ)— |
| Cl₃CCH₂OCO— | 3-I-4-CH₃OC₆H₃CH₂— |
| Cl₃CCH₂OCO— | 4-(i-C₃H₇CO₂)C₆H₄CH₂— |
| Cl₃CCH₂OCO— | 3,4-(C₆H₅CH₂O)₂C₆H₃CH₂— |
| Cl₃CCH₂OCO— | 4-CH₃OC₆H₄CH(CH₃)— |
| Cl₃CCH₂OCO— | 4-CH₃OC₆H₄CH(C₂H₅)— |
| Cl₃CCH₂OCO— | 3-F-4-CH₃OC₆H₃CH₂— |
| Cl₃CCH₂OCO— | 3-Cl-4-CH₃OC₆H₃CH(CH₃)— |
| Cl₃CCH₂OCO— | 4-HOC₆H₄CH₂— |
| Cl₃CCH₂OCO— | 4-CH₃CO₂C₆H₄CH₂— |
| Cl₃CCH₂OCO— | 3-F-4-HOC₆H₃CH₂— |
| Cl₃CCH₂OCO— | 3-CH₃O-4-CH₃CO₂C₆H₄CH₂— |
| Cl₃CCH₂OCO— | 4-C₆H₅CH₂OC₆H₃CH(CH₃)— |
| Cl₃CCH₂OCO— | 3-Cl-4-C₆H₅CH₂OC₆H₃CH₂— |
| Cl₃CCH₂OCO— | 3,4-(C₂H₅CO₂)₂C₆H₃CH₂— |
| Cl₃CCH₂OCO— | 4-(n-C₃H₇CO₂)C₆H₄CH₂— |
| Cl₃CCH₂OCO— | 4-(i-C₃H₇CO₂)C₆H₄CH(C₂H₅) |
| Cl₃CCH₂OCO— | 2-furylmethyl- |
| Cl₃CCH₂OCO— | 5-methyl-2-furylmethyl- |
| Cl₃CCH₂OCO— | 2-thienylmethyl- |
| Cl₃CCH₂OCO— | 5-methyl-2-thienylmethyl- |
| Cl₃CCH₂OCO— | 1-(2-furyl)ethyl- |
| Cl₃CCH₂OCO— | 1-(5-methyl-2-furyl)ethyl- |
| Br₃CCH₂OCO— | 4-C₆H₅CH₂OC₆H₄CH₂— |
| Br₃CCH₂OCO— | 4-C₆H₅CH₂O-3-FC₆H₃CH₂— |
| Br₃CCH₂OCO— | 2-Cl-4-CH₃OC₆H₃CH₂— |
| Br₃CCH₂OCO— | 4-Cl-4-HOC₆H₃CH₂— |
| Br₃CCH₂OCO— | 2-Br-4-CH₃OC₆H₃CH₂— |
| Br₃CCH₂OCO— | 2,4-(CH₃O)₂C₆H₃CH(CH₃)— |
| Br₃CCH₂OCO— | 4-C₂H₅CO₂C₆H₄CH₂— |
| Br₃CCH₂OCO— | 3-CH₃-4-CH₃OC₆H₃CH₂— |

-continued

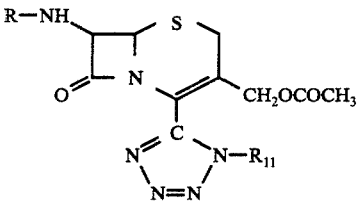

| R | $R_{11}$ |
|---|---|
| $Br_3CCH_2OCO-$ | $3\text{-}F\text{-}4\text{-}CH_3CO_2C_6H_3CH_2-$ |
| $Br_3CCH_2OCO-$ | $3\text{-}I\text{-}4\text{-}CH_3OC_6H_3CH_2-$ |
| $Br_3CCH_2OCO-$ | $4\text{-}(i\text{-}C_3H_7CO_2)C_6H_4CH_2-$ |
| $Br_3CCH_2OCO-$ | $3,4\text{-}(C_6H_5CH_2O)_2C_6H_3CH_2-$ |
| $Br_3CCH_2OCO-$ | $4\text{-}CH_3OC_6H_4CH(CH_3)-$ |
| $Br_3CCH_2OCO-$ | $4\text{-}CH_3OC_6H_4CH(C_2H_5)-$ |
| $Br_3CCH_2OCO-$ | $3,4\text{-}(CH_3O)_2C_6H_3CH_2-$ |
| $Br_3CCH_2OCO-$ | $3\text{-}F\text{-}4\text{-}CH_3OC_6H_3CH_2-$ |
| $Br_3CCH_2OCO-$ | $3\text{-}Cl\text{-}4\text{-}CH_3OC_6H_3CH(CH_3)-$ |
| $Br_3CCH_2OCO-$ | $4\text{-}HOC_6H_4CH_2-$ |
| $Br_3CCH_2OCO-$ | $4\text{-}HOC_6H_4CH(CH_3)-$ |
| $Br_3CCH_2OCO-$ | $4\text{-}CH_3CO_2C_6H_4CH_2-$ |
| $Br_3CCH_2OCO-$ | $3\text{-}Cl\text{-}4\text{-}HOC_6H_3CH_2-$ |
| $Br_3CCH_2OCO-$ | $3\text{-}Cl\text{-}4\text{-}CH_3CO_2C_6H_3CH_2-$ |
| $Br_3CCH_2OCO-$ | $4\text{-}C_6H_5CH_2OC_6H_3CH(CH_3)-$ |
| $Br_3CCH_2OCO-$ | $3\text{-}Cl\text{-}4\text{-}C_6H_5CH_2OC_6H_3CH_2-$ |
| $Br_3CCH_2OCO-$ | $2\text{-}F\text{-}4HOC_6H_3CH_2-$ |
| $Br_3CCH_2OCO-$ | $3,4\text{-}(C_2H_5CO_2)_2C_6H_3CH_2-$ |
| $Br_3CCH_2OCO-$ | $4\text{-}(n\text{-}C_3H_7CO_2)C_6H_4CH_2-$ |
| $Br_3CCH_2OCO-$ | 2-furylmethyl- |
| $Br_3CCH_2OCO-$ | 5-methyl-2-furylmethyl- |
| $Br_3CCH_2OCO-$ | 2-thienylmethyl- |
| $Br_3CCH_2OCO-$ | 1-(2-furyl)ethyl- |
| $Br_3CCH_2OCO-$ | 1-(5-methyl-2-furyl)ethyl- |

EXAMPLE 44

In a manner similar to the procedure of Example 41, and starting with the intermediates of Example 40, the following congeners are synthesized:

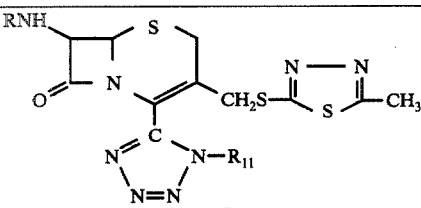

| R | $R_{11}$ |
|---|---|
| $Cl_3CCH_2OCO-$ | $4\text{-}C_6H_5CH_2OC_6H_4CH_2-$ |
| $Cl_3CCH_2OCO-$ | $4\text{-}C_6H_5CH_2O\text{-}3\text{-}FC_6H_3CH_2-$ |
| $Cl_3CCH_2OCO-$ | $2\text{-}Cl\text{-}4\text{-}CH_3OC_6H_3CH_2-$ |
| $Cl_3CCH_2OCO-$ | $3\text{-}Cl\text{-}4\text{-}HOC_6H_3CH_2-$ |
| $Cl_3CCH_2OCO-$ | $3,4\text{-}(CH_3O)_2C_6H_3CH_2-$ |
| $Cl_3CCH_2OCO-$ | $4\text{-}HOC_6H_4CH(CH_3)-$ |
| $Cl_3CCH_2OCO-$ | $2\text{-}Br\text{-}4\text{-}CH_3OC_6H_3CH_2-$ |
| $Cl_3CCH_2OCO-$ | $4\text{-}CH_3OC_6H_4CH(\phi)-$ |
| $Cl_3CCH_2OCO-$ | $2,4\text{-}(CH_3O)_2C_6H_3CH(CH_3)-$ |
| $Cl_3CCH_2OCO-$ | $4\text{-}CH_3OC_6H_4CH(n\text{-}C_3H_7)-$ |
| $Cl_3CCH_2OCO-$ | $3\text{-}CH_3\text{-}4\text{-}CH_3OC_6H_3CH_2-$ |
| $Cl_3CCH_2OCO-$ | $4\text{-}C_2H_6CO_2C_6H_4CH_2-$ |
| $Cl_3CCH_2OCO-$ | $3\text{-}F\text{-}4\text{-}CH_3CO_2C_6H_3CH_2-$ |
| $Cl_3CCH_2OCO-$ | $4\text{-}HOC_6H_4CH(\phi)-$ |
| $Cl_3CCH_2OCO-$ | $3\text{-}I\text{-}4\text{-}CH_3OC_6H_3CH_2-$ |
| $Cl_3CCH_2OCO-$ | $4\text{-}(i\text{-}C_3H_7CO_2)C_6H_4CH_2-$ |
| $Cl_3CCH_2OCO-$ | $3,4\text{-}(C_6H_5CH_2O)_2C_6H_3CH_2-$ |
| $Cl_3CCH_2OCO-$ | $4\text{-}CH_3OC_6H_4CH(CH_3)-$ |
| $Cl_3CCH_2OCO-$ | $4\text{-}CH_3OC_6H_4CH(C_2H_5)-$ |
| $Cl_3CCH_2OCO-$ | $3\text{-}F\text{-}4\text{-}CH_3CC_6H_3CH_2-$ |
| $Cl_3CCH_2OCO-$ | $3\text{-}Cl\text{-}4\text{-}CH_3OC_6H_3CH(CH_3)-$ |
| $Cl_3CCH_2OCO-$ | $4\text{-}HOC_6H_4CH_2-$ |
| $Cl_3CCH_2OCO-$ | $4\text{-}CH_3CO_2C_6H_4CH_2-$ |
| $Cl_3CCH_2OCO-$ | $3\text{-}F\text{-}4\text{-}HOC_6H_3CH_2-$ |
| $Cl_3CCH_2OCO-$ | $3\text{-}CH_3O\text{-}4\text{-}CH_3CO_2C_6H_4CH_2-$ |
| $Cl_3CCH_2OCO-$ | $4\text{-}C_6H_5CH_2OC_6H_3CH(CH_3)-$ |
| $Cl_3CCH_2OCO-$ | $3\text{-}Cl\text{-}4\text{-}C_6H_5CH_2OC_6H_3CH_2-$ |
| $Cl_3CCH_2OCO-$ | $3,4\text{-}(C_2H_5CO_2)_2C_6H_3CH_2-$ |
| $Cl_3CCH_2OCO-$ | $4\text{-}(n\text{-}C_3H_7CO_2)C_6H_4CH_2-$ |
| $Cl_3CCH_2OCO-$ | $4\text{-}(i\text{-}C_3H_7CO_2)C_6H_4CH(C_2H_5)-$ |
| $Cl_3CCH_2OCO-$ | 2-furylmethyl- |
| $Cl_3CCH_2OCO-$ | 5-methyl-2-furylmethyl- |
| $Cl_3CCH_2OCO-$ | 2-thienylmethyl- |

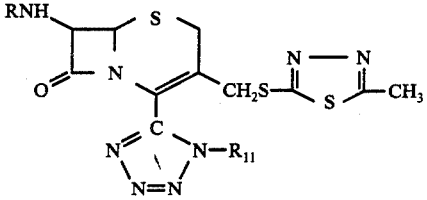

| R | $R_{11}$ |
|---|---|
| $Cl_3CCH_2OCO-$ | 5-methyl-2-thienylmethyl- |
| $Cl_3CCH_2OCO-$ | 1-(2-furyl)ethyl- |
| $Cl_3CCH_2OCO-$ | 1-(5-methyl-2-furyl)ethyl- |
| $Br_3CCH_2OCO-$ | $4\text{-}C_6H_5CH_2OC_6H_4CH_2-$ |
| $Br_3CCH_2OCO-$ | $4\text{-}C_6H_5CH_2O\text{-}3\text{-}FC_6H_3CH_2-$ |
| $Br_3CCH_2OCO-$ | $2\text{-}Cl\text{-}4\text{-}CH_3OC_6H_3CH_2-$ |
| $Br_3CCH_2OCO-$ | $4\text{-}Cl\text{-}4\text{-}HOC_6H_3CH_2-$ |
| $Br_3CCH_2OCO-$ | $2\text{-}Br\text{-}4\text{-}CH_3OC_6H_3CH_2-$ |
| $Br_3CCH_2OCO-$ | $2,4\text{-}(CH_3O)_2C_6H_3CH(CH_3)-$ |
| $Br_3CCH_2OCO-$ | $4\text{-}C_2H_5CO_2C_6H_4CH_2-$ |
| $Br_3CCH_2OCO-$ | $3\text{-}CH_3\text{-}4\text{-}CH_3OC_6H_3CH_2-$ |
| $Br_3CCH_2OCO-$ | $3\text{-}F\text{-}4\text{-}CH_3CO_2C_6H_3CH_2-$ |
| $Br_3CCH_2OCO-$ | $3\text{-}I\text{-}4\text{-}CH_3OC_6H_3CH_2-$ |
| $Br_3CCH_2OCO-$ | $4\text{-}(i\text{-}C_3H_7CO_2)C_6H_4CH_2-$ |
| $Br_3CCH_2OCO-$ | $3,4\text{-}(C_6H_5CH_2O)_2C_6H_3CH_2-$ |
| $Br_3CCH_2OCO-$ | $4\text{-}CH_3OC_6H_4CH(CH_3)-$ |
| $Br_3CCH_2OCO-$ | $4\text{-}CH_3OC_6H_4CH(C_2H_5)-$ |
| $Br_3CCH_2OCO-$ | $3,4\text{-}(CH_3O)_2C_6H_3CH_2-$ |
| $Br_3CCH_2OCO-$ | $3\text{-}F\text{-}4\text{-}CH_3OC_6H_3CH_2-$ |
| $Br_3CCH_2OCO-$ | $3\text{-}Cl\text{-}4\text{-}CH_3OC_6H_3CH(CH_3)-$ |
| $Br_3CCH_2OCO-$ | $4\text{-}HOC_6H_4CH_2-$ |
| $Br_3CCH_2OCO-$ | $4\text{-}HOC_6H_4CH(CH_3)-$ |
| $Br_3CCH_2OCO-$ | $4\text{-}CH_3CO_2C_6H_4CH_2-$ |
| $Br_3CCH_2OCO-$ | $3\text{-}Cl\text{-}4\text{-}HOC_6H_3CH_2-$ |
| $Br_3CCH_2OCO-$ | $3\text{-}Cl\text{-}4\text{-}CH_3CO_2C_6H_3CH_2-$ |
| $Br_3CCH_2OCO-$ | $4\text{-}C_6H_5CH_2OC_6H_3CH(CH_3)-$ |
| $Br_3CCH_2OCO-$ | $3\text{-}Cl\text{-}4\text{-}C_6H_5CH_2OC_6H_3CH_2-$ |
| $Br_3CCH_2OCO-$ | $2\text{-}F\text{-}4\text{-}HOC_6H_3CH_2-$ |
| $Br_3CCH_2OCO-$ | $3,4\text{-}(C_2H_5CO_2)_2C_6H_3CH_2-$ |
| $Br_3CCH_2OCO-$ | $4\text{-}(n\text{-}C_3H_7CO_2)C_6H_4CH_2-$ |
| $Br_3CCH_2OCO-$ | 2-furylmethyl- |
| $Br_3CCH_2OCO-$ | 5-methyl-2-furylmethyl- |
| $Br_3CCH_2OCO-$ | 2-thienylmethyl- |
| $Br_3CCH_2OCO-$ | 1-(2-furyl)ethyl- |
| $Br_3CCH_2OCO-$ | 1-(5-methyl-2-furyl)ethyl- |

EXAMPLE 45

7-Amino-3-acetoxymethyl-4-[1-(p-methoxybenzyl)tetrazol-5-yl)-$\Delta^3$-cephem

Activated zinc dust (300 mg.) is added to a stirred solution of 7-(2',2',2'-trichloroethoxycarboxamido-3-acetoxymethyl-4-[1-(p-methoxybenzyl)-tetrazol-5-yl]-$\Delta^3$-cephem (300 mg. 0.5 mmole) in 90% acetic acid (3 ml.) and the suspension is stirred at ambient temperature for 30 min. The reaction mixture is filtered, and evaporated to dryness. The resultant yellow foam is dissolved in chloroform, and the solution extracted twice with dilute hydrochloric acid. The aqueous extracts are mixed with chloroform, and dilute sodium hydroxide is added to the stirred mixture to pH 7.0. The mixture is filtered to remove precipitated inorganic salts, the layers separated, and the aqueous solution extracted twice with chloroform. The combined organic extracts are washed with water and dried over magnesium sulphate. Evaporation of the solvent affords the product as a pale yellow solid (110 mg.), pure by t.l.c.

NMR (CDCl$_3$): $\delta$ = 1.9(s) 1H; 2.0(s) 3H; 3.45(q) 2H; 3.8(s) 3H; 4.3(q) 2H; 3.8(s) 3H; 4.3(q) 2H; 4.65(d) 1H; 4.95(d) 1H; 5.5;1 (s) 2H and 7.1(q) 4H.

Similarly, starting with 7-(2',2',2'-trichloroethoxycarboxamido)-3-(2-methyl-1,3,4-thiadiazol-5-ylthiomethyl)-4-[1-(p-methoxybenzyl)tetrazol-5-yl]-$\Delta^3$-cephem and following the procedure of Example 45, 7-amino-3-(2-methyl-1,3,4-thiadiazol-5-ylthiomethyl)-4-[1-(p-methoxybenzyl)tetrazol-5-yl]-$\Delta^3$-cephem is prepared.

NMR (CDCl$_3$): δ = 7.0(q) 4H; 5.55(s) 2H; 4.9(d) 1H; 4.6(m) 1H; 3.8 (s) 3H; 3.65(m) and 2H and 2.7(s) 3H.

EXAMPLE 46

The procedure of Example 45 is repeated, starting with the intermediate Δ$^3$-cephems of Examples 43 and 44, to give the following analogs:

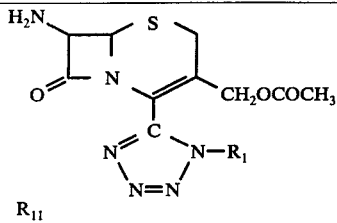

4-C$_6$H$_5$CH$_2$OC$_6$H$_4$CH$_2$—
4-C$_6$H$_5$CH$_2$O-3-FC$_6$H$_3$CH$_2$—
2-Cl-4-CH$_3$OC$_6$H$_3$CH$_2$—
3-Cl-4-HOC$_6$H$_3$CH$_2$—
3,4-(CH$_3$O)$_2$C$_6$H$_3$CH$_2$—
4-HOC$_6$H$_4$CH(CH$_3$)—
2-Br-4-CH$_3$OC$_6$H$_3$CH$_2$—
4-CH$_3$OC$_6$H$_4$CH(φ)—
2,4-(CH$_3$O)$_2$C$_6$H$_3$CH(CH$_3$)—
4-CH$_3$OC$_6$H$_4$CH(n-C$_3$H$_7$)—
3-CH$_3$-4-CH$_3$OC$_6$H$_3$CH$_2$—
4-C$_2$H$_5$CO$_2$C$_6$H$_4$CH$_2$—
3-F-4-CH$_3$CO$_2$C$_6$H$_3$CH$_2$—
4-HOC$_6$H$_4$CH(φ)—
3-I-4-CH$_3$OC$_6$H$_3$CH$_2$—
4-(i-C$_3$H$_7$CO$_2$)C$_6$H$_4$CH$_2$—
3,4-(C$_6$H$_5$CH$_2$O)$_2$C$_6$H$_3$CH$_2$—
4-CH$_3$OC$_6$H$_4$CH(CH$_3$)—
4-CH$_3$OC$_6$H$_4$CH(C$_2$H$_5$)—
3-F-4-CH$_3$OC$_6$H$_3$CH$_2$—
3-Cl-4-CH$_3$OC$_6$H$_3$CH(CH$_3$)—
4-HOC$_6$H$_4$CH$_2$—
4-CH$_3$CO$_2$C$_6$H$_4$CH$_2$—
3-F-4-HOC$_6$H$_3$CH$_2$—
3-CH$_3$O-4-CH$_3$CO$_2$C$_6$H$_4$CH$_2$—
4-C$_6$H$_5$CH$_2$OC$_6$H$_3$CH(CH$_3$)—
3-Cl-4-C$_6$H$_4$CH$_2$OC$_6$H$_3$CH$_2$—
3,4-(C$_2$H$_5$CO$_2$)$_2$C$_6$H$_3$CH$_2$—
4-(n-C$_3$H$_7$CO$_2$)C$_6$H$_4$CH$_2$—
4-(i-C$_3$H$_7$CO$_2$)C$_6$H$_4$CH(C$_2$H$_5$)—
2-furylmethyl-
5-methyl-2-furylmethyl-
2-thienylmethyl-
5-methyl-2-thienylmethyl-
1-(2-furyl)ethyl-
1-(5-methyl-2-furyl)ethyland

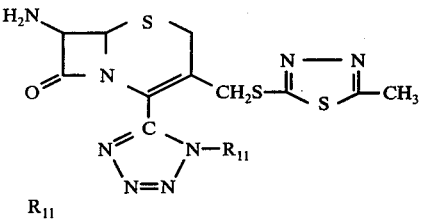

4-C$_6$H$_5$CH$_2$OC$_6$H$_4$CH$_2$—
4-C$_6$H$_5$CH$_2$O-3-FC$_6$H$_3$CH$_2$—
2-Cl-4-CH$_3$OC$_6$H$_3$CH$_2$—
3-Cl-4-HOC$_6$H$_3$CH$_2$—
3,4-(CH$_3$O)$_2$C$_6$H$_3$CH$_2$—
4-HOC$_6$H$_4$CH(CH$_3$)—
2-Br-4-CH$_3$OC$_6$H$_3$CH$_2$—
4-CH$_3$OC$_6$H$_4$CH(φ)-
2,4-(CH$_3$O)$_2$C$_6$H$_3$CH(CH$_3$)—
4-CH$_3$OC$_6$H$_4$CH(n-C$_3$H$_7$)—
3-CH$_3$-4-CH$_3$OC$_6$H$_3$CH$_2$—
4-C$_2$H$_5$CO$_2$C$_6$H$_4$CH$_2$—
3-F-4-CH$_3$CO$_2$C$_6$H$_3$CH$_2$—
4-HOC$_6$H$_4$CH(φ)—
3-I-4-CH$_3$OC$_6$H$_3$CH$_2$—
4-(i-C$_3$H$_7$CO$_2$)C$_6$H$_4$CH$_2$—
3,4-(C$_6$H$_5$CH$_2$O)$_2$C$_6$H$_3$CH$_2$—
4-CH$_3$OC$_6$H$_4$CH(CH$_3$)—
4-CH$_3$OC$_6$H$_4$CH(C$_2$H$_5$)—
3-F-4-CH$_3$OC$_6$H$_3$CH$_2$—
3-Cl-4-CH$_3$OC$_6$H$_3$CH(CH$_3$)—
4-HOC$_6$H$_4$CH$_2$—

-continued

4-CH$_3$CO$_2$C$_6$H$_4$CH$_2$—
3-F-4-HOC$_6$H$_3$CH$_2$—
3-CH$_3$O-4-CH$_3$CO$_2$C$_6$H$_4$CH$_2$—
4-C$_6$H$_5$CH$_2$OC$_6$H$_3$CH(CH$_3$)—
3-Cl-4-C$_6$H$_4$CH$_2$OC$_6$H$_3$CH$_2$—
3,4-(C$_2$H$_5$CO$_2$)$_2$C$_6$H$_3$CH$_2$—
4-(n-C$_3$H$_7$CO$_2$)C$_6$H$_4$CH$_2$—
4-(i-C$_3$H$_7$CO$_2$)C$_6$H$_4$CH(C$_2$H$_5$)—
2-furylmethyl-
5-methyl-2-furylmethyl-
2-thienylmethyl-
5-methyl-2-thienylmethyl-
1-(2-furyl)ethyl-
1-(5-methyl-2-furyl)ethyl-

EXAMPLE 47

7-Amino-3-(2-methyl-1,3,4-thiadiazol-5-ylthiomethyl)-4-(tetrazol-5-yl)-Δ$^3$-cephem 7-Amino-3-(2-methyl-1,3,4-thiadiazol-5-ylthiomethyl)-4-[1-(p-methoxybenzyl)tetrazol-5-yl]-Δ$^3$-cephem (125 mg.) is dissolved in acetone (2 ml.) and p-toluenesulphonic acid (60 mg.) in acetone (1 ml.) added. The salt precipitates out as a brown oil after addition of ether to this mixture. The solvent is decanted and the residue washed (3 x) with ether (30 ml.). The residual oil is dissolved in trifluoroacetic acid/Anisole (4:1 v/v; 2 ml.) and heated on a water bath, in a stoppered flask (25 ml.) for 3 hrs. at 38° C.

At the end of this time the reaction mixture is poured into dry ether, the organic solvents decanted from the instantly formed precipitate, and the residual solids washed with further portions of ether (3 × 30 ml.). The crude deprotected material was taken up in acetone/water (ph 2.5), extracted with ethyl acetate, the pH of the aqueous phase adjusted to 7.6 with aqueous sodium hydroxide (2N) and re-extracted with ethyl acetate. Concentration of the aqueous phase in vacuo, to dryness, affords a solid. This compound is characterized by acylation of the above sodium salt with 2',2',2'-trichloroethoxycarbonyl chloride using the procedure of Example 1A to give 7-(2',2',2'-trichloroethoxycarboxamido)-3-(2-methyl-1,3,4-thiadiazol-5-ylthiomethyl)-4-(tetrazol-5-yl)-Δ$^3$-cephem.

NMR (CDCl$_3$): δ = 4.7(d) 1H; 4.2(m) 1H; 5.1(s) 2H; 5.35(s) 2H; 6.0(m) 2H and 7.2(s) 3H.

EXAMPLE 48

Similar to the procedure of Example 47, and starting with the compounds of Example 46, 7-amino-3-acetoxymethyl-4-(tetrazol-5-yl)-Δ$^3$-cephem and 7-amino-3-(2-methyl-1,3,4-thiadiazol-5-ylthiomethyl)-4-(tetrazol-5-yl)-Δ$^3$-cephem are prepared.

EXAMPLE 49

Sodium bicarbonate (42 g., 0.5 mole) is added gradually to a vigorously stirred suspension of 7-amino-3-acetoxymethyl-Δ$^3$-cephem-4-carboxylic acid (50 g., 0.18 mole) in acetone/water (250/500 ml.). A solution of benzyl chloroformate (36 g., 0.21 mole) in acetone (70 ml.) is added dropwise to the stirred solution over a period of 45 min. After stirring for six hrs. the acetone is removed on the rotary evaporator and the aqueous residue washed with ethyl acetate to remove impurities. The aqueous solution is overlaid with ethyl acetate and acidified to pH 4.0. The combined ethyl acetate solutions from the extractions of the aqueous solution are washed with water and dried over magnesium sulphate. Evaporation of the ethyl acetate affords the product, 7-benzyloxycarboxamido-3-acetoxymethyl-Δ³-cephem-4-carboxylic acid, as an off-white solid (56 g.), pure by t.l.c.

NMR (DMSOd₆): δ = 2.0(s) 3H; 3.5(s) 2H; 4.8–5.2(m) 5H and 7.3(s) 5H.

Similarly are prepared 7-benzyloxycarboxamido-3-(1-methyltetrazol-5-ylthiomethyl)-Δ³-cephem-4-carboxylic acid, NMR (DMSOd₆) δ = 7.5(s) 5H; 6.6(d) 1H; 6.2(s) 3H; 4.4(b) 2H; 4.04 (s) 3H and 3.8(s) 2H;

7-benzyloxycarboxamido-3-methly-Δ³-cephem-4-carboxylic acid; and 7-benzyloxycarboxamido-3-(2-methyl-1,3,4-thiadiazol-5-ylthiomethyl)-Δ³-cephem-4-carboxylic acid.

EXAMPLE 50

7-Benzyloxycarboxamido-3-acetoxymethyl-4-[N-(p-methoxybenzyl)carbamoyl)-Δ³-cephem A solution of 2,4-dinitrophenol (22 g., 0.1 mole) in methylene chloride (100 ml.) is added to a solution of 7-benzyloxycarboxamido-3-acetoxymethyl-Δ³-cephem-4-carboxylic acid (41 g., 0.1 mole) in dry dioxane (400 ml.). To this stirred solution of dicyclohexylcarbodiimide (21 g., 0.1 mole) in dioxane (100 ml.). After 1.5 hr. the precipitate of dicyclohexylurea is removed by filtration. To the filtrate is added a solution of p-methoxybenzylamine (13.7 g., 0.1 mole) in dioxane (100 ml.). After stirring for 6 hrs. the precipitated solid is filtered, washed with ether and ethyl acetate and dried, affording the product as a white solid (30 g.) pure by t.l.c.

NMR (DMSOd₆): δ = 2.0(s) 3H; 3.4(s) 2H; 3.7(s) 3H; 4.3(d) 2H; 4.9 (d) 2H; 5.0(m) 4H; 5.4(q) 1H amd 7.0(m) 9H.

In a similar manner is prepared 7-benzyloxycarboxamido-3-(1-methyltetrazol-5-ylthiomethyl)-4-[N-(p-methoxybenzyl)carbamoyl[-Δ³-cephem.

NMR (CDCl₃): δ = 7.4(s) 5H; 7.1(q) 4H; 7.7(m) 2H; 5.25(s) 2H; 5.45 (d) 1H; 4.5(m) 4H; 4.0(s) 3H; 5.9(s) 3H and 5.79(s) 2H; and 7-benzyloxycarboxamido-3-(2-methyl-1,3,4-thiadiazol-5-ylthiomethyl)-4-[N-(p-methoxybenzyl)carbamoyl]-Δ³-cephem.

EXAMPLE 51

Starting with the appropriate 3-substituted-7-benzyloxycarboxamido-Δ³-cephem-4-carboxylic acid from Example 49, and employing the procedures of Example 50, the following amide intermediates are prepared:

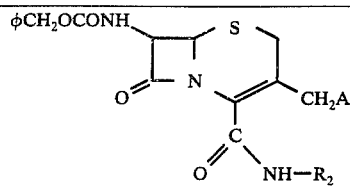

| R₂ | A |
|---|---|
| 4-C₆H₅CH₂OC₆H₄CH₂— | CH₃CO₂— |
| 3-Cl-4-HOC₆H₃CH₂— | CH₃CO₂— |
| 3,4-(CH₃O)₂C₆H₃CH₂— | CH₃CO₂— |
| 4-CH₃OC₆H₄CH(φ)— | CH₃CO₂— |
| 3-CH₃-4-CH₃OC₆H₃CH₂— | CH₃CO₂— |
| 4-(i-C₃H₇CO₂)C₆H₄CH₂— | CH₃CO₂— |
| 4-CH₃OC₆H₄CH(CH₃)— | CH₃CO₂— |
| 4-HOC₆H₄CH₂— | CH₃CO₂— |
| 3-CH₃O-4-CH₃CO₂C₆H₃CH₂— | CH₃CO₂— |
| 2-furylmethyl- | CH₃CO₂— |
| 1-(2-furyl)ethyl- | CH₃CO₂— |
| 3-F-4-CH₃CO₂C₆H₃CH₂— | C₃H₃N₂S₂* |
| 4-CH₃OC₆H₄CH(φ)— | C₃H₃N₂S₂* |

-continued

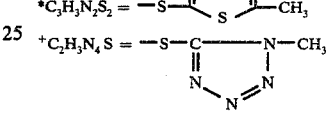

| R₂ | A |
|---|---|
| 4-C₂H₅CO₂C₆H₄CH₂— | C₃H₃N₂S₂* |
| 4-(i-C₃H₇CO₂)C₆H₄CH₂— | C₃H₃N₂S₂* |
| 3-F-4-HOC₆H₃CH₂— | C₃H₃N₂S₂* |
| 4-HOC₆H₄CH(CH₃)— | C₃H₃N₂S₂* |
| 4-CH₃OC₆H₄CH(C₂H₅)— | C₃H₃N₂S₂* |
| 4-CH₃OC₆H₄CH(n-C₃H₇)— | C₃H₃N₂S₂* |
| 4-CH₃OC₆H₄CH(n-C₃H₇)— | C₂H₃N₄S+ |
| 2-Br-4-CH₃OC₆H₃CH₂— | C₂H₃N₄S+ |
| 4-HOC₆H₄CH(φ)— | C₂H₃N₄S+ |
| 5-methyl-2-furylmethyl- | C₂H₃N₄S+ |
| 4-C₆H₅CH₂OC₆H₄CH₂— | C₂H₃N₄S+ |
| 3,4-(CH₃CO₂)₂C₆H₃CH₂— | C₂H₃N₄S+ |
| 4-(i-C₃H₇CO₂)C₆H₄CH₂— | C₂H₃N₄S+ |
| 2-furylmethyl- | C₂H₃N₄S+ |
| 5-methyl-2-thienylmethyl- | 2-thienylmethyl—C₂H₃N₄S+ |

$$*C_3H_3N_2S_2 = -S-\underset{S}{\overset{N-N}{\parallel\parallel}}-CH_3$$

$$+C_2H_3N_4S = -S-\underset{N\diagdown_N\diagup^N}{\overset{C}{\parallel}}-N-CH_3$$

EXAMPLE 52

Phosphorous pentachloride (4.2 g., 20 mmole) is added to a suspension of 7-benzyloxycarboxamido-3-acetoxymethyl-4-[N-(p-methoxybenzyl)carbamoyl]-Δ³-cephem (5.3 g., 10 mmole) in dry, ethanol-free chloroform (100 ml.) containing pyridine (1.7 g., 20 mmole). After 30 min., NMR indicates the reaction is complete.

The solution is cooled in an ice-bath and a solution of tetramethyl-guanidinium azide (16.0 g., 100 mmole) in dry, ethanol free chloroform is added dropwise over a period of 20 min. After a further 10 min. the ice-bath is removed and stirring is continued for 30 min. at ambient temperatures. The solution is washed with water, sodium bicarbonate solution (3 x), 6N hydrochloric acid (3 x), water, and dried over magnesium sulphate. Evaporation of the solvent affords the crude product as a brown solid (3.7 g.), which is purified by column chromatography on silica. Elution with dichloromethane: hexane (1:1) and then with ether:dichloromethane:hexane (2:1:1) removes impurities. Elution with ether affords the product, 7-benzyloxycarboxamido-3-acetoxymethyl-4-[1-(p-methoxybenzyl)tetrazol-5-yl]-Δ³-cephem, as a white solid, pure by t.l.c.

NMR (DMSOd₆): δ = 1.9(s) 3H; 3.65(s) 2H; 3.8(s) 3H; 4.3(s) 2H; 5.15(s) 2H; 5.35(d) 1H; 5.6(m) 3H; 7.2(m) 9H and 8.6(d) 1H.

Similarly is prepared 7-benzyloxycarboxamido-3-(1-methyltetrazol-5-ylthiomethyl)-4-[1-(p-methoxybenzyl)tetrazol-5-yl]-Δ³-cephem.

NMR (DMSOd₆₁): δ = 7.3(s) 5H; 7.05(q) 4H; 6.5(s) 3H; 6.2(d) 1H; 5.05 (s) 2H; 3.85(s) 3H; 3.7(s) 3H; 3.5-4(m) 2H and 3.3(s) 2H.

EXAMPLE 53

Employing the procedure of Example 52, and starting with the amides of Example 51, the following tetrazole intermediates are synthesized:

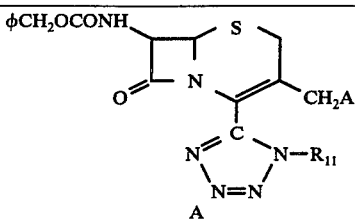

| $R_{11}$ | A |
|---|---|
| 4-C6H5CH2OC6H4CH2— | CH3CO2— |
| 3-Cl-4-HOC6H3CH2— | CH3CO2— |
| 3,4-(CH3O)2C6H3CH2— | CH3CO2— |
| 4-CH3OC6H4CH(φ)— | CH3CO2— |
| 3-CH3-4-CH3OC6H3CH2— | CH3CO2— |
| 4-(i-C3H7CO2)C6H4CH2— | CH3CO2— |
| 4-CH3OC6H4CH(CH3)— | CH3CO2— |
| 4-HOC6H4CH2— | CH3CO2— |
| 3-CH3O-4-CH3CO2C6H3CH2— | CH3CO2— |
| 2-furylmethyl- | CH3CO2— |
| 1-(2-furyl)ethyl- | CH3CO2— |
| 3-F-4-CH3CO2C6H3CH2— | C3H3N2S2* |
| 4-CH3OC6H4CH(φ)— | C3H3N2S2* |
| 4-C2H5CO2C6H4CH2— | C3H3N2S2* |
| 4-(i-C3H7CO2)C6H4CH2— | C3H3N2S2* |
| 3-F-4-HOC6H3CH2— | C3H3N2S2* |
| 4-HOC6H4CH(CH3)— | C3H3N2S2* |
| 4-CH3OC6H4CH(C2H5)— | C3H3N2S2* |
| 4-CH3OC6H4CH(n-C3H7)— | C3H3N2S2* |
| 4-CH3OC6H4CH(n-C3H7)— | C2H3N4S+ |
| 2-Br-4-CH3OC6H3CH2— | C2H3N4S+ |
| 4-HOC6H4CH(φ)— | C2H3N4S+ |
| 5-methyl-2-furylmethyl- | C2H3N4S+ |
| 4-C6H5CH2OC6H4CH2— | C2H3N4S+ |
| 3,4-(CH3CO2)2C6H3CH2— | C2H3N4S+ |
| 4-(i-C3H7CO2)C6H4CH2— | C2H3N4S+ |
| 2-furylmethyl- | C2H3N4S+ |
| 5-methyl-2-thienylmethyl- | C2H3N4S+ |

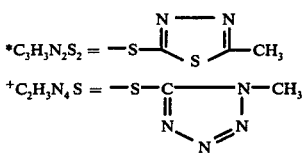

EXAMPLE 54

7-Amino-3-acetoxymethyl-4-(tetrazol-5-yl)-$\Delta^3$-cephem

7-Benzyloxycarboxamido-3-acetoxymethyl-4-[1-(p-methoxybenzyl)tetrazol-5-yl]-$\Delta^3$-cephem (100 mg.) is dissolved in trifluoroacetic acid/anisole (4:1, v/v), (0.5 cc) and to this reddish-brown solution trifluoromethanesulphonic acid is added from a Pasteur pipette (25 drops). Immediate effervescence is observed and the solution turns cherry-red.

After 3 min. at room temperature the reaction mixture is quenched by addition of ether (sodium dried). A brown gum is deposited, the supernatent liquids are decanted, and the residue washed again with ether.

The viscous gum is redissolved in the minimum volume of methylene chloride containing 1% triethylamine and the solution chromatographed on silica (2 mm, 20 × 20, Kieselgel G F254) using acetonitrile/water (6:1 v/v) as the eluting solvent.

The band at r.f. 0.4 was removed and extracted with 1% triethylamine/methylene chloride (3 × 150 ml.). The organic extracts are evaporated to dryness in vacuo to afford a white solid, a mixture of 7-amino-3-acetoxymethyl-4-(tetrazol-5-yl)-$\Delta^3$-cephem and triethylamine hydrochloride.

NMR (CDCl3): $\delta$ = 5.25(d) 1H; 4.9(m) 2H and 2.05(s) 3H.

EXAMPLE 55

7-Amino-3-(1-methyltetrazol-5-ylthiomethyl)-4-(tetrazol-5-yl)-$\Delta^3$-cephem

In a manner similar to Example 54, starting with 7-benzyloxycarboxamido-3-(1-methyltetrazol-5-ylthiomethyl)-4-[1-(p-methoxybenzyl)tetrazol-5-yl]-$\Delta^3$-cephem, the crude product is obtained.

The Zwitterion is isolated by crystallization of the crude reaction mixture, after precipitation with dry ether, from a minimum volume of potassium hydrogen phosphate pH 7 buffer. After initial dissolution of the crude reaction mixture the Zwitterion precipitates as a cream-yellow solid and is pure by thin layer chromatography.

NMR (DMSOd6): $\delta$ = 5.1(d) 1H; 4.8(d) 1H; 4.3(q) 2H; 3.9(s) 3H and 3.7(s) 2H.

EXAMPLE 56

Employing the experimental conditions of Example 54, and starting with the requisite products of Example 53, the intermediates 7-amino-3-acetoxy-4-(tetrazol-5-yl)-$\Delta^3$-cephem, 7-amino-3-(1-methyltetrazol-5-ylthiomethyl)-4-(tetrazol-5-yl)-$\Delta^3$-cephem and 7-amino-3-(2-methyl-1,3,4-thiadiazol-5-ylthiomethyl)-4-(tetrazol-5-yl)-$\Delta^3$-cephem are produced.

EXAMPLE 57

7-(2',2',2'-Trichloroethoxycarboxamido)-3-methyl-$\Delta^2$-cephem 4-carboxylic acid 7-(2',2',2'-Trichloroethoxycarboxamido)-3-methyl-$\Delta^3$-cephem-4-carboxylic acid (66.6 g.) and N-hydroxysuccinimide (21.6 g.) in dioxane (200 ml.) at room temperature is treated with dicyclohexylcarbodiimide (35.6 g.) and the mixture allowed to stir for one hour at room temperature. The mixture is filtered and the filtrate evaporated under reduced pressure to leave an oil which is dissolved in pyridine (400 ml.) at 7° C. and is then treated with aqueous sodium hydroxide (7.5 g. in 100 ml.) with vigorous stirring. The mixture is allowed to warm to 25° C. and stirring continued for a further 1.75 hrs. The pyridine is evaporated under reduced pressure and the residue poured onto ice. The pH is adjusted to 2 with 6N HCl acid and the precipitate extracted into ethyl acetate. The organic solution is washed with 1N HCl acid, water, and then evaporated under reduced pressure. The residue is dissolved in aqueous sodium carbonate solution and the resultant solution is washed with ethyl acetate. The aqueous solution is treated with charcoal, filtered and the pH of the filtrate adjusted to 2 with 6N HCl acid. The precipitate is extracted into ethyl acetate and the organic solution is treated with charcoal, filtered, and dried (MgSO4). The solution is then evaporated under reduced pressure to leave the required product as a foam, which solidifies on trituration with petroleum ether (48.0 g.) and is essentially pure by chromatography.

NMR (CDCl3): $\delta$ = 7.5(d) 1H; 6.0(q) 1H; 5.2(m) 2H; 4.7(s) 2H; 4.6(s) 1H and 1.9(s) 3H.

EXAMPLE 58

In a similar manner to Example 57, starting with 7-(2',2',2'-tribromoethoxycarboxamido)-3-methyl-$\Delta^3$-cephem-4-carboxylic acid prepared by the general procedure of Example 1A, in place of the corresponding chloro compound, 7-(2',2',2'-tribromoethoxycarboxamido)-3-methyl-Δ²-cephem-4-carboxylic acid is produced.

EXAMPLE 59

7-(2',2',2'-Trichloroethoxycarboxamido)-3-methyl-4-[N-(p-methoxybenzyl)carbamoyl]-Δ²-cephem 7-(2',2',2'-Trichloroethoxycarboxamido)-3-methyl-Δ²-cephem-4-carboxylic acid (46.0 g.) and N-hydroxysuccinimide (14.3 g.) in dioxane (750 ml.) is treated after 1 hr. with dicyclohexylcarbodiimide (24.3 g.) at room temperature with stirring. To this stirred solution is added p-methoxybenzylamine (32.8 g.) in dioxane (200 ml.) and the mixture stirred for a further hour at room temperature. The mixture is filtered and the solution stirred for a further hour at room temperature. The mixture is filtered and the solution concentrated to 300 ml. under reduced pressure. The concentrate is poured into a saturated aqueous $Na_2CO_3$ solution (2 liters) and the precipitate collected. The precipitate is washed with water, 1N HCl, and finally water. The solid is dried under reduced pressure at 100° C. for 16 hrs. to furnish 7-(2',2',2'-trichloroethoxycarboxamido)-3-methyl-4-[N-(p-methoxybenzyl)-carbamoyl]-Δ²-cephem (58.6 g.). A sample is recrystallized from acetone (m.p. 219°–220° C.).

NMR (DMSOd₆): δ = 7.0(q) 4H; 6.0(q) 1H; 5.2(m) 2H; 4.7(s) 2H; 4.6(s) 1H; 4.2(d) 2H; 3.7(s) 3H and 1.7(s) 3H.

EXAMPLE 60

Starting with 7-(2',2',2'-trichloroethoxycarboxamido)-3-methyl-Δ²-cephem-4-carboxylic acid, prepared by the procedure of Example 57, and the appropriate amine, and repeating the procedure of Example 59, the following intermediate amides are prepared:

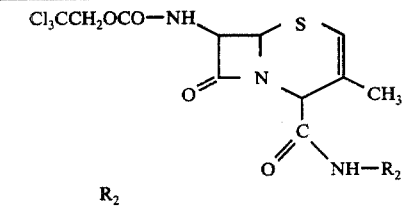

R₂
4-C₆H₅CH₂OC₆H₄CH₂—
4-C₆H₅CH₂O-3-FC₆H₃CH₂—
2-Cl-4-CH₃OC₆H₃CH₂—
3-Cl-4-HOC₆H₃CH₂—
3,4-(CH₃O)₂C₆H₃CH₂—
4-HOC₆H₄CH(CH₃)—
2-Br-4-CH₃OC₆H₃CH₂—
4-CH₃OC₆H₄CH(φ)—
2,4-(CH₃O)₂C₆H₃CH(CH₃)—
4-CH₃OC₆H₄CH(n-C₃H₇)—
3-CH₃-4-CH₃OC₆H₃CH₂—
4-C₂H₅CO₂C₆H₄CH₂—
3-F-4-CH₃CO₂C₆H₃CH₂—
4-HOC₆H₄CH(φ)—
3-I-4-CH₃OC₆H₃CH₂—
4-(i-C₃H₇CO₂)C₆H₄CH₂—
3,4-(C₆H₅CH₂O)₂C₆H₃CH₂—
4-CH₃OC₆H₄CH(CH₃)—
4-CH₃OC₆H₄CH(C₂H₅)—
3-F-4-CH₃OC₆H₃CH₂—
3-Cl-4-CH₃OC₆H₃CH(CH₃)—
4-HOC₆H₄CH₂—
4-CH₃CO₂C₆H₄CH₂—
3-F-4-HOC₆H₃CH₂—
3-CH₃O-4-CH₃CO₂C₆H₃CH₂—
4-C₂H₅CH₂OC₆H₃CH(CH₃)—
3-Cl-4-C₆H₄CH₂OC₆H₃CH₂—
3,4-(C₂H₅CO₂)₂C₆H₃CH₂—
4-(n-C₃H₇CO₂)C₆H₄CH₂—
4-(i-C₃H₇CO₂)C₆H₄CH(C₂H₅)—
2-furylmethyl-
5-methyl-2-furylmethyl-

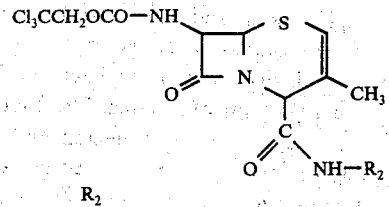

2-thienylmethyl-
5-methyl-2-thienylmethyl-
1-(2-furyl)ethyl-
1-(5-methyl-2-furyl)ethyl-

EXAMPLE 61

Similarly, when 7-(2',2',2'-tribromoethoxycarboxamido)-3-methyl-Δ²-cephem-4-carboxylic acid is employed as the reagent in place of 7-(2',2',2'-trichloroethoxycarboxamido)-3-methyl-Δ²-cephem-4-carboxylic acid in the procedure of Example 59 along with the appropriate amine, the following amides are synthesized:

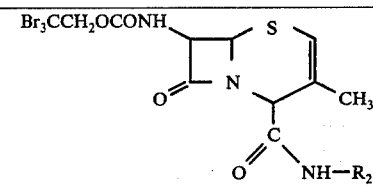

4-C₆H₅CH₂OC₆H₄CH₂—
4-C₆H₅CH₂O-3-FC₆H₃CH₂—
2-Cl-4-CH₃OC₆H₃CH₂—
4-Cl-4-HOC₆H₃CH₂—
2-Br-4-CH₃OC₆H₃CH₂—
2,4-(CH₃O)₂C₆H₃CH(CH₃)—
4-C₂H₅CO₂C₆H₄CH₂—
3-CH₃-4-CH₃OC₆H₃CH₂—
3-F-4-CH₃CO₂C₆H₃CH₂—
3-I-4-CH₃OC₆H₃CH₂—
4-(i-C₃H₇CO₂)C₆H₄CH₂—
3,4-(C₆H₅CH₂O)₂C₆H₃CH₂—
4-CH₃OC₆H₄CH(CH₃)—
4-CH₃OC₆H₄CH(C₂H₅)—
3,4-(CH₃O)₂C₆H₃CH₂—
3-F-4-CH₃OC₆H₃CH₂—
3-Cl-4-CH₃OC₆H₃CH(CH₃)—
4-HOC₆H₄CH₂—
4-HOC₆H₄CH₂—
4-CH₃CO₂C₆H₄CH₂—
3-Cl-4-HOC₆H₃CH₂—
3-Cl-4-CH₃CO₂C₆H₃CH₂—
4-C₆H₅CH₂OC₆H₃CH(CH₃)—
3-Cl-4-C₆H₅CH₂OC₆H₃CH₂—
2-F-4-HOC₆H₃CH₂—
3,4-(C₂H₅CO₂)₂C₆H₃CH₂—
4-(n-C₃H₇CO₂)C₆H₄CH₂—
2-furylmethyl-
5-methyl-2-furylmethyl-
2-thienylmethyl-
1-(2-furyl)ethyl-
1-(5-methyl-2-furyl)ethyl-

EXAMPLE 62

7-(2',2',2'-Trichloroethoxycarboxamido)-3-methyl-4-[1-(p-methoxybenzyl)-tetrazol-5-yl]-Δ²-cephem 7-(2',2',2'-Trichloroethoxycarboxamido)-3-methyl-4-[N-(p-methoxybenzyl)carbamoyl]-Δ²-cephem (44.2 g.) and pyridine (14.06 g.) in chloroform (300 ml., ethanol free) at 40° C. is treated with phosphorus pentachloride (27.5 g.) and the mixture stirred at 40° C. for 3 hrs. The solution is cooled to room temperature and tetramethylguanidinium azide (87.9 g.) added, and the solution allowed to stir at room temperature for 2 hrs. The solution is then washed with water, aqueous sodium bicarbonate, 1N HCl acid, water, and dried (MgSO$_4$). The organic solution is evaporated under reduced pressure to leave a gum which is dissolved in ethyl acetate (200 ml.) and passed down a column of alumina. The fraction containing the required product is collected and the solution evaporated to dryness under reduced pressure to yield the product as a pale orange solid (42.4 g.).

NMR (CDCl$_3$): δ = 7.0(q) 4H; 6.1(d) 1H; 6.0(s) 1H; 5.6(q) 2H; 5.4(s) 1H; 5.2(q) 1H; 4.8(d) 1H; 4.7(s) 2H; 3.7(s) 3H and 1.5(s) 3H.

EXAMPLE 63

In a manner similar to the procedure of Example 62, the amides of Example 60 are converted to the corresponding tetrazoles of the structure:

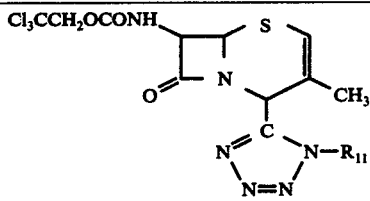

| R$_{11}$ |
|---|
| 4-C$_6$H$_5$CH$_2$OC$_6$H$_4$CH$_2$— |
| 4-C$_6$H$_5$CH$_2$O-3-FC$_6$H$_3$CH$_2$— |
| 2-Cl-4-CH$_3$OC$_6$H$_3$CH$_2$— |
| 3-Cl-4-HOC$_6$H$_3$CH$_2$— |
| 3,4-(CH$_3$O)$_2$C$_6$H$_3$CH$_2$— |
| 4-HOC$_6$H$_4$CH(CH$_3$)— |
| 2-Br-4-CH$_3$OC$_6$H$_3$CH$_2$— |
| 4-CH$_3$OC$_6$H$_4$CH(φ)— |
| 2,4-(CH$_3$O)$_2$C$_6$H$_3$CH(CH$_3$)— |
| 4-CH$_3$OC$_6$H$_4$CH(n-C$_3$H$_7$)— |
| 3-CH$_3$-4-CH$_3$OC$_6$H$_3$CH$_2$— |
| 4-C$_2$H$_5$CO$_2$C$_6$H$_4$CH$_2$— |
| 3-F-4-CH$_3$CO$_2$C$_6$H$_3$CH$_2$— |
| 4-HOC$_6$H$_4$CH(φ)— |
| 3-I-4-CH$_3$OC$_6$H$_3$CH$_2$— |
| 4-(i-C$_3$H$_7$CO$_2$)C$_6$H$_4$CH$_2$— |
| 3,4-(C$_6$H$_5$CH$_2$O)$_2$C$_6$H$_3$CH$_2$— |
| 4-CH$_3$OC$_6$H$_4$CH(CH$_3$)— |
| 4-CH$_3$OC$_6$H$_4$CH(C$_2$H$_5$)— |
| 3-F-4-CH$_3$OC$_6$H$_3$CH$_2$— |
| 3-Cl-4-CH$_3$OC$_6$H$_3$CH(CH$_3$)— |
| 4-HOC$_6$H$_4$CH$_2$— |
| 4-CH$_3$CO$_2$C$_6$H$_4$CH$_2$— |
| 3-F-4-HOC$_6$H$_3$CH$_2$— |
| 3-CH$_3$O-4-CH$_3$CO$_2$C$_6$H$_4$CH$_2$— |
| 4-C$_6$H$_5$CH$_2$OC$_6$H$_3$CH(CH$_3$)— |
| 3-Cl-4-C$_6$H$_4$CH$_2$OC$_6$H$_3$CH$_2$— |
| 3,4-(C$_2$H$_5$CO$_2$)$_2$C$_6$H$_3$CH$_2$— |
| 4-(n-C$_3$H$_7$CO$_2$)C$_6$H$_4$CH$_2$— |
| 4-(i-C$_3$H$_7$CO$_2$)C$_6$H$_4$CH(C$_2$H$_5$)— |
| 2-furylmethyl- |
| 5-methyl-2-furylmethyl- |
| 2-thienylmethyl- |
| 5-methyl-2-thienylmethyl- |
| 1-(2-furyl)ethyl- |
| 1-(5-methyl-2-furyl)ethyl- |

EXAMPLE 64

Employing the procedure of Example 62, and starting with the requisite reagents and the appropriate amide from Example 61, the following tetrazole intermediates are synthesized:

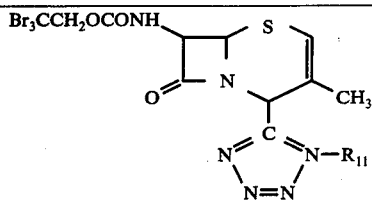

| R$_{11}$ |
|---|
| 4-C$_6$H$_5$CH$_2$OC$_6$H$_4$CH$_2$— |
| 4-C$_6$H$_5$CH$_2$O-3-FC$_6$H$_3$CH$_2$— |
| 2-Cl-4-CH$_3$OC$_6$H$_3$CH$_2$— |
| 4-Cl-4-HOC$_6$H$_3$CH$_2$— |
| 2-Br-4-CH$_3$OC$_6$H$_3$CH$_2$— |
| 2,4-(CH$_3$O)$_2$C$_6$H$_3$CH(CH$_3$)— |
| 4-C$_2$H$_5$CO$_2$C$_6$H$_4$CH$_2$— |
| 3-CH$_3$-4-CH$_3$OC$_6$H$_3$CH$_2$— |
| 3-F-4-CH$_3$CO$_2$C$_6$H$_3$CH$_2$— |
| 3-I-4-CH$_3$OC$_6$H$_3$CH$_2$— |
| 4-(i-C$_3$H$_7$CO$_2$)C$_6$H$_4$CH$_2$— |
| 3,4-(C$_6$H$_5$CH$_2$O)$_2$C$_6$H$_3$CH$_2$— |
| 4-CH$_3$OC$_6$H$_4$CH(CH$_3$)— |
| 4-CH$_3$OC$_6$H$_4$CH(C$_2$H$_5$)— |
| 3,4-(CH$_3$O)$_2$C$_6$H$_3$CH$_2$— |
| 3-F-4-CH$_3$OC$_6$H$_3$CH$_2$— |
| 3-Cl-4-CH$_3$OC$_6$H$_3$CH(CH$_3$)— |
| 4-HOC$_6$H$_4$CH$_2$— |
| 4-HOC$_6$H$_4$CH$_2$— |
| 4-CH$_3$CO$_2$C$_6$H$_4$CH$_2$— |
| 3-Cl-4-HOC$_6$H$_3$CH$_2$— |
| 3-Cl-4-CH$_3$CO$_2$C$_6$H$_3$CH$_2$— |
| 4-C$_6$H$_5$CH$_2$OC$_6$H$_3$CH(CH$_3$)— |
| 3-Cl-4-C$_6$H$_4$CH$_2$OC$_6$H$_3$CH$_2$— |
| 2-F-4-HOC$_6$H$_3$CH$_2$— |
| 3,4-(C$_2$H$_5$CO$_2$)$_2$C$_6$H$_3$CH$_2$— |
| 4-(n-C$_3$H$_7$CO$_2$)C$_6$H$_4$CH$_2$— |
| 2-furylmethyl- |
| 5-methyl-2-furylmethyl- |
| 2-thienylmethyl- |
| 1-(2-furyl)ethyl- |
| 1-(5-methyl-2-furyl)ethyl- |

EXAMPLE 65

7-(2',2',2'-Trichloroethoxycarboxamido)-3-methyl-4-(tetrazol-5-yl)-Δ$^2$-cephem 7-(2',2',2'-Trichloroethoxycarboxamido)-3-methyl-4-[1-(p-methoxybenzyl)tetrazol-5-yl]-Δ$^2$-cephem (40.7 g.) in trifluoroacetic acid (280 ml.) containing anisole (70 ml.) is allowed to stand at 50° C. for 6 hrs. The solution is poured into water (1 liter) and the suspension extracted with ethyl acetate. The organic solution is extracted with saturated aqueous sodium bicarbonate and the aqueous solution is adjusted to pH 2 with 1N HCl acid, and the precipitate extracted into ethyl acetate. The organic solution is dried (MgSO$_4$) and evaporated under reduced pressure to give 7-(2',2',2'-trichloroethoxycarboxamido)-3-methyl-4-(tetrazol-5-yl)-Δ$^2$-cephem as a pale brown solid (23.2 g.). A sample is recrystallized from chloroform (ethanol free) m.p. 165°-167° C.

NMR (DMSOd$_6$): δ = 6.4(q) 1H; 5.8(s) 1H; 5.2(m) 2H; 4.8(s) 2H and 1.8(s) 3H.

EXAMPLE 66

The procedure of Example 65 is repeated, starting with the reagents of Example 63, to produce 7-(2',2',2'-trichloroethoxycarboxamido)-3-methyl-4-(tetrazol-5-yl)-Δ$^2$-cephem, identical with that formed in Example 65.

EXAMPLE 67

Starting with the intermediates of Example 64, and following the procedure of Example 65, 7-(2',2',2'-tribromoethoxycarboxamido)-3-methyl-4-(tetrazol-5-yl)-Δ²-cephem is formed.

EXAMPLE 68

7-(2',2',2'-Trichloroethoxycarboxamido)-3-methyl-4-(methoxymethyltetrazol-5-yl)-Δ²-cephem To a suspension of 7-(2',2',2'-trichloroethoxycarboxamido)-3-methyl-4-(tetrazol-5-yl)-Δ²-cephem (8.27 g.) in methylene chloride (50 ml.) is added in turn, triethylamine (2.22 g.) and chloromethyl methyl ether (1.76 g.) and the solution stirred at room temperature for 30 min. The solution is then washed with water, aqueous sodium bicarbonate, and dried (MgSO₄). Evaporation under reduced pressure gives 7-(2',2',2'-trichloroethoxycarboxamido)-3-methyl-4-(methoxymethyltetrazol-5-yl)-Δ²-cephem (7.3 g.) as a cream solid.

NMR (CDCl₃): δ = 6.4(d) 1H; 6.0(q) 1H; 5.8(s) 2H; 4.7(s) 2H; 3.4(m) 3H and 1.7(s) 3H.

EXAMPLE 69

Employing the appropriate tetrazole of Example 65 or 66 and the requisite alkyl halide, and repeating the procedure of Example 68, the following mixture of compounds is formed:

| R | R₁₁/R₁ |
|---|---|
| Br₃CCH₂OCO— | CH₃OCH₂— |
| Br₃CCH₂OCO— | CH₃CO₂CH₂— |
| Br₃CCH₂OCO— | C₂H₅CO₂CH₂— |
| Br₃CCH₂OCO— | CH₃CO₂CH(CH₃)— |
| Br₃CCH₂OCO— | (CH₃)₂CHCO₂CH₂— |
| Br₃CCH₂OCO— | C₂H₅CO₂CH(CH₃)— |
| Br₃CCH₂OCO— | (CH₃)₃CCO₂CH₂— |
| Br₃CCH₂OCO— | CH₃(CH₂)₂CO₂CH₂— |
| Br₃CCH₂OCO— | (CH₃)₃CCO₂CH(CH₃)— |
| Br₃CCH₂OCO— | CH₃(CH₂)₃CO₂CH₃— |
| Br₃CCH₂OCO— | (CH₃)₂CHCH₂CO₂CH₂— |
| Br₃CCH₂OCO— | C₈H₅O₂—* |
| Cl₃CCH₂OCO— | CH₃CO₂CH₂— |
| Cl₃CCH₂OCO— | CH₃CO₂CH(CH₃)— |
| Cl₃CCH₂OCO— | C₂H₅CO₂CH₂— |
| Cl₃CCH₂OCO— | C₂H₅CO₂CH(CH₃)— |
| Cl₃CCH₂OCO— | (CH₃)₃CCO₂CH₂— |
| Cl₃CCH₂OCO— | (CH₃)₂CHCO₂CH₂— |
| Cl₃CCH₂OCO— | CH₃(CH₂)₃CO₂CH₂— |
| Cl₃CCH₂OCO— | CH₃(CH₂)₃CO₂CH(CH₃)— |
| Cl₃CCH₂OCO— | (CH₃)₂CHCH₂CO₂CH₂— |
| Cl₃CCH₂OCO— | C₈H₅O₂—* |

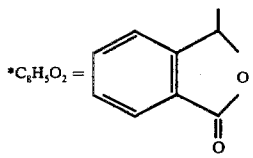

*C₈H₅O₂ =

EXAMPLE 70

7-(2',2',2'-Trichloroethoxycarboxamido)-3-(1-methyltetrazol-5-yl)-4-(methoxymethyltetrazol-5-yl)-Δ²-cephem 7-(2'-2'-2'-Trichloroethoxycarboxamido)-3-methyl-4-(methoxymethyltetrazol-5-yl)-Δ²-cephem (8.0 g.) in carbon tetrachloride (160 ml.) and chloroform (16 ml.) was deoxygenated. N-Bromosuccinimide (3.20 g.) and benzoyl peroxide (200 mg.) is added and the stirred mixture at 10°–15° C. illuminated (250 watt, tungsten lamp) for 2 hrs. During this time additional chloroform is added to maintain a clear supernatant, and a further amount of benzoyl peroxide (200 mg.) added 30 min. after the start of illumination.

The succinimide is filtered off and the filtrate treated with the triethylamine salt of 5-mercapto-1-methyltetrazole (3.40 g.) for 2.5 hrs. at 45° C. The organic solution is then washed with water, aqueous sodium bicarbonate, water and finally dried (MgSO₄). The organic solution is evaporated to dryness under reduced pressure. The residue is purified by means of column chromatography (Silica gel; ethyl acetate; light petroleum ether, 1:1) to gie the desired product (3.0 g.).

NMR (CDCl₃): δ = 6.6(s) 1H; 6.2(d) 1H; 6.0(s) 1H; 5.9(s) 2H; 5.4(m) 2H; 4.8(s) 2H; 4.2(q) 2H; 4.0(s) 3H and 3.5(s) 3H.

EXAMPLE 71

7-(2',2',2'-Trichloroethoxycarboxamido)-3-(2-methyl-1,3,4-thiadiazol-5-yl)-4-methoxymethyltetrazol-5-yl)-Δ²-cephem 7-(2',2',2'-Trichloroethoxycarboxamido)-3-methyl-4-(methoxymethyltetrazol-5-yl)-Δ²-cephem (4.0 g.) in carbon tetrachloride (60 ml.) and chloroform (8 ml.) is treated with N-bromo succinimide and benzoyl peroxide as in Example 70. The product is similarly treated with the triethylamine salt of 5-mercapto-2-methylthiadiazol (2 g.) to give, after column chromatography (silica, ethyl acetate/light petroleum ether 1:1), 7-(2',2',2'-trichloroethoxycarboxamido)-3-(2-methyl-1,3,4-thiadiazol-5-ylthiomethyl)-4-(methoxymethyltetrazol-5-yl)-Δ²-cephem (1.1 g.).

NMR (CDCl₃): δ = 6.6(s) 1H; 6.3(d) 1H; 6.1(s) 1H; 5.9(s) 2H; 5.3-5.7 (m) 2H; 4.8(s) 2H; 4.1(q) 2H; 3.5(s) 3H and 2.7(s) 3H.

EXAMPLE 72

Following the procedure of Example 70 or 71, and starting with the requisite Δ²-cephems from Example 68 and Example 69, and the appropriate mercapten, the following compounds are formed:

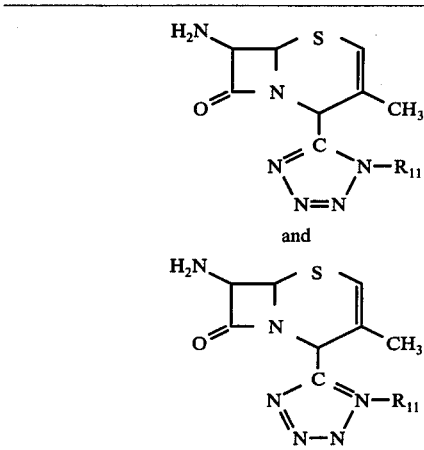

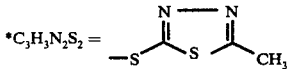

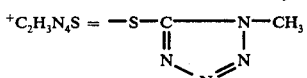

| R | $R_{11}/R_1$ | A |
|---|---|---|
| $Cl_3CCH_2OCO-$ | $CH_3CO_2CH_3-$ | $C_3H_3N_2S_2-$* |
| $Cl_3CCH_2OCO-$ | $CH_3CO_2CH(CH_3)-$ | $C_3H_3N_2S_2-$* |
| $Cl_3CCH_2OCO-$ | $C_2H_5CO_2CH_2-$ | $C_3H_3N_2S_2-$* |
| $Cl_3CCH_2OCO-$ | $(CH_3)_3CCO_2CH_2-$ | $C_3H_3N_2S_2-$* |
| $Cl_3CCH_2OCO-$ | $CH_3(CH_2)_3CO_2CH(CH_3)-$ | $C_3H_3N_2S_2-$* |
| $Cl_3CCH_2OCO-$ | $C_2H_5CO_2CH_3-$ | $C_3H_3N_2S_2-$* |
| $Cl_3CCH_2OCO-$ | $(CH_3)_3CCO_2CH_2-$ | $C_2H_3N_4S-$+ |
| $Cl_3CCH_2OCO-$ | $CH_3CO_2CH_2-$ | $C_2H_3N_4S-$+ |
| $Cl_3CCH_2OCO-$ | #$C_8H_5O_2-$ | $C_2H_3N_4S-$+ |
| $Cl_3CCH_2OCO-$ | $C_2H_5CO_2CH_2-$ | $C_2H_3N_4S-$+ |
| $Cl_3CCH_2OCO-$ | $CH_3CO_2CH(CH_3)-$ | $C_2H_3N_4S-$+ |
| $Br_3CCH_2OCO-$ | $CH_3OCH_2-$ | $C_3H_3N_2S_2-$* |
| $Br_3CCH_2OCO-$ | $CH_3CO_2CH_2-$ | $C_3H_3N_2S_2-$* |
| $Br_3CCH_2OCO-$ | $CH_3CO_2CH(CH_3)-$ | $C_3H_3N_2S_2-$* |
| $Br_3CCH_2OCO-$ | $CH_3(CH_2)CO_2CH_2-$ | $C_3H_3N_2S_2-$* |
| $Br_3CCH_2OCO-$ | $(CH_3)_3CCO_2CH_2-$ | $C_3H_3N_2S_2-$* |
| $Br_3CCH_2OCO-$ | $(CH_3)_2CHCH_2CO_2CH_2-$ | $C_3H_3N_2S_2-$* |
| $Br_3CCH_2OCO-$ | $CH_3OCH_2-$ | $C_2H_3N_4S-$+ |
| $Br_3CCH_2OCO-$ | $CH_3(CH_2)_3CO_2CH(CH_3)-$ | $C_2H_3N_4S-$+ |
| $Br_3CCH_2OCO-$ | $CH_3CO_2CH(CH_3)-$ | $C_2H_3N_4S-$+ |
| $Br_3CCH_2OCO-$ | $(CH_3)_3CCO_2CH_2-$ | $C_2H_3N_4S-$+ |
| $Br_3CCH_2OCO-$ | $CH_3CO_2CH_2-$ | $C_2H_3N_4S-$+ |
| $Br_3CCH_2OCO-$ | $C_2H_5CO_2CH_2-$ | $C_2H_3N_4S-$+ |
| $Br_3CCH_2OCO-$ | #$C_8H_5O_2-$ | $C_2H_3N_4S-$+ |

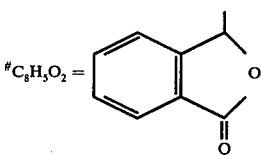

EXAMPLE 73

7-(2′,2′,2′-Trichloroethoxycarboxamido)-3-(1-methyltetrazol-5-ylthiomethyl)-4-(methoxymethyltetrazol-5-yl)-Δ²-cephem (2.0 g.) in acetic acidwater mixture (7:3, 20 ml.) at 0° C. is treated with activated zinc dust (2.0 g.) with stirring. After one hour the mixture is filtered and the filtrate diluted with water (100 ml.). The pH of the mixture was adjusted to 2 with 1N HCl acid and then washed twice with ethyl acetate. The pH of the clear aqueous solution is adjusted to 6 with sodium bicarbonate and the mixture extracted with chloroform. The organic solution is washed with pH 7 buffer, dried (MgSO₄), and, finally, evaporated under reduced pressure to leave 7-amino-3-(1-methyltetrazol-5-ylthiomethyl)-4-(methoxymethyltetrazol-5-yl)-Δ²-cephem (0.9 g.) as a foam, pure by chromatography.

NMR (CDCl₃): δ = 6.6(s) 1H; 5.95(s) 1H; 5.85(s) 2H; 5.25(d) 1H; 4.70 (d) 1H; 4.1(q) 2H; 3.95(s) 3H and 3.5(s) 3H.

In a similar manner is prepared 7-amino-3-(2-methyl-1,3,4-thiadiazol-5-ylthiomethyl)-4-(methoxymethyltetrazol-5-yl)-Δ²-cephem.

NMR (CDCl₃): δ = 6.8(s) 1H; 6.4(s) 1H; 6.0(s) 2H; 5.4(d) 1H; 4.8(d) 1H; 4.2(q) 2H; 3.7(s) 2H.

EXAMPLE 74

By substituting the appropriate compound of Example 69 for the Δ²-cephem of Example 73, and following the experimental procedure of Example 73, the following 7-amino-Δ²-cephems are formed:

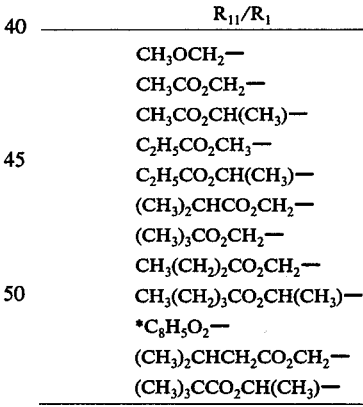

| $R_{11}/R_1$ |
|---|
| $CH_3OCH_2-$ |
| $CH_3CO_2CH_2-$ |
| $CH_3CO_2CH(CH_3)-$ |
| $C_2H_5CO_2CH_3-$ |
| $C_2H_5CO_2CH(CH_3)-$ |
| $(CH_3)_2CHCO_2CH_2-$ |
| $(CH_3)_3CO_2CH_2-$ |
| $CH_3(CH_2)_2CO_2CH_2-$ |
| $CH_3(CH_2)_3CO_2CH(CH_3)-$ |
| *$C_8H_5O_2-$ |
| $(CH_3)_2CHCH_2CO_2CH_2-$ |
| $(CH_3)_3CCO_2CH(CH_3)-$ |

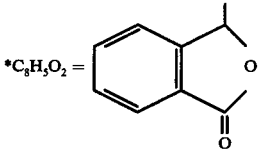

EXAMPLE 75

The procedure of Example 73 is again repeated, starting with the appropriate Δ²-cephems of Example 72, to give the following congeners:

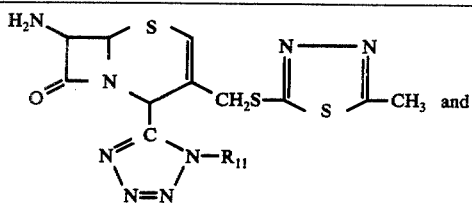

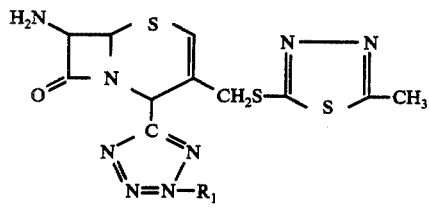

| $R_{11}/R_1$ |
|---|
| $CH_3CO_2CH_2-$ |
| $CH_3CO_2CH(CH_3)-$ |
| $C_2H_5CO_2CH_2-$ |
| $(CH_3)_3CCO_2CH_2-$ |
| $CH_3(CH_2)_3CO_2CH(CH_3)-$ |
| $C_2H_5CO_2CH_2-$ |
| $(CH_3)_2CHCH_2CO_2CH_2-$ |

EXAMPLE 76

Again, the procedure of Example 73, applied to the requisite compounds of Example 72, provides the following intermediates:

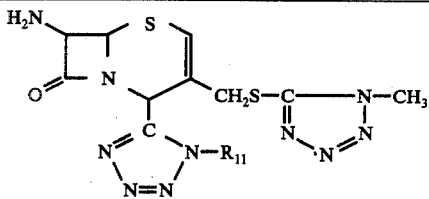

and

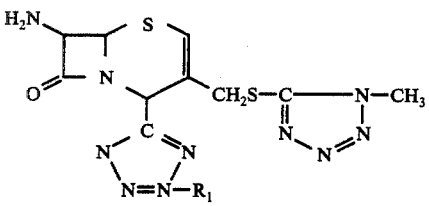

| $R_{11}/R_1$ |
|---|
| $(CH_3)_3CCO_2CH_2-$ |
| $CH_3CO_2CH_2-$ |
| *$C_8H_5O_2-$ |
| $C_2H_5CO_2CH_2-$ |
| $CH_3CO_2CH(CH_3)-$ |
| $CH_3(CH_2)_3CO_2CH(CH_3)-$ |

*$C_8H_5O_2 =$ 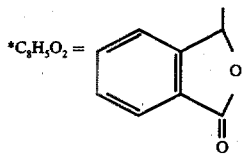

EXAMPLE 77

7-(Tetrazol-1-ylacetamido)-3-(2-methyl-1,3,4-thiadiazol-5-ylthiomethyl)-4-(tetrazol-5-yl)-$\Delta^3$-cephem

A.

7-(Tetrazol-1-ylacetamido)-3-(2-methyl-1,3,4-thiadiazol-5-ylthiomethyl)-4-(methoxymethyltetrazol-5-yl)-$\Delta^2$-cephem 7-Amino-3-(2-methyl-1,3,4-thiadiazol-5-ylthiomethyl-4-(methoxymethyltetrazol-5-yl)-$\Delta^2$-cephem (430 mg.) and tetrazol-1-yl acetic acid (133 mg.) in tetrahydrofuran (10 ml.) and acetonitrile (10 ml.) is treated with dicyclohexylcarbodiimide (215 mg.) and the mixture allowed to stand at room temperature for 1 hr. The mixture is filtered and evaporated under reduced pressure to leave 7-(tetrazol-1-ylacetamido)-3-(2-methyl-1,3,4-thiadiazol-5-ylthiomethyl)-4-(methoxymethyltetrazol-5-yl)-$\Delta^2$-cephem (520 mg.) as a cream solid, pure by thin layer chromatography.

NMR (CDCl$_3$): $\delta$ = 9.1(s) 1H; 6.6(s) 1H 6.0(s) 1H; 5.9(s) 2H; 5.4(s) 2H; 5.4(s) 1H; 5.2(d) 1H; 4.0(q) 2H; 3.4(s) 3H and 2.6(s) 3H.

B.

7-(Tetrazol-1-ylacetamido)-3-(2-methyl-1,3,4-thiadiazol-5-ylthiomethyl)-4-(methoxymethyltetrazol-5-yl)-$\Delta^3$-cephem 1-oxide 7-(Tetrazol-1-ylacetamido)-3-(2-methyl-1,3,4-thiadiazol-5-ylthiomethyl)-4-(methoxymethyltetrazol-5-yl)-$\Delta^2$-cephem (500 mg.) in chloroform (20 ml.) is treated with m-chloroperbenzoic acid (219 mg.) at 0° C. with stirring. After 1 hr. at 0° C. pyridine is added (40 mg.) and the mixture allowed to warm to room temperature. After a further hour the mixture is concentrated under reduced pressure and diethyl ether added to the concentrate. The cream solid which precipitates is collected, dried under reduced pressure and the required product (410 mg.) is obtained as a cream solid, pure by chromatography.

NMR (DMSOd$_6$/acetone d$_6$): $\delta$ = 8.9(s) 1H; 6.0(s) 2H; 6.0, 1H; 5.6(s) 2H; 5.2(d) 1H; 4.5(q) 2H; 4.0 (s) 2H; 3.5(s) 3H and 2.7(s) 3H.

C.

7-(Tetrazol-1-ylacetamido)-3-(2-methyl-1,3,4-thiadiazol-5-ylthiomethyl)-4-(methoxymethyltetrazol-5-yl)-$\Delta^3$-cephem 7-(Tetrazol-1-ylacetamido)-3-(2-methyl-1,3,4-thiadiazol-5-ylthiomethyl)-4-(methoxymethyltetrazol-5-yl)-$\Delta^3$-cephem 1-oxide (400 mg.) in dimethylformamide (10 ml.) is treated with anhydrous stannous chloride (400 mg.) and acetyl chloride (200 mg.) at 0° C. with stirring. The mixture is allowed to stir for 1 hour and is then poured into an excess of water. The aqueous mixture is extracted several times with chloroform, and the organic solution washed several times with water. The chloroform solution is dried (MgSO$_4$) and evaporated under reduced pressure to give the required compound as a foam (250 mg.), pure by thin layer chromatography.

NMR (CDCl$_3$): $\delta$ = 9.0(s) 1H; 8.7(d) 1H; 6.0(s) 2H; 6.0, 1H; 5.4(s) 2H; 5.2(d) 1H; 4.4(q) 2H; 3.7(s) 2H; 3.4(s) 3H and 2.7(s) 2H.

D.
7-(Tetrazol-1-ylacetamido)-3-(2-methyl-1,3,4-thiadiazol-5-ylthiomethyl)-4-(tetrazol-5-yl)-Δ³-cephem 7-(Tetrazol-1-ylacetamido)-3-(2-methyl-1,3,4-thiadiazol-5-ylthiomethyl)-4-(methoxymethyltetrazol-5-yl)-Δ³-cephem (70 mg.) in trifluoroacetic acid (2 ml.) and anisole (0.5 ml.) is allowed to stand at 20° C. for 6 hrs. After this time the trifluoroacetic acid is removed under reduced pressure to leave an oil. This residue is diluted with ethyl acetate and the resulting organic solution extracted with saturated aqueous sodium bicarbonate solution. The aqueous solution is acidified to pH 2 with 2N HCl acid and the solution extracted with ethyl acetate. The organic solution is dried ($MgSO_4$) and evaporated under reduced pressure to leave an oil which crystallizes on addition of diethyl ether, to give the required product as colorless needles (35 mg.), pure by chromatography.

NMR (trifluoroacetic acid-d): δ = 9.5(s) 1H; 5.8(d) 1H; 5.5(s) 2H; 5.2(d) 1H; 4.5(s) 2H; 3.6(s) 2H and 2.8(s) 3H.

EXAMPLE 78

Starting with the appropriate methoxymethyl substituted Δ²-cephems of Examples 73 and 74 and acids, and employing the procedure of Example 77A-D, the following compounds are synthesized:

| Ar | Q | n | A |
|---|---|---|---|
| $C_6H_5$— | — | 0 | H— |
| 2-$ClC_6H_4$— | — | 0 | H— |
| 4-$ClC_6H_4$— | — | 0 | H— |
| 2,3-$Cl_2C_6H_3$— | — | 0 | $C_2H_3N_4S$—* |
| 3,4-$Cl_2C_6H_3$— | — | 0 | $C_2H_3N_4S$—* |
| 3-$FC_6H_4$— | — | 0 | $C_2H_3N_4S$—* |
| 4-$FC_6H_4$— | — | 0 | $C_2H_3N_4S$—* |
| 3,5-$F_2C_6H_3$— | — | 0 | $C_2H_3N_4S$—* |
| 4-$BrC_6H_3$— | — | 0 | $C_2H_3N_4S$—* |
| 3,4-$Br_2C_6H_3$— | — | 0 | $C_2H_3N_4S$—* |
| 3-$HOC_6H_4$— | — | 0 | $C_2H_3N_4S$—* |
| 4-$HOC_6H_4$— | — | 0 | $C_2H_3N_4S$—* |
| 4-$CH_3C_6H_4$— | — | 0 | $C_2H_3N_4S$—* |
| 3-Cl-4-$HOC_6H_3$— | — | 0 | $C_3H_3N_2S_2$—+ |
| 3-F-4-$HOC_6H_3$— | — | 0 | $C_3H_3N_2S_2$—+ |
| 4-$CH_3OC_6H_4$— | — | 0 | $C_3H_3N_2S_2$—+ |
| 3-Br-4-$CH_3OC_6H_3$— | — | 0 | $C_3H_3N_2S_2$—+ |
| 3-$CH_3$-4-$HOC_6H_3$— | — | 0 | $C_3H_3N_2S_2$—+ |
| 3-$CH_3$-4-$ClC_6H_3$— | — | 0 | $C_3H_3N_2S_2$—+ |
| 2-thienyl | — | 0 | $C_3H_3N_2S_2$—+ |
| 3-thienyl- | — | 0 | $C_3H_3N_2S_2$—+ |
| 2-$ClC_6H_4$— | $N_3$ | 1 | H— |
| 4-$ClC_6H_4$— | $N_3$ | 1 | H— |
| 2,4-$Cl_2C_6H_3$— | $N_3$ | 1 | H— |
| 4-$FC_6H_4$— | $N_3$ | 1 | H— |
| 3,5-$F_2C_6H_3$— | $N_3$ | 1 | $C_2H_3N_4S$—* |
| 4-$BrC_6H_4$— | $N_3$ | 1 | $C_2H_3N_4S$—* |
| 4-$HOC_6H_4$— | $N_3$ | 1 | $C_2H_3N_4S$—* |
| 3-$HOC_6H_4$— | $N_3$ | 1 | $C_2H_3N_4S$—* |
| 4-$CH_3OC_6H_4$— | $N_3$ | 1 | $C_2H_3N_4S$—* |
| 3-F-4-$HOC_6H_3$— | $N_3$ | 1 | $C_2H_3N_4S$—* |
| 3-Cl-4-$HOC_6H_3$— | $N_3$ | 1 | $C_2H_3N_4S$—* |
| 3-Br-4-$CH_3OC_6H_3$— | $N_3$ | 1 | $C_3H_3N_2S_2$—+ |
| 4-$CH_3C_6H_4$— | $N_3$ | 1 | $C_3H_3N_2S_2$—+ |
| 3-Cl-4-$CH_3C_6H_3$— | $N_3$ | 1 | $C_3H_3N_2S_2$—+ |
| 4-$CH_3C_6H_4$— | $N_3$ | 1 | $C_3H_3N_2S_2$—+ |
| 3-$CH_3$-4-$CH_3OC_6H_3$— | $N_3$ | 1 | $C_3H_3N_2S_2$—+ |
| 2-thienyl- | $N_3$ | 1 | $C_3H_3N_2S_2$—+ |
| 3-thienyl- | $N_3$ | 1 | $C_3H_3N_2S_2$—+ |

*$C_2H_3N_4S$ =

+$C_3H_3N_2S_2$ =

EXAMPLE 79

7-D-(α-Hydroxy-α-phenylacetamido)-3-(1-methyltetrazol-5-ylthiomethyl)-4-(tetrazol-5-yl)-Δ³-cephem

A.
7-D-(α-Formyloxy-α-phenylacetamido)-3-(1-methyltetrazol-5-ylthiomethyl)-4-(methoxymethyltetrazol-5-yl)-Δ²-cephem Starting with the appropriate reagents and following the procedure of Example 77A, the desired intermediate is prepared.

NMR ($CDCl_3$): δ = 8.2(s) 1H; 7.3(s) 5H; 6.4(s) 1H; 6.2(s) 1H; 5.9(s) 1H; 5.7(s) 2H; 5.5(q) 1H; 5.2(d) 1H; 4.0(q) 2H; 3.9(s) 3H and 3.4(s) 3H.

B.
7-D-(α-Formyloxy-α-phenylacetamido)-3-(1-methyltetrazol-5-ylthiomethyl)-4-(methoxymethyltetrazol-5-yl)-Δ³-cephem 1-oxide Employing the above intermediate from Example 79A and following the procedure of Example 77B, the desired compound is isolated and used in subsequent reaction without further purification.

C.
7-D-(α-Formyloxy-α-phenylacetamido)-3-(1-methyltetrazol-5-ylthiomethyl)-4-(methoxymethyltetrazol-5-yl)-Δ³-cephem The procedure of Example 77C is employed, starting with the appropriate compound from Example 79B, to give the desired product.

NMR ($CDCl_3$): δ = 8.3(s) 1H; 7.4(s) 5H; 6.3(s) 1H; 6.0(s) 2H; 6.0, 1H; 5.2(d) 1H; 4.5(q) 2H; 4.0(s) 3H; 3.8(s) 2H and 3.5(s) 3H.

D.
7-D-(α-Formyloxy-α-phenylacetamido)-3-(1-methyltetrazol-5-ylthiomethyl)-4-(tetrazol-5-yl)-Δ³-cephem The trifluoroacetic acid-anisole treatment of Example 77D is repeated, starting with the product of Example 79C, to provide the desired product.

NMR (acetone-$d_6$/$D_2O$): δ = 8.3(s) 1H; 7.5(m) 5H; 6.2(s) 1H; 5.9(d) 1H; 5.3(d) 1H; 4.4(s) 2H and 4.0(HOD).

(acetone-$d_6$/$D_2O$/trifluoroacetic acid-d): δ = 4.4(s) 2H; 4.0(s) 3H and 3.9(s) 2H.

E.

7-D-(α-hydroxy-α-phenylacetamido)-3-(1-methyltetrazol-5-ylthiomethyl)-4-(tetrazol-5-yl)-Δ³-cephem 7-D-(α-Formyloxy-α-phenylacetamido)-3-(1-methyltetrazol-5-ylthiomethyl)-4-(tetrazol-5-yl)-Δ³-cephem (100 mg.) in aqueous sodium bicarbonate solution (5 ml.) is allowed to stand at room temperature for 3 hrs. The pH of the reaction mixture is adjusted to 2 with 2N HCl acid and extracted with ethyl acetate. The organic solution is dried (MgSO₄) and evaporated under reduced pressure to leave the required product as a cream solid (35 mg.), essentially pure by thin layer chromatography.

EXAMPLE 80

Again, starting with the requisite methoxymethyl substituted Δ²-cephems of Examples 73 and 74 and the appropriately substituted α-formyloxy-α-phenylacetic acid, and employing the procedure of Example 77A-D, the following Δ³-cephems are prepared:

| Ar | *(configuration) | A |
|---|---|---|
| 2-ClC₆H₄— | D | H— |
| 3-ClC₆H₄— | D | H— |
| 3-ClC₆H₄— | D | H— |
| 4-ClC₆H₄— | DL | H— |
| 2-FC₆H₄— | L | H— |
| 4-FC₆H₄— | D | C₂H₃N₄S—* |
| 4-FC₆H₄— | L | C₂H₃N₄S—* |
| 3-BrC₆H₄— | DL | C₂H₃N₄S—* |
| 3-CH₃C₆H₄— | D | C₂H₃N₄S—* |
| 4-CH₃C₆H₄— | DL | C₂H₃N₄S—* |
| 4-CH₃OC₆H₄— | D | C₂H₃N₄S—* |
| 4-CH₃OC₆H₄— | DL | C₂H₃N₄S—* |
| 3-CH₃OC₆H₄— | D | C₂H₃N₄S—* |
| 2-HOC₆H₄— | D | C₂H₃N₄S—* |
| 3-HOC₆H₄— | D | C₂H₃N₄S—* |
| 2-Cl-4-FC₆H₃— | D | C₂H₃N₄S—* |
| 3-Cl-4-FC₆H₃— | DL | C₂H₃N₄S—* |
| 3-Cl-4-BrC₆H₃— | L | C₂H₃N₄S—* |
| 3,4-Br₂C₆H₃— | D | C₂H₃N₄S—* |
| 3-F-4-CH₃C₆H₃— | DL | C₂H₃N₄S—* |
| 3-CH₃-4-CH₃OC₆H₃— | D | C₂H₃N₄S—* |
| 3,4-(HO)₂C₆H₃— | D | C₂H₃N₄S—* |
| 3-Cl-4-HOC₆H₃— | L | C₃H₃N₂S₂—+ |
| 2-F-4-HOC₆H₃— | DL | C₃H₃N₂S₂—+ |
| 2-F-4-CH₃OC₆H₃— | DL | C₃H₃N₂S₂—+ |
| 3,5-(CH₃O)₂C₆H₃— | D | C₃H₃N₂S₂—+ |
| 3-CH₃O-4-HOC₆H₃— | D | C₃H₃N₂S₂—+ |
| 3-Br-5-HOC₆H₃— | L | C₃H₃N₂S₂—+ |
| 3-CH₃-4-HOC₆H₃— | D | C₃H₃N₂S₂—+ |
| 3-CH₃-4-CH₃OC₆H₃— | DL | C₃H₃N₂S₂—+ |
| 3-CH₃-4-CH₃C₆H₃— | DL | C₃H₃N₂S₂—+ |
| 4-HOC₆H₄— | DL | C₃H₃N₂S₂—+ |
| 4-HOC₆H₄— | D | C₃H₃N₂S₂—+ |
| 3-CH₃C₆H₄— | D | C₃H₃N₂S₂—+ |
| 2,4-Cl₂C₆H₃— | D | C₃H₃N₂S₂—+ |
| 2,3-Cl₂C₆H₃— | DL | C₃H₃N₂S₂—+ |
| 3,5-Cl₂C₆H₃— | D | C₃H₃N₂S₂—+ |

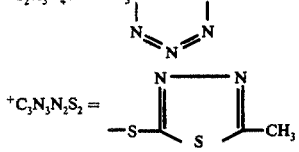

EXAMPLE 81

7-D-(α-Amino-α-phenylacetamido)-3-(1-methyltetrazol-5-ylthiomethyl)-4-(tetrazol-5-yl)-Δ³-cephem trifluoroacetate

A.

7-[D-α-(t-butoxycarbonylamino)-phenylacetamido]-3-(1-methyltetrazol-5-ylthiomethyl)-4-(methoxymethyltetrazol-5-yl)-Δ²-cephem 7-Amino-3-(1-methyltetrazol-5-ylthiomethyl)-4-(methoxymethyltetrazol-5-yl)-Δ²-cephem (100 mg.) and N-t-butoxycarbonylphenylglycine (63.4 mg.) in ethyl acetate-acetonitrile (1:1, 2 ml.) is treated with dicyclohexylcarbodiimide (52 mg.) at 15° C. After one hour the mixture is filtered and the filtrate diluted with ethyl acetate (10 ml.) and the resulting solution washed with 1N HCl acid, aqueous sodium bicarbonate, and finally water. Drying (MgSO₄) and evaporation under reduced pressure gave the product (152 mg.) as a pale yellow solid.

NMR (CDCl₃): δ = 7.25(s) 5H; 6.5(s) 1H; 6.0(s) 1H; 5.8(s) 2H; 5.6(m) 2H; 5.3(m) 2H; 4.1(q) 2H; 3.9(s) 3H; 3.5(s) 3H and 1.4(s) 9H.

B.

7-[D-α-(t-butoxycarbonylamino)phenylacetamido]-3-(1-methyltetrazol-5-ylthiomethyl)-4-(methoxymethyltetrazol-5-yl)-Δ³-cephem 1-oxide 7-[D-α-(t-butoxycarbonylamino)phenylacetamido]-3-(1-methyltetrazol-5-ylthiomethyl)-4-(methoxymethyltetrazol-5-yl)-Δ²-cephem (140 mg., 0.22 mmole) in chloroform (2 ml.) is treated with m-chloroperbenzoic acid (51 mg., 85%) at 0° C. with stirring. The solution is kept at 0° C. for 1 hour and then pyridine (20 mg.) is added and the solution allowed to warm to room temperature and is kept at this temperature for a further 2 hrs.

The reaction mixture is diluted with chloroform and washed with 1N HCl acid, aqueous sodium bicarbonate and dried (MgSO₄). Evaporation under reduced pressure gives the required product as a cream solid (120 mg.).

This material was used directly in the next reaction without further purification.

C.

7-[D-α-(t-butoxycarbonylamino)phenylaceamido]-3-(1-methyltetrazol-5-yl-thiomethyl)-4-(methoxymethyltetrazol-5-yl)-Δ³-cephem 7-[D-α-(t-butoxycarboxylamino)phenylacetamido]-3-(1-methyltetrazol-5-ylthiomethyl)-4-(methoxymethyltetrazol-5-yl)-Δ³-cephem 1-oxide (120 mg.) is suspended in dimethylformamide (0.3 ml.) and acetonitrile (0.75 ml.), and the mixture is treated with acetyl chloride (60 mg.) and anhydrous stannous chloride (38 mg.) with stirring at 0° C. for one hour. The mixture is then allowed to warm up to room temperature and allowed to stir for a further one hour. The mixture is concentrated under reduced pressure and then diluted with ethyl acetate. The organic solution is washed with water and aqueous sodium bicarbonate and finally dried (MgSO₄). Evaporation under reduced pressure gives an oil which was purified by preparative thin layer chromatography (silica, ethyl acetate-light petroleum ether, 3:2) to give the required product as a pale yellow foam (60 mg.).

NMR (CDCl₃): δ = 7.4(s) 5H; 7.2(d) 1H; 5.8(m) 4H; 5.3(d) 1H; 5.2(d) 1H; 4.5(q) 2H; 4.0(s) 3H; 3.8(s) 2H; 3.6(s) 3H and 1.5(s) 9H.

D.

7-D-(α-amino-α-phenylacetamido)-3-(1-methyltetrazol-5-ylthiomethyl-4-(tetrazol-5-yl)-Δ³-cephem trifluoroacetate 7-[D-(α-t-butoxycarbonylamino-α-phenyl)acetamido]-3-(1-methyltetrazol-5-ylthiomethyl)-4-(methoxymethyltetrazol-5-yl)-Δ³-cephem (55 mg.) in trifluoroacetic acid (2 ml.) and anisole (0.5 ml.) is allowed to stand at 20° C. for 6 hrs. The trifluoroacetic acid is evaporated under reduced pressure and the residue treated with ether. The solid which results is collected and washed with portions of dry ether. The solid is dried under high vacuum to give the desired product as the trifluoroacetic acid salt.

NMR (D₂O/DMSOd₆/trifluoroacetic acid-d): δ = 7.4(s) 5H; 5.8(d) 1H; 5.2(d) 1H; 5.1(s) 1H; 4.2(s) 2H; 4.0(s) 3H and 3.6(s) 2H.

EXAMPLE 82

The procedure of Example 81A-D is repeated, starting with the appropriately substituted N-t-butoxycarbonylphenylglycine and requisite methoxymethyl substituted Δ²-cephems of Examples 73 and 74, to provide the following products:

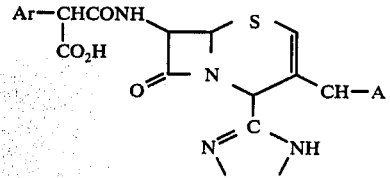

| Ar | *(configuration) | A |
|---|---|---|
| 3-HOC₆H₄— | D | H— |
| 3,4-(HO)₂C₆H₃— | DL | H— |
| 4-(CH₃O)C₆H₄— | D | H— |
| 4-HOC₆H₄— | L | H— |
| 2-thienyl | D | H— |
| 3-Cl-4-HOC₆H₃— | D | H— |
| 4-ClC₆H₄— | DL | C₂H₃N₄S—* |
| 3-ClC₆H₄— | DL | C₂H₃N₄S—* |
| 4-FC₆H₄— | D | C₂H₃N₄S—* |
| 2-Br-5-HOC₆H₃— | DL | C₂H₃N₄S—* |
| 3-FC₆H₄— | D | C₂H₃N₄S—* |
| 4-FC₆H₄— | L | C₂H₃N₄S—* |
| 2-ClC₆H₄— | D | C₂H₃N₄S—* |
| 2-ClC₆H₄— | L | C₂H₃N₄S—* |
| 3-BrC₆H₄— | D | C₂H₃N₄S—* |
| 3-BrC₆H₄— | L | C₂H₃N₄S—* |
| 3-ClC₆H₄— | D | C₂H₃N₄S—* |
| 4-ClC₆H₄— | D | C₂H₃N₄S—* |
| 2,4-Cl₂C₆H₃— | DL | C₂H₃N₄S—* |
| 3,4-Cl₂C₆H₃— | DL | C₃H₃N₂S₂—⁺ |
| 2-FC₆H₄— | D | C₃H₃N₂S₂—⁺ |
| 3-FC₆H₄— | D | C₃H₃N₂S₂—⁺ |
| 3-FC₆H₄— | L | C₃H₃N₂S₂—⁺ |
| 4-BrC₆H₄— | D | C₃H₃N₂S₂—⁺ |
| 3-HOC₆4— | L | C₃H₃N₂S₂—⁺ |
| 4-HOC₆H₄— | DL | C₃H₃N₂S₂—⁺ |
| 3-CH₃C₆H₄— | D | C₃H₃N₂S₂—⁺ |
| 3-CH₆H₄— | L | C₃H₃N₂S₂—⁺ |
| 2-CH₃OC₆H₄— | DL | C₃H₃N₂S₂—⁺ |
| 3,4-(CH₃O)₂C₆H₃— | DL | C₃H₃N₂S₂—⁺ |
| 3,5-(CH₃O)₂C₆H₃— | D | C₃H₃N₂S₂—⁺ |
| 3-thienyl- | D | C₃H₃N₂S₂—⁺ |
| 3-thienyl- | DL | C₃H₃N₂S₂—⁺ |
| 4-CH₃C₆H₄— | D | C₃H₃N₂S₂—⁺ |
| 3-CH₃C₆H₄— | D | C₃H₃N₂S₂—⁺ |
| 3-Cl-4-CH₃C₆H₃— | D | C₃H₃N₂S₂—⁺ |
| 3-Cl-5-(CH₃O)C₆H₃— | D | C₃H₃N₂S₂—⁺ |
| 2-Cl-4-CH₃C₆H₃— | DL | C₃H₃N₂S₂—⁺ |
| 2-F-3-CH₃C₆H₃— | D | C₃H₃N₂S₂—⁺ |

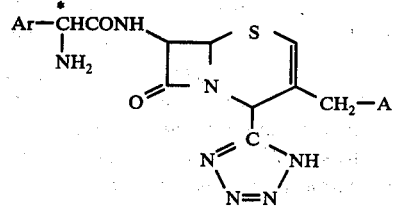

| Ar | *(configuration) | A |
|---|---|---|
| 2-CH₃-4-CH₃OC₆H₃— | DL | C₃H₃N₂S₂—⁺ |

*C₂H₃N₄S =

⁺C₃H₃N₂S₂ =

EXAMPLE 83

Starting with the Δ³-cephem products of Examples 54 through 56 and the appropriately substituted phenylmalonic acid, and employing the procedure of Example 27, the sodium salts of the following compounds are prepared:

| Ar | A |
|---|---|
| 2-ClC₆H₄— | CH₃CO₂— |
| 4-ClC₆H₄— | CH₃CO₂— |
| 3-BrC₆H₄— | CH₃CO₂— |
| 2-FC₆H₄— | CH₃CO₂— |
| 4-FC₆H₄— | C₂H₃N₄S—* |
| 4-CH₃OC₆H₄— | C₂H₃N₄S—* |
| 2-CH₃C₆H₄— | C₂H₃N₄S—* |
| 4-CH₃C₆H₄— | C₂H₃N₄S—* |
| 4-HOC₆H₄— | C₂H₃N₄S—* |
| 4-H₂NC₆H₄— | C₂H₃N₄S—* |
| 2,4-Cl₂C₆H₃— | CH₃CO₂— |
| 3,4-F₂C₆H₃— | CH₃CO₂— |
| 3-F-4-BrC₆H₃— | CH₃CO₂— |
| 3-Cl-4-HOC₆H₃— | CH₃CO₂— |
| 3,4-(CH₃O)₂C₆H₃— | C₃H₃N₂S₂—⁺ |
| 3-F-4-CH₃C₆H₄— | C₃H₃N₂S₂—⁺ |
| 3-Cl-4-H₂NC₆H₃— | C₃H₃N₂S₂—⁺ |
| 3-thienyl- | C₃H₃N₂S₂—⁺ |
| 3-thienyl- | CH₃CO₂— |
| 2-CH₃C₆H₄— | CH₃CO₂— |
| 4-CH₃OC₆H₄— | CH₃CO₂— |

*C₂H₃N₄S =

⁺C₃H₃N₂S₂ =

EXAMPLE 84

Employing the procedure of Example 77A-C, and starting with the appropriate alkanoyloxymethyl and 1-(alkanoyloxy)ethyl substituted Δ²-cephems of Examples 74 through 76, and the appropriate acids the following products are prepared:

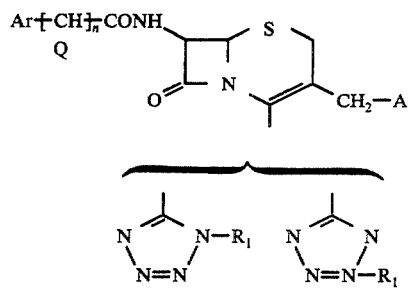

| Ar | Q | n | R₁ | H |
|---|---|---|---|---|
| $C_6H_5-$ | — | 0 | $CH_3CO_2CH_2-$ | $H-$ |
| $2-ClC_6H_4-$ | — | 0 | $CH_3CO_2CH_2-$ | $H-$ |
| $4-ClC_6H_4-$ | — | 0 | $CH_3CO_2CH_2-$ | $H-$ |
| $2,3-Cl_2C_6H_3-$ | — | 0 | $CH_3CO_2CH_2-$ | $H-$ |
| $3,4-Cl_2C_6H_3-$ | — | 0 | $CH_3CO_2CH(CH_3)-$ | $H-$ |
| $3-FC_6H_4-$ | — | 0 | $CH_3CO_2CH(CH_3)-$ | $H-$ |
| $4-FC_6H_4-$ | — | 0 | $CH_3CO_2CH(CH_3)-$ | $H-$ |
| $3,5-F_2C_6H_3-$ | — | 0 | $CH_3CO_2CH(CH_3)-$ | $H-$ |
| $4-BrC_6H_4-$ | — | 0 | $(CH_3)_3CCO_2CH_2-$ | $C_2H_3N_4S-$ * |
| $3,4-Br_2C_6H_3-$ | — | 0 | $(CH_3)_3CCO_2CH_2-$ | $C_2H_3N_4S-$ * |
| $3-HOC_6H_4-$ | — | 0 | $(CH_3)_3CCO_2CH_2-$ | $C_2H_3N_4S-$ * |
| $4-HOC_6H_4-$ | — | 0 | $(CH_3)_3CCO_2CH_2-$ | $C_2H_3N_4S-$ * |
| $4-CH_3C_6H_4$ | — | 0 | $CH_3(CH_2)_3CO_2CH_2-$ | $C_2H_3N_4S-$ * |
| $3-Cl-4-HOC_6H_3-$ | — | 0 | $CH_3(CH_2)_3CO_2CH_2-$ | $C_2H_3N_4S-$ * |
| $3-F-4-HOC_6H_3-$ | — | 0 | $CH_3(CH_2)_3CO_2CH_2-$ | $C_3H_3N_4S_2-$ + |
| $4-CH_3OC_6H_4-$ | — | 0 | $H_3(CH_2)_3CO_2CH_2-$ | $C_3H_3N_{22}S_2-$ + |
| $3-Br-4-CH_3OC_6H_3-$ | — | 0 | $CH_3(CH_2)_3CO_2CH_2-$ | $C_3H_3N_2S_2-$ + |
| $3-CH_3-4-HOC_6H_3-$ | — | 0 | $CH_3(CH_2)_3CO_2CH_2-$ | $C_3H_3N_2S_2-$ + |
| $3-CH_3-4-ClC_6H_3-$ | — | 0 | $C_2H_5CO_2CH_2-$ | $C_3H_3N_2S_2-$ + |
| 2-thienyl- | — | 0 | $C_2H_5CO_2CH_2-$ | $C_3H_3N_2S_2-$ + |
| 3-thienyl- | — | 0 | $CH_3CO_2CH_2-$ | $H-$ |
| $2-ClC_6H_4-$ | $N_3$ | 1 | $CH_3CO_2CH_2-$ | $H-$ |
| $4-ClC_6H_4-$ | $N_3$ | 1 | $CH_3CO_2CH_2-$ | $H-$ |
| $2,4-Cl_2C_6H_3-$ | $N_3$ | 1 | $CH_3CO_2CH_2-$ | $H-$ |
| $4-FC_6H_4-$ | $N_3$ | 1 | $C_2H_5CO_2CH_2-$ | $H-$ |
| $3,5-F_2C_6H_3-$ | $N_3$ | 1 | $C_2H_5CO_2CH_2-$ | $H-$ |
| $4-BrC_6H_4-$ | $N_3$ | 1 | $C_2H_5CO_2CH_2-$ | $H-$ |
| $4-HOC_6H_4-$ | $N_3$ | 1 | $C_2H_5CO_2CH_2-$ | $C_2H_3N_4S-$ * |
| $3-HOC_6H_4-$ | $N_3$ | 1 | $C_2H_5CO_2CH_2-$ | $C_2H_3N_4S-$ * |
| $4-CH_3OC_6H_4-$ | $N_3$ | 1 | $C_2H_5CO_2CH_2-$ | $C_2H_3N_4S-$ * |
| $3-F-4-HOC_6H_3-$ | $N_3$ | 1 | $C_2H_5CO_2CH_2-$ | $C_2H_3N_4S-$ * |
| $3-Cl-4-HOC_6H_3-$ | $N_3$ | 1 | $C_8H_5O-$ # | $C_2H_3N_4S-$ * |
| $3-Br-4-CH_3OC_6H_3-$ | $N_3$ | 1 | $C_8H_5O-$ # | $C_2H_3N_4S-$ * |
| $4-CH_3C_6H_4-$ | $N_3$ | 1 | $C_8H_5O-$ # | $C_2H_3N_4S-$ * |
| $3-Cl-4-CH_3C_6H_3-$ | $N_3$ | 1 | $C_8H_5O-$ # | $C_2H_3N_4S-$ * |
| $4-CH_3C_6H_4-$ | $N_3$ | 1 | $C_8H_5O-$ # | $C_2H_3N_4S-$ * |
| $3-CH_3-4-CH_3OC_6H_3-$ | $N_3$ | 1 | $C_8H_5O-$ # | $C_2H_3N_4S-$ * |
| 2-thienyl- | $N_3$ | 1 | $CH_3(CH_2)_3CO_2CH_2-$ | $C_2H_3N_4S-$ * |
| 3-thienyl | $N_3$ | 1 | $C_8H_5O-$ # | $H-$ |

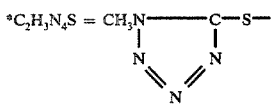

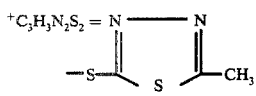

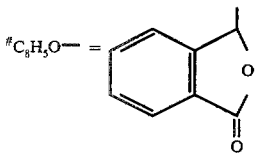

EXAMPLE 85

Again, employing the alkanoyloxymethyl and 1-(alkanoyloxy)ethyl cephems of Examples 74-76 and the appropriate acids, and utilizing the procedure of Example 79-A-C, the following compounds are prepared:

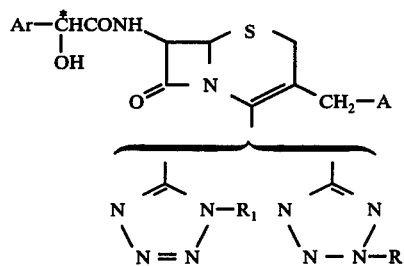

| Ar | *(configuration) | R₁ | A |
|---|---|---|---|
| 2-ClC₆H₄— | D | CH₃CO₂CH₂— | H— |
| 3-ClC₆H₄— | D | CH₃CO₂CH₂— | H— |
| 4-ClC₆H₄— | DL | CH₃CO₂CH₂— | H— |
| 2-FC₆H₄— | L | CH₃CO₂CH₂— | H— |
| 4-FC₆H₄— | D | CH₃CO₂CH₂— | H— |
| 4-FC₆H₄— | L | C₈H₅O—# | H— |
| 4-BrC₆H₄— | DL | C₈H₅O—# | H— |
| 3-CH₃C₆H₄— | D | C₈H₅O—# | H— |
| 4-CH₃C₆H₄— | DL | C₈H₅O—# | H— |
| 4-CH₃OC₆H₄— | D | C₈H₅O—# | C₂H₃N₄S—* |
| 4-CH₃OC₆H₄— | DL | C₈H₅O—# | C₂H₃N₄S—* |
| 3-CH₃OC₆H₄— | D | (CH₃)₃CCO₂CH₂— | C₂H₃N₄S—* |
| 2-HOC₆H₄— | D | (CH₃)₃CCO₂CH— | C₂H₃N₄S—* |
| 3-HOC₆H₄— | D | (CH₃)₃CCO₂CH₂— | C₂H₃N₄S—* |
| 4-HOC₆H₄— | DL | (CH₃)₃CCO₂CH₂— | C₂H₃N₄S—* |
| 4-HOC₆H₄— | D | (CH₃)₃CCO₂CH₂— | C₂H₃N₄S—* |
| 2-CH₃C₆H₄— | D | C₂H₅CO₂CH(CH₃)— | C₂H₃N₄S—* |
| 2,4-Cl₂C₆H₃— | D | C₂H₅CO₂CH(CH₃)— | C₂H₃N₄S—* |
| 2,3-Cl₂C₆H₃— | DL | C₂H₅CO₂CH(CH₃)— | C₂H₃N₄S—* |
| 3,5-Cl₂C₆H₃— | D | C₂H₅CO₂CH(CH₃)— | C₂H₃N₄S—* |
| 2-Cl-4-FC₆H₃— | D | CH₃CO₂CH₂— | C₃H₃N₂S₂—+ |
| 3-Cl-4-FC₆H₃— | DL | CH₃CO₂CH₂— | C₃H₃N₂S₂—+ |
| 3-Cl-4-BrC₆H₃— | L | CH₃CO₂CH₂— | C₃H₃N₂S₂—+ |
| 3,4-Br₂C₆H₃— | D | CH₃CO₂CH₂— | C₃H₃N₂S₂—+ |
| 3-F-4-CH₃C₆H₃— | DL | CH₃CO₂CH₂— | C₃H₃N₂S₂—+ |
| 3-CH₃-4-CH₃-OC₆H₃— | D | CH₃CO₂CH(CH₃)— | C₃H₃N₂S₂—+ |
| 3,4-(HO)₂C₆H₃— | D | CH₃CO₂CH(CH₃)— | C₃H₃N₂S₂—+ |
| 3-Cl-4-HOC₆H₃— | L | CH₃CO₂CH(CH₃)— | H— |
| 2-F-4-HOC₆H₃— | DL | CH₃CO₂CH(CH₃)— | H— |
| 2-F-4-CH₃OC₆H₃— | DL | CH₃CO₂CH(CH₃)— | H— |
| 3,5-)CH₃O)₂C₆H₃— | D | CH₃CO₂CH₂— | H— |
| 3-CH₃O-4-HOC₆H₃— | D | CH₃CO₂CH₂— | C₂H₃N₄S—* |
| 3-Br-5-HOC₆H₃— | L | CH₃CO₂CH₂— | C₂H₃N₄S—* |
| 3-CH₃-4-HOC₆H₃— | D | CH₃COCH₂— | C₂H₃N₄S—* |
| 3-CH₃-4-CH₃OC₆H₃— | DL | (CH₃)₃CCO₂CH₂— | C₂H₃N₄S—* |
| 3-CH₃-4-BrC₆H₃ | D | (CH₃)₃CCOCH₂— | C₂H₃N₄S—* |

*C₂H₃N₄S = 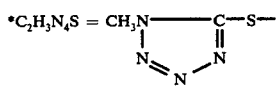

+C₃H₃N₂S₂ = 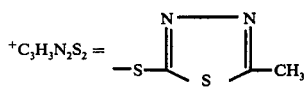

C₈H₅O = 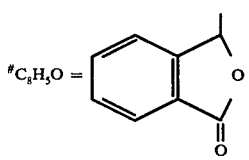

EXAMPLE 86

Utilizing the procedure of Example 81A-C, and starting with the alkanoyloxymethyl and 1-(alkanoyloxy)ethyl Δ²-cephems of Examples 74-76 and the appropriately substituted N-t-butoxycarbonylphenylglycine, the following products are prepared:

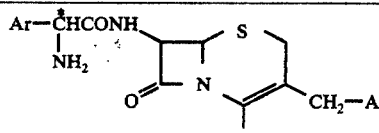
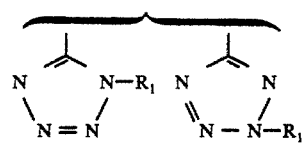

| Ar | *(configuration) | $R_1$ | A |
|---|---|---|---|
| 3-$HOC_6H_4$— | D | $CH_3CO_2CH_2$— | H— |
| 3,4-$(HO)_2C_6H_3$— | DL | $CH_3CO_2CH_2$— | H— |
| 4-$(CH_3O)C_6H_4$— | D | $CH_3CO_2CH_2$— | H— |
| 4-$HOC_6H_4$— | L | $CH_3CO_2CH_2$— | H— |
| 2-thienyl- | D | $CH_3(CH_2)_3CO_2CH_2$— | H— |
| 3-Cl-4-$HOC_6H_3$— | D | $CH_3(CH_2)_3CO_2CH_2$— | H— |
| 4-$ClC_6H_4$— | DL | $CH_3(CH_2)_3CO_2CH_2$— | $C_2H_3N_4S$—* |
| 3-$ClC_6H_4$— | DL | $CH_3(CH_2)_3CO_2CH_2$— | $C_2H_3N_4S$—* |
| 4-$FC_6H_4$— | D | $CH_3(CH_2)_3CO_2CH_2$— | $C_2H_3N_4S$—* |
| 2-Br-5-$HOC_6H_3$— | DL | $(CH_3)_3CCO_2CH_2$— | $C_2H_3N_4S$—* |
| 3-$FC_6H_4$— | D | $(CH_3)_3CCO_2CH_2$— | $C_2H_3N_4S$—* |
| 4-$FC_6H_4$— | L | $(CH_3)_3CCO_2CH_2$— | $C_2H_3N_4S$—* |
| 2-$ClC_6H_4$— | D | $(CH_3)_3CCO_2CH_2$— | $C_2H_3N_4S$—* |
| 2-$ClC_6H_4$— | L | $(CH_3)_3CCO_2CH_2$— | $C_2H_3N_4S$—* |
| 3-$BrC_6H_4$— | D | $(CH_3)_3CCO_2CH_2$— | $C_2H_3N_4S$—* |
| 3-$BrC_6H_4$— | L | $CH_3CO_2CH_2$— | $C_3H_3N_2S_2$—+ |
| 3-$ClC_6H_4$— | D | $CH_3CO_2CH_2$— | $C_3H_3N_2S_2$—+ |
| 4-$ClC_6H_4$— | D | $CH_3CO_2CH_2$— | $C_3H_3N_2S_2$—+ |
| 2,4-$Cl_2C_6H_3$— | DL | $CH_3CO_2CH_2$— | $C_3H_3N_2S_2$—+ |
| 3,4-$Cl_2C_6H_3$— | DL | $C_8H_5O$—# | $C_3H_3N_2S_2$—+ |
| 2-$FC_6H_4$— | D | $C_8H_5O$—# | $C_3H_3N_2S_2$—+ |
| 3-$FC_6H_4$— | D | $C_8H_5O$—# | $C_3H_3N_2S_2$—+ |
| 3-$FC_6H_4$— | L | $C_8H_5O$— | H— |
| 4-$BrC_6H_4$— | D | $C_8H_5O$— | H— |
| 3-$HOC_6H_4$— | L | $C_8H_5O$— | H— |
| 4-$HOC_6H_4$— | DL | $CH_3(CH_2)_3CO_2CH_2$— | H— |
| 3-$CH_3C_6H_4$— | D | $CH_3(CH_2)_3CO_2CH_2$— | H— |
| 3-$CH_3C_6H_4$— | L | $CH_3(CH_2)_3CO_2CH_2$— | H— |
| 2-$CH_3OC_6H_4$— | DL | $CH_3(CH_2)_3CO_2CH_2$— | H— |
| 3,4-$(CH_3O)_2C_6H_3$— | DL | $CH_3(CH_2)_3CO_2CH_2$— | H— |
| 3,5-$(CH_3O)_2C_6H_3$— | D | $CH_3(CH_2)_3CO_2CH_2$— | H— |
| 3-thienyl- | D | $CH_3(CH_2)_3CO_2CH_2$— | $C_2H_3N_4S$—* |
| 3-thienyl- | DL | $(CH_2)_2CHCO_2CH_2$— | $C_2H_3N_4S$—* |
| 4-$CH_3C_6H_4$— | D | $(CH_2)_2CHCO_2CH_2$— | $C_2H_3N_4S$—* |
| 3-$CH_3C_6H_4$— | D | $(CH_2)_2CHCO_2CH_2$— | $C_2H_3N_4S$—* |
| 3-Cl-4-$CH_3C_6H_3$— | D | $(CH_2)_2CHCO_2CH_2$— | $C_2H_3N_4S$—* |
| 3-Cl-5-$(CH_3O)C_6H_3$— | D | $(CH_2)_2CHCO_2CH_2$— | $C_2H_3N_4S$—* |
| 2-Cl-4-$CH_3C_6H_3$— | DL | $(CH_2)_2CHCO_2CH_2$— | $C_2H_3N_4S$—* |
| 2-F-3-$CH_3C_6H_3$— | D | $CH_3CO_2CH(CH_3)$— | $C_2H_3N_4S$—* |
| 2-$CH_3$-4-$CH_3OC_6H_3$— | DL | $CH_3CO_2CH(CH_3)$— | $C_2H_3N_4S$—* |

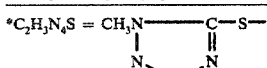

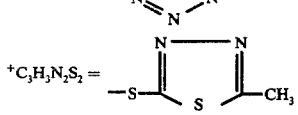

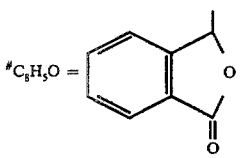

EXAMPLE 87

The procedure of Example 77-A-C is repeated, starting with the requisite acid and alkanoyloxymethyl and 1-alkanoyloxy)ethyl $\Delta^2$-cephems of Examples 74-76, to give the following congeners:

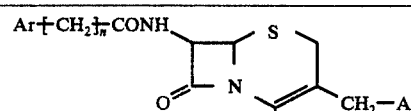

Ar    n    $R_1$    A

| | | | |
|---|---|---|---|
| C₆H₅O— | 1 | CH₃CO₂CH₂— | H— |
| C₆H₅O— | 1 | CH₃(CH₂)₃CO₂CH— | H— |
| C₆H₅O— | 1 | CH₃CO₂CH(CH₃)— | H— |
| C₆H₅O— | 1 | (CH₃)₃CCO₂CH₂— | H— |
| 4-C₅H₃S— | 1 | CH₃CO₂CH₂— | H— |
| 4-C₅H₄S— | 1 | C₂H₅CO₂CH₂— | H— |
| 4-C₅H₄S— | 1 | C₂H₅CO₂CH₂— | C₂H₃N₄S—* |
| 4-C₅H₄S— | 1 | (CH₃)₂CHCO₂CH₂— | C₂H₃N₄S—* |
| 4-C₅H₄S— | 1 | CH₃CO₂CH(CH₃)— | C₂H₃N₄S—* |
| C₆H₅S— | 1 | CH₃CO₂CH(CH₃)— | C₂H₃N₄S—* |
| C₆H₅S— | 1 | (CH₃)₂CHCH₂CO₂CH₂— | C₂H₃N₄S—* |
| C₆H₅S— | 1 | CH₃(CH₂)₂CO₂CH₂— | C₂H₃N₄S—* |
| C₆H₅S— | 1 | C₂H₅CO₂CH(CH₃)— | C₂H₃N₄S—* |
| C₆H₅S— | 1 | C₂H₅CO₂CH(CH₃)— | C₃H₃N₂S₂—+ |
| C₆H₅S— | 1 | (CH₃)₃CCO₂CH₂— | C₃H₃N₂S₂—+ |
| 2-C₄H₃S— | 0 | CH₃CO₂CH₂— | C₃H₃N₂S₂—+ |
| 2-C₄H₃S— | 1 | CH₃CO₂CH₂— | C₃H₃N₂S₂—+ |
| C₆H₅O— | 1 | C₈H₇O—# | H— |
| C₆H₅S— | 1 | C₈H₇O—# | H— |
| CN | 1 | CH₃CO₂CH₂— | H— |
| Br | 1 | CH₃(CH₂)₂CO₂CH₂— | H— |
| 3-C₄H₃S— | 0 | CH₃CO₂CH₂— | H— |
| 3-C₄H₃S— | 1 | CH₃CO₂CH₂— | H— |

EXAMPLE 88

The following ingredients are blended together in the indicated proportions by weight.

| | |
|---|---|
| Sucrose, U.S.P. | 80.0 |
| Tapioca Starch | 13.5 |
| Magnesium stearate | 6.5 |
| 7-Phenylacetamido-3-methyl-4-(tetrazol-5-yl)-Δ³-cephem | 100.0 |

After the composition is thoroughly blended, tablets are punched from the mixture, each tablet being of such size as to contain 100 mg. of the cephem compound.

Tablets are also prepared containing respectively 50 and 250 mg. of active ingredient, by selecting the appropriate proportions of cephem compound and excipient blend in each case.

EXAMPLE 89

The following ingredients are blended together in the indicated proportions by weight.

| | |
|---|---|
| Calcium carbonate | 17.6 |
| Dicalcium phosphate | 18.8 |
| Magnesium trisilicate | 5.2 |
| Lactose, U.S.P. | 5.2 |
| Potato starch | 0.8 |
| 7-Phenoxyacetamido-3-methyl-4-(tetrazol-5-yl)-Δ³-cephem | 50.0 |

The thoroughly-mixed pharmaceutical composition is filled into soft gelatin capsules, such that each capsule contains 100 mg. of active ingredient.

Capsules are also prepared containing respectively 50 and 250 mg. of active ingredient by varying the proportions of cephem compound and excipient blend.

EXAMPLE 90

The sodium salt of 7-(2-thienylacetamido)-3-methyl-4-(tetrazol-5-yl)-Δ³-cephem is thoroughly mixed and ground with sodium citrate (4% by weight). The ground, dry mixture is sterilized and packed into sterile vials, which are then stoppered with serum caps under sterile conditions. When it is intended to use this preparation, sufficient sterile water is injected into the vials to dissolve the contents, and give a solution containing 25 mg./ml. of active ingredient. For parenteral use, the solution is withdrawn from the vials using a hypodermic syringe.

In a similar manner, by varying the amount of water added, solutions containing respectively 10, 50, 100 and 200 mg./ml. of active ingredient are prepared.

EXAMPLE 91

7-[D-(α-Amino-α-phenyl)acetamido]-3-methyl-4-(tetrazol-5-yl)-Δ³-cephem Potassium Salt To a stirred solution of 1.94 g. 7-[D-(α-amino-α-phenyl)acetamido]-3-methyl-4-(tetrazol-5-yl)-Δ³-cephem in 100 ml. of methanol, cooled to −30° C., is added dropwise sufficient 1.0N solution of potassium hydroxide in methanol such that one equivalent of base is added. The mixture is allowed to warm to 0° C., and then it is added dropwise with stirring to 700 ml. of ether. The solid which precipitates is removed by filtration and dried under high vacuum. This affords the title potassium salt in good yield.

When the above procedure is repeated, except that the potassium hydroxide used therein is replaced by an equimolar amount of sodium hydroxide, the product is the sodium salt of 7-[D-(α-amino-α-phenyl)acetamido]-3-methyl-4-(tetrazol-5-yl)-Δ³-cephem.

EXAMPLE 92

7-[D-α-Amino-α-(p-hydroxyphenyl)acetamido]-3-methyl-4-(tetrazol-5-yl)-Δ³-cephem Calcium Salt To a stirred solution of 3.87 g. of 7-[D-α-amino-α-(p-hydroxyphenyl)acetamido]-3-methyl-4-(tetrazol-5-yl)-Δ³-cephem in 40 ml. of dimethylformamide is added a turbid solution of 370 mg. of calcium hydroxide over 5 minutes. The mixture is heated at 35°–40° C. for 1 hour, and then an additional 30 ml. of dimethylformamide is added. Heating at 35°–40° C. is continued for a further 30 minutes, and then the cooled solution is added dropwise to 700 ml. of ether. An oil precipitates. The solvent is decanted off and to the residue is added 100 ml. of ethanol, followed by 400 ml. of ether. The oil slowly solidifies and then it is recovered by filtration and dried under high vacuum. This affords the title calcium salt.

EXAMPLE 93

7-[D-(α-Amino-α-phenyl)acetamido]-3-methyl-4-(tetrazol-5-yl)-Δ³-cephem Hydrochloride Salt A slurry of 50 mg. of 7-[D-(α-amino-α-phenyl)acetamido]-3-methyl-4-(tetrazol-5-yl)-Δ³-cephem in 2 ml. of de-ionized water is stirred for 5 minutes at ambient temperature. The pH is then adjusted to 2.45 using dilute hydrochloric acid, and the solution thus obtained is immediately lyophilized. This affords the hydrochloride salt of the desired compound, a white solid.

What is claimed is:

1. A compound selected from the group consisting of

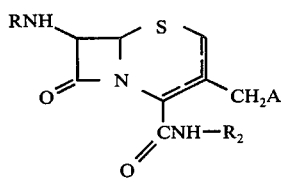

wherein

R is is selected from the group consisting of 2,2,2-trichloroethoxycarbonyl, 2,2,2-tribromoethoxycarbonyl, benzyloxycarbonyl and

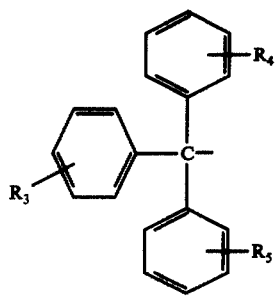

wherein
R₃, R₄ and R₅ are each selected from the group consisting of hydrogen, chloro, bromo, fluoro, methyl, methoxy and phenyl;
A is selected from the group consisting of 1-methyl-5-tetrazolylthio and 2-methyl-1,3,4-thiadiazolyl-5-thio; and
R₂ is selected from the group consisting of

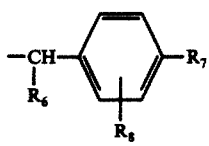

wherein

R₆ is selected from the group consisting of alkyl having from one to three carbon atoms and phenyl and R₇ is selected from the group consisting of hydroxy, methoxy, alkanoyloxy having two to four carbon atoms and benzyloxy and R₈ is selected from the group consisting of hydrogen, hydroxy, fluoro, chloro, bromo, iodo, methyl, methoxy, alkanoyloxy having from two to four carbon atoms, phenyl and benzyloxy and

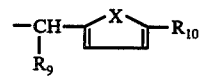

wherein
R₉ and R₁₀ are each selected from the group consisting of hydrogen and methyl and X is selected from the group consisting of oxygen and sulfur.

2. The compound of claim 1, wherein A is selected from the group consisting of 1-methyl-5-tetrazolythio and 2-methyl-1,3,4-thiadiazolyl-5-thio.

3. A compound of claim 2, wherein R₂ is p-methoxybenzyl and A is 1-methyl-5-tetrazolylthio.

4. The compound of claim 3, 7-benzyloxycarboxamido-3-(1-methyl-tetrazol-5-ylmethyl)-4-[N-(p-methoxybenzyl)carbamyl]-Δ³ cephem.

5. A compound of claim 2, wherein R₂ is p-methoxybenzyl and A is 2-methyl-1,3,4-thiadiazolyl-5-thio.

6. The compound of claim 5, 7-benzyloxycarboxamido-3-(2-methyl-1,3,4-thiadiazol-5-ylthiomethyl)-4-[N-(p-methoxybenzyl)carbamyl]-Δ³ cephem.

* * * * *